US012643935B2

(12) United States Patent  
Takahashi et al.

(10) Patent No.: US 12,643,935 B2  
(45) Date of Patent: Jun. 2, 2026

---

(54) PD-L1 BINDING PEPTIDES

(71) Applicants: UNIVERSITY OF SOUTHERN CALIFORNIA, Los Angeles, CA (US); BOARD OF REGENTS, THE UNIVERSITY OF TEXAS SYSTEM, Austin, TX (US)

(72) Inventors: Terry Takahashi, Los Angeles, CA (US); Richard W. Roberts, Los Angeles, CA (US); Golnaz Kamalinia, Los Angeles, CA (US); Justin Ong, Los Angeles, CA (US); Brian Grindel, Austin, TX (US); Brian Engel, Austin, TX (US); Steven Millward, Austin, TX (US)

(73) Assignees: UNIVERSITY OF SOUTHERN CALIFORNIA, Los Angeles, CA (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 670 days.

(21) Appl. No.: 17/997,507

(22) PCT Filed: Apr. 29, 2021

(86) PCT No.: PCT/US2021/029929  
§ 371 (c)(1),  
(2) Date: Oct. 28, 2022

(87) PCT Pub. No.: WO2021/222593  
PCT Pub. Date: Nov. 4, 2021

(65) Prior Publication Data  
US 2023/0174616 A1     Jun. 8, 2023

Related U.S. Application Data

(60) Provisional application No. 63/017,360, filed on Apr. 29, 2020.

(51) Int. Cl.  
C07K 14/705 (2006.01)

(52) U.S. Cl.  
CPC .... C07K 14/70532 (2013.01); C07K 2319/60 (2013.01)

(58) Field of Classification Search  
None  
See application file for complete search history.

(56) References Cited

U.S. PATENT DOCUMENTS

| 9,239,332 B2 | 1/2016 | Heath et al. |
| 9,879,046 B2 | 1/2018 | Miller et al. |
| 11,332,500 B2 | 5/2022 | Mudd et al. |
| 11,453,703 B2 | 9/2022 | Keen et al. |
| 2016/0222377 A1 | 8/2016 | Takahashi et al. |
| 2017/0088586 A1 | 3/2017 | Fiacco et al. |
| 2017/0258948 A1 | 9/2017 | Morin et al. |
| 2018/0312539 A1 | 11/2018 | Fiacco et al. |
| 2019/0284249 A1 | 9/2019 | Fiacco et al. |
| 2019/0298770 A1 | 10/2019 | Rabinovich et al. |

FOREIGN PATENT DOCUMENTS

| EP | 3604345 A1 | 2/2020 |
| WO | 200134768 A2 | 5/2001 |

OTHER PUBLICATIONS

Costello et al. (Pancreat Disord Ther; Suppl 4; doi: 10.4172/2165-7092.S4-002) (Year: 2013).*

Caldwell Jr., et al., "Identification and Validation of a PD-L1 Binding Peptide for Determination of PDL1 Expression in Tumors", Scientific Reports, Oct. 2017, 7: 13682, 12pgs.

Chang et al., "Blocking of the PD-1/PD-L1 Interaction by a d-Peptide Antagonist for Cancer Immunotherapy", Angew. Chem. Int. Ed. 2015, 54, 11760-11764.

Kamalinia et al., "mRNA Display Discovery of a Novel Programmed Death Ligand 1 (PD-L1) Binding Peptide (a Peptide Ligand for PD-L1)," ACS Chem. Biol., 15(6):1630-1641, Apr. 2020.

Kuan et al., "Developing native peptide-based radiotracers for PD-L1 PET imaging and improving imaging contrast by pegylation", Chem. Commun. 2019, 55 (29), 4162-4165.

Li et al., "Peptide Blocking of PD-1/PD-L1 Interaction for Cancer Immunotherapy," Cancer Immunol Res., 6(2): 178-188, Feb. 2018.

Maute et al., "Engineering high-affinity PD-1 variants for optimized immunotherapy and immuno-PET imaging", Proc Natl Acad Sci USA, Nov. 24, 2015, 112(47): E6506-E6514.

Supplementary International Search Report of the ISA/EP in PCT/US2021/029929, dated Mar. 29, 2022, 11pgs.

* cited by examiner

*Primary Examiner* — Sergio Coffa  
(74) *Attorney, Agent, or Firm* — Haukaas Fortius PLLC; Michael H. Haukaas; Paul K. Judd

(57) ABSTRACT

The disclosure provides synthetic peptides that selectively bind to the PD-L1 protein on the surface of cells expressing PD-L1. The PD-L1 binding peptide may comprises the amino acid sequence $MX_1X_2X_3X_4DHX_5LNKFX_6IX_7HXsX_9X_{10}X_{11}X_{12}X_{13}$ (SEQ ID NO: 177) or $MXIF\pi XXIXXX\Omega WXLXXA$ (SEQ ID NO: 1). Peptides of the disclosure may be functionalized using one or more diagnostic agents to aid in various detection modalities or with a cytotoxic agent to treat various disease states such as cancer. Also provided are compositions that include the PD-L1 binding peptides or functionalized PD-L1 binding peptides.

20 Claims, 21 Drawing Sheets  
Specification includes a Sequence Listing.

A
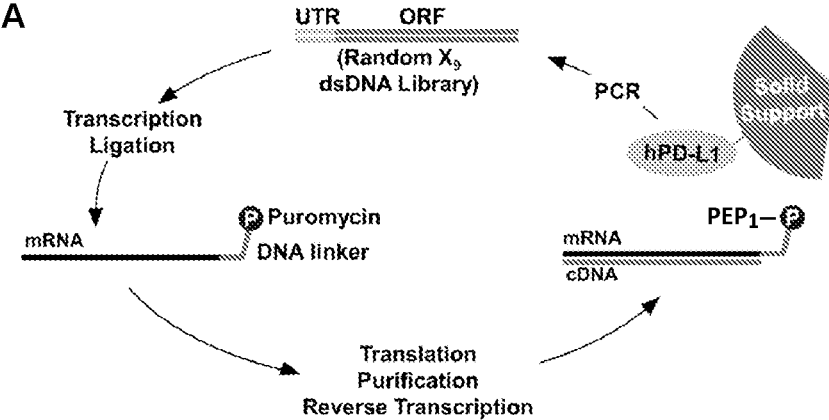
B
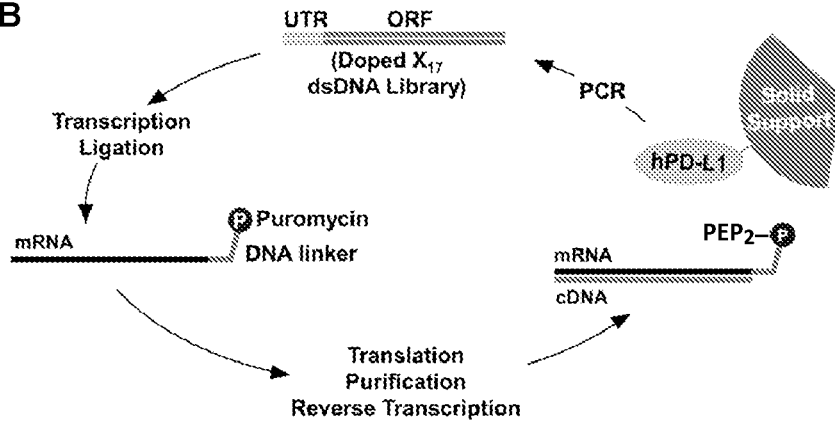
*Fig. 1*

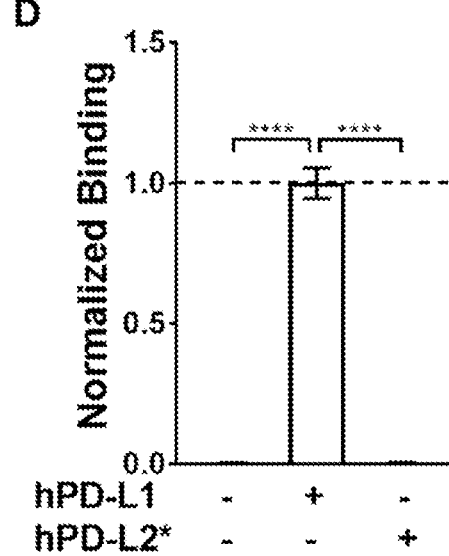
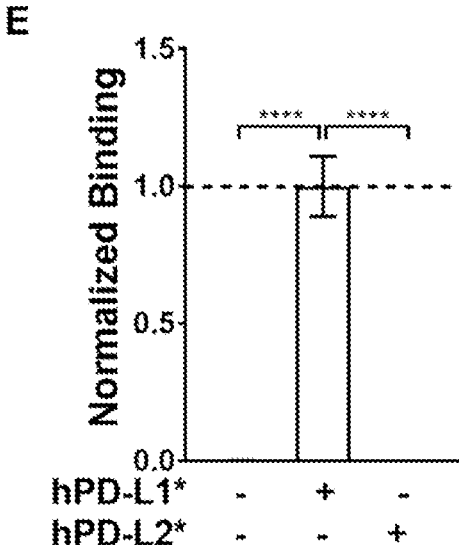
*Fig. 2 (cont.)*

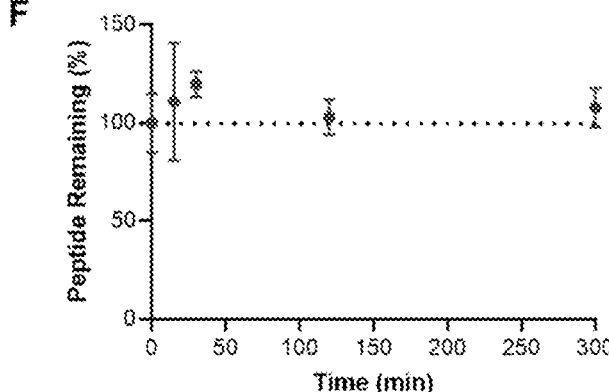
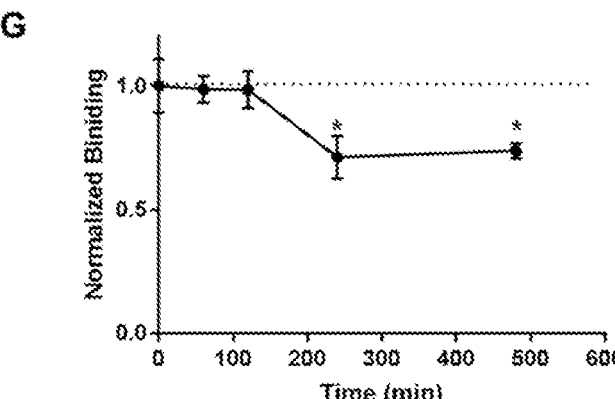
*Fig. 2 (cont.)*

A
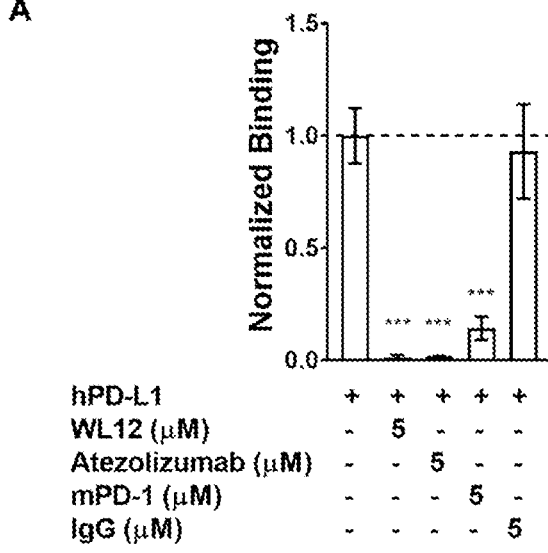
B
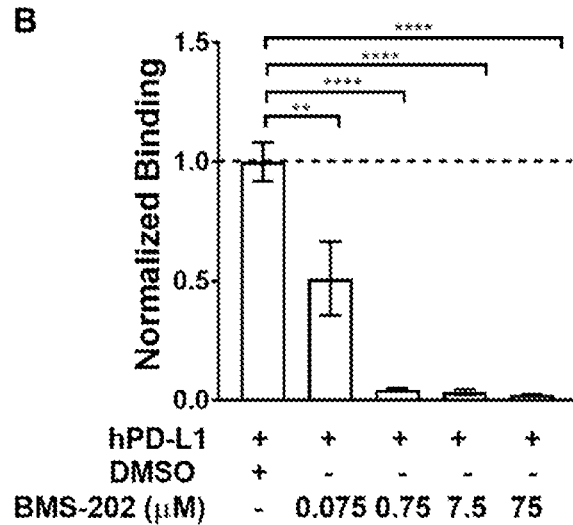
*Fig. 4*

C
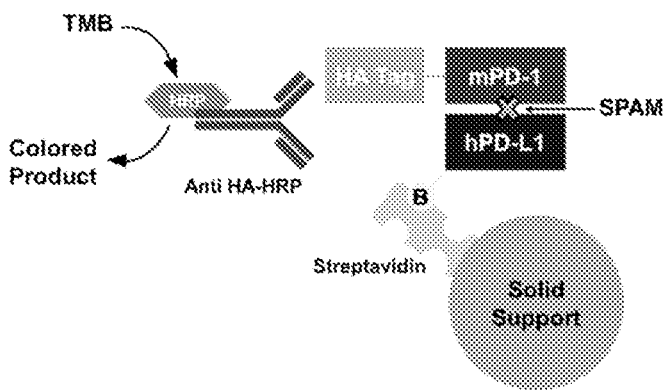
D
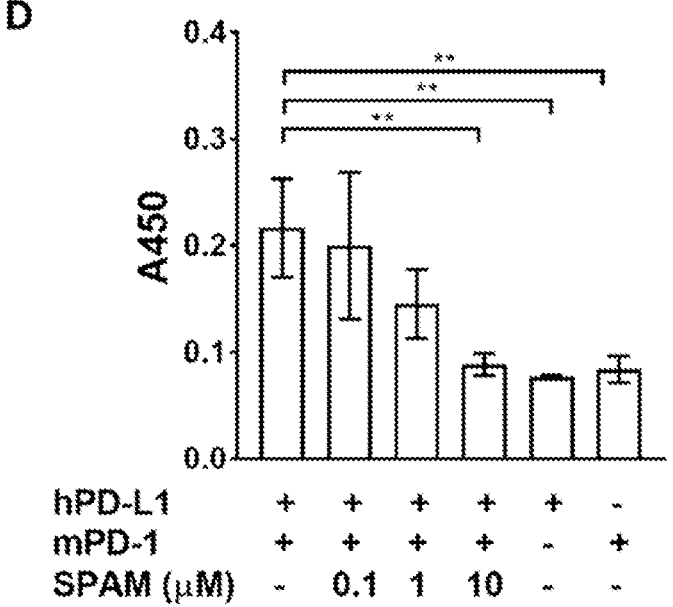
*Fig. 4 (cont.)*

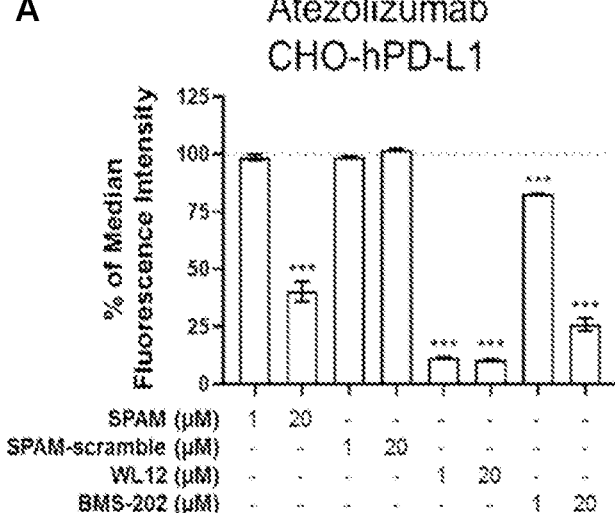
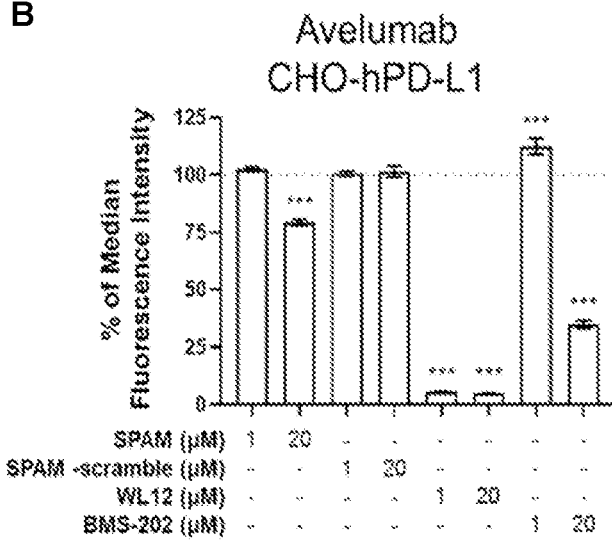
Fig. 5

C
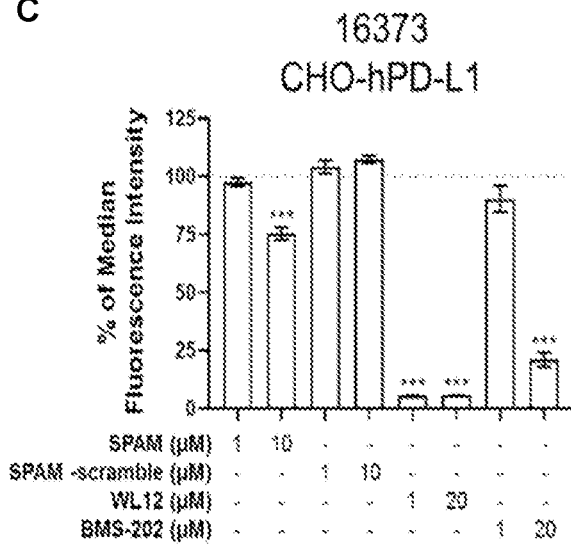
D
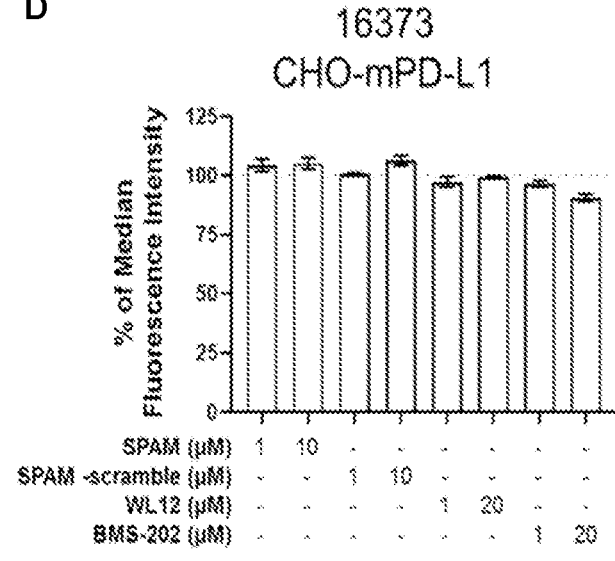
*Fig. 5 (cont.)*

E
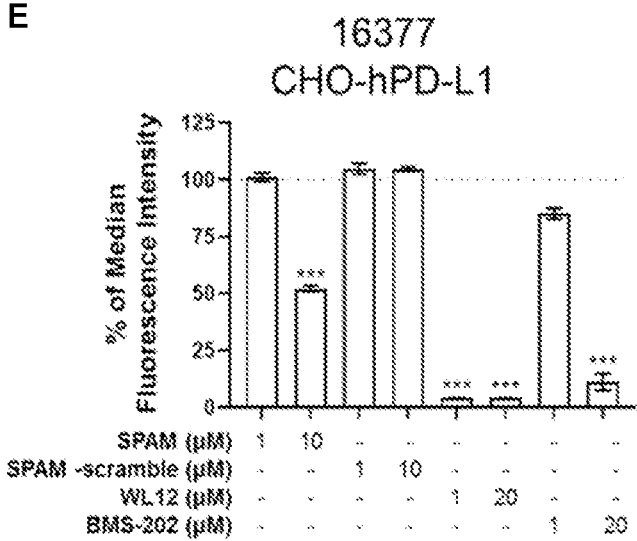
F
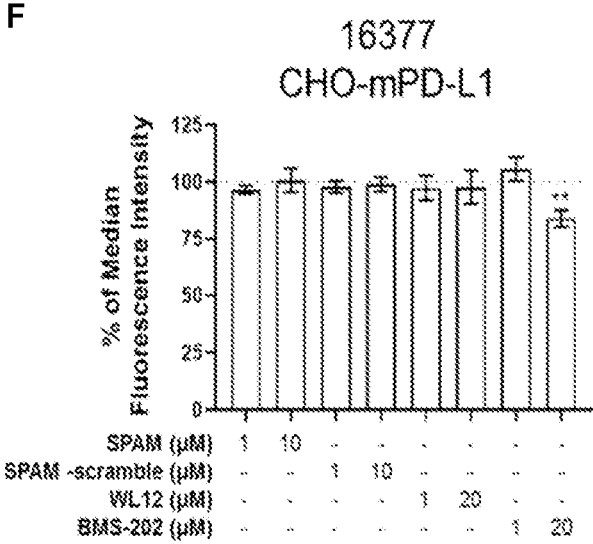
*Fig. 5 (cont.)*

A
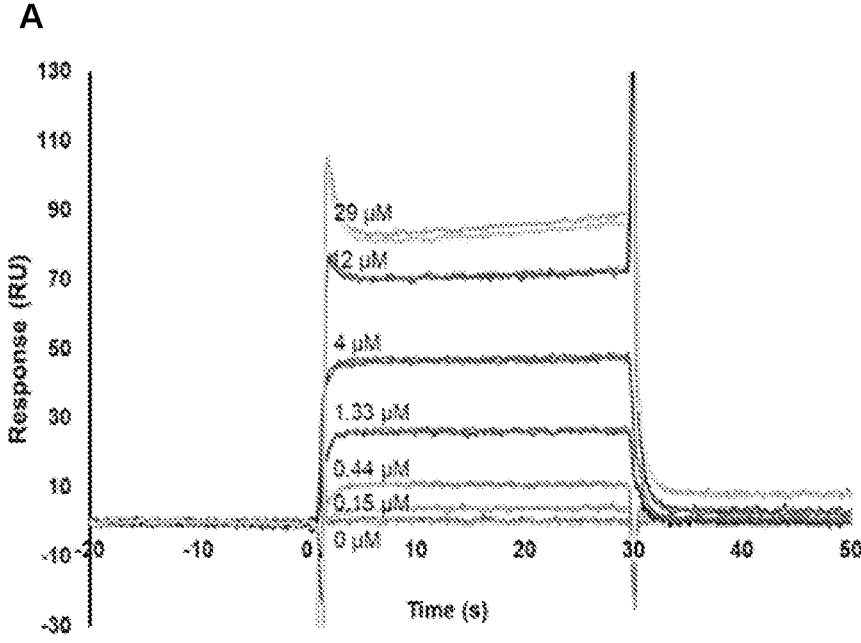
B
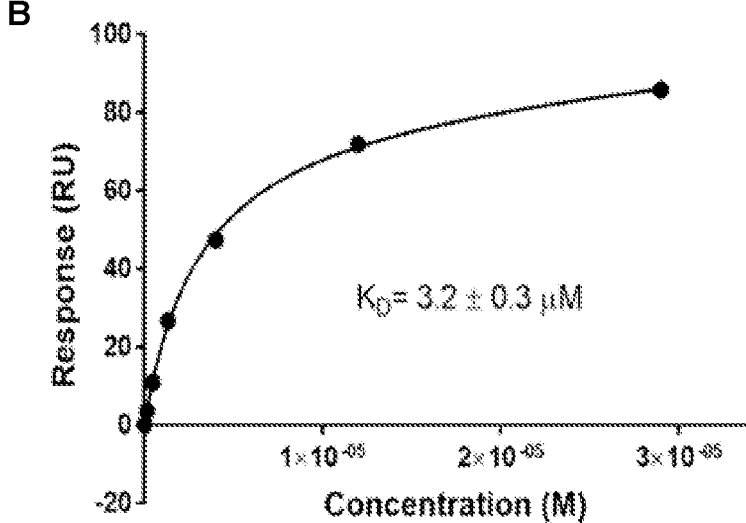
*Fig. 6*

A

| | | |
|---|---|---|
| hPD-L1 | MRIFAVFIFMTYWHLLNAFTVTVPKDLYVVEYGSNMTIECKFPVEKQLDLAALIVYWEME | 60 |
| mPD-L1 | MRIFAGIIFTACCHLLRAFTITAPKDLYVVEYGSNVTMECRFPVERELDLLALVVYWEKE | 60 |
| | *** **** :* *********::.: *:*:***** *:: * :: *:*::.*:** * | |

| | | |
|---|---|---|
| hPD-L1 | DKNIIQFVHGEEDLKVQHSSYRQRARLLKDQLSLGNAALQITDVKLQDAGVYRCMISYGG | 120 |
| mPD-L1 | DEQVIQFVAGEEDLKPQHSNFRGRASLPKDQLLKGNAALQITDVKLQDAGVYCCIISYGG | 120 |
| | *::.**.** . :* **:* ***:*.*******************::** | |

| | | |
|---|---|---|
| hPD-L1 | ADYKRITVKVNAPYNKINQRILVVDPVTSEHELTCQAEGYPKAEVIWTSSDHQVLSGKTT | 180 |
| mPD-L1 | ADYKRITLKVNAPYRKINQRI-SVDPATSEHELICQAEGYPEAEVIWTNSDHQPVSGKRS | 179 |
| | *****:**:*  .*.***:***:**.:* **** :: | |

| | | |
|---|---|---|
| hPD-L1 | TTNSKREEKLFNVTSTLRINTTTNEIFYCTFRRLDPEENHTAELVIPELPLAHPPNERTH | 240 |
| mPD-L1 | VTTSRTEGMLLNVTSSLRVNATANDVFYCTFWRSQPGQNHTAELIIPELPATHPPQNRTH | 239 |
| | .* :* * *  **::*:*:*::*******:* *. :***::*. :*:.*** | |

| | | |
|---|---|---|
| hPD-L1 | LVILGAILLCLGVALTFIFRLRKG-RMMDVKKCGIQDTNSKKQSDTHLEET | 290 |
| mPD-L1 | WVLLGSILLFLIVVSTVLLFLRKQVRMLDVEKCGVEDTSSKNRNDTQFEET | 290 |
| | :*:.* *:*:.*.::*: ::*::.::** :* | |

```
hPD-L1  --MRIFAVFIFMTYWHLLNAFTVTVPKDLYVVEYGSNMTIECKFPVEKQLDLAALIVYWE   58
hPD-L2  MIFLLLMLSLELQLHQIAALFTVTVPKELYIIEHGSNVTLECNFDTGSHVNLGAITASLQ   60 hPD-L1  MEDKNIIQFVHGEEDLKVQHSSYRQRARLLKDQLSLGNAALQITDVKLQDAGVYRCMISY   118
hPD-L2  KVENDT----------SPHRERATLLEEQLPLGKASFHIPQVQVRDEGQYQCIIIY      106 hPD-L1  GGA-DYKRITVKVNAPYNKINQRILVVDPVTSEHELTCQAEGYPKAEVIWTSSDHQVLSG   177
hPD-L2  GVAWDYKYLTLKVKASYRKINTHILKV-PETDEVELTCQATGYPLAEVSWPN-----VSV   160 hPD-L1  KTTTTNSKREEKLFNVTSTLRINTTTNEIFYCTFRRLDPEENHTAELVIPELPLAHPPNE   237
hPD-L2  PANTSHSRTPEGLYQVTSVLRLKPPPGRNFSCVFQ-----NTHVRELTLASIDLQSQMEP   215 hPD-L1  RTHLVILGAILLCLGVALTFIFRLRKGRMMDVKKCGI---QDTNSKKQSDTHLEET      290
hPD-L2  RTHPTWLLHIFIPFCI-IAFIFIATVIALRKQLCQKLYSSKDTTKRPVTTTKREVNSAI   273
```

| hPD-L1 | mPD-L1 | hPD-L2 |
|--------|--------|--------|
| F19 | F19 | F21 |
| T20 | T20 | T22 |
| D26 | D26 | E28 |
| I54 | V54 | T56 |
| Y56 | Y56 | S58 |
| Q66 | Q66 | – |
| R113 | C113 | Q101 |
| M115 | I115 | I103 |
| S117 | S117 | I105 |
| A121 | A121 | A109 |
| D122 | D122 | D111 |
| Y123 | Y123 | Y112 |
| K124 | K124 | K113 |
| R125 | R125 | Y114 |

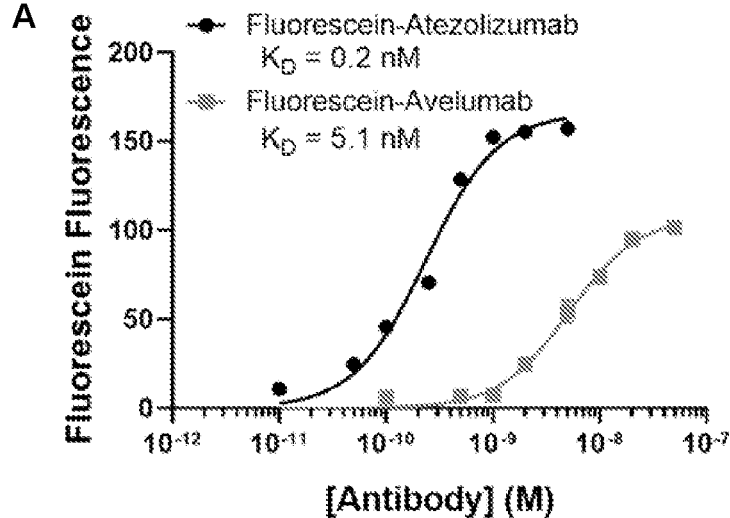
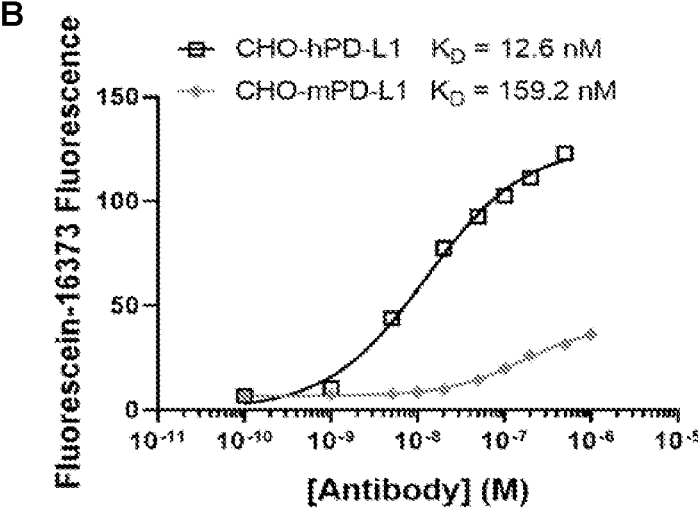
*Fig. 12*

PD-L1 BINDING PEPTIDES

RELATED APPLICATIONS

This application is a National Stage filing under 35 U.S.C. § 371 of International Application No. PCT/US2021/029929 filed Apr. 29, 2021, which claims the benefit of U.S. Provisional Patent Application No. 63/017,360, filed Apr. 29, 2020, which applications are incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 13, 2021, is named 530_017W01_SL.txt and is 83,726 bytes in size.

BACKGROUND OF THE INVENTION

The immune system constantly monitors for the formation of incipient tumor cells and eliminates nascent malignancies before they expand and metastasize (immune surveillance). Tumors, on the other hand, exploit numerous cellular and molecular mechanisms to escape removal by the immune system. Indeed, evading immune destruction is recognized as one of the hallmarks of cancer.

Inhibitory immune checkpoint pathways are among the key mechanisms that enable tumor cells to escape recognition and lysis by T cells. Programmed Death Ligand 1 (PD-L1) is a critical immune checkpoint ligand that is expressed on the surface of tumor cells as well as their myeloid stroma and endothelium in response to inflammatory cytokines such as interferon gamma. PD-L1 engages the Programmed Cell Death Protein 1 (PD-1) receptor on T cells and suppresses immune responses by dampening their activation and effector function. PD-L1 is also expressed on the surface of a variety of cancer cells and its overexpression occurs on tumor cells as a response to T cell infiltration. Binding of tumor PD-L1 to PD-1 on the surface of immune cells deactivates infiltrating cytotoxic T lymphocytes and Natural Killer (NK) cells, thereby attenuating anti-tumor immunity and fostering a state of tumor immune privilege.

Immune checkpoint blockade (ICB) therapy was developed with the goal of blocking the inhibitory interaction between tumor cells and immune cells to reactivate anti-tumor immune responses. Several monoclonal antibodies (mAbs) are clinically approved to inhibit the PD-L1/PD-1 interaction. Atezolizumab, Avelumab, and Durvalumab bind PD-L1 whereas Pembrolizumab Nivolumab, and Cemiplimab bind PD-1 and block its engagement by PD-Ligands. Despite the therapeutic success of antibodies that block the PD-1 pathway both alone and in combination with CTLA-4 blockade across a wide array of cancers, significant limitations still remain. Aside from their high cost and low tumor penetration, the majority of patients on therapeutic ICB mAbs fail to respond clinically and a subpopulation will experience potentially life-threatening immune-related adverse events. As PD-L1 testing has improved in reliability, it has become a mainstay of predicting likelihood of response to PD-1 pathway antibodies; however, all existing tests are performed on a single biopsy specimen which may or may not represent levels of PD-L1 expression across systemic disease. Therefore, PD-L1 ligands with antibody-like affinity, rapid tumor penetration, rapid pharmacokinetics, chemical accessibility, and low costs of production may provide a novel molecular scaffold for development of improved PD-L1-based therapeutics and affinity agents for molecular imaging and in vitro diagnostics.

Directed evolution has previously been used to design PD-L1 binding peptides and proteins that possess a subset of these properties. For example, yeast display has been used to engineer a PD-L1 ligand based on the ectodomain of PD-1. The resulting 14 kDa inhibitor showed improved tumor penetration when compared to anti-PD-L1 antibodies and was successfully used to treat small and large tumor models as a monotherapy or in conjunction with anti-CTLA4 antibodies. In contrast, administration of an anti-PD-L1 mAb was only effective in small tumors, presumably because of attenuated penetration into large tumors due to increased molecular weight. In a subsequent study, a radiolabeled version of this compound was used successfully as a PET radiotracer to visualize PD-L1 expression in xenograft models.

Small peptides that interfere with the PD-L1/PD-1 interaction are predicted to have more favorable pharmacokinetic profiles and lower immunogenicity relative to biologics. Peptides that disrupt the PD-L1/PD-1 interaction have been selected through phage display with dissociation constants ($K_D$) ranging from 117 to 544 nM. In another study, WL12, a macrocyclic peptide developed by Bristol-Meyers Squibb, showed significant binding to PD-L1 and disrupted the PD-L1/PD-1 interaction at low nanomolar concentrations. Although this compound showed promising results as a PET imaging agent, its cyclic structure and multiple unnatural residues make it challenging to synthesize chemically and impossible to express in living systems.

Accordingly, there is a need for a PD-L1 binding peptide that is easily synthesized, has short half-life, and readily binds to PD-L1. The present disclosure satisfies these needs.

SUMMARY OF THE INVENTION

This disclosure uses, inter alia, mRNA display to design novel peptides that selectively bind to human PD-L1 (hPD-L1) and are designated SPAM (Signal Peptide-based Affinity Maturated ligand). SPAM and second-generation SPAM peptides are 18-22 residue linear peptides that are non-homologous to known PD-L1 binding peptides and mAbs. SPAM is highly selective for (hPD-L1) and shows essentially no binding to either mouse PD-L1 (mPD-L1; 77% homology) or human PD-L2 (hPD-L2; more than 30% homology). The SPAM peptide binds both non-glycosylated hPD-L1 and glycosylated hPD-L1 (denoted hPD-L1*) with a $K_D$ of 119 nM and 67 nM, respectively. Finally, the SPAM peptide binds hPD-L1 expressed on the surface of CHO cells and competes with the therapeutic antibodies Atezolizumab and Avelumab, suggesting that the SPAM binding site overlaps the PD-L1/PD-1 binding interface.

Accordingly, certain embodiments of the invention comprise an isolated peptide that binds to human Programmed Death Ligand 1 (PD-L1). Embodiments of the PD-L1 binding peptide can comprise an amino acid sequence of: M-$X_1$-$X_2$-$X_3$-$X_4$-D-H-$X_5$-L-N-K-F-$X_6$-I-$X_7$-H-$X_8$-$X_9$-$X_{10}$-$X_{11}$-$X_{12}$-$X_{13}$ (SEQ ID NO: 170), wherein: $X_1$ is E, F, K, W, or Y; $X_2$ is F, H, K, S, or T; $X_3$ is D, H, K, L, I, N, Q, R, S, or T; $X_4$ is A, F, S, N, V, or T; $X_5$ is I, N, S, T, or V; $X_6$ is F, L, I, W, or Y; $X_7$ is L or M; $X_8$ is E, F, N, Q, or Y; $X_9$ is A,S, or T; $X_{10}$ is A, F, H, I, K, L, M, N, Q, R, S, T, or V; $X_{11}$ is H, K, L, N, Q, R, S, T, or Y; $X_{12}$ is A, G, H, K, N, P, Q, R, S, or T; and $X_{13}$ is A, D, F, G, I, K, L, N, Q, M, S, or T.

In another embodiment, the PD-L1 binding peptide can comprise an amino acid sequence of: M-$X_1$-$X_2$-$X_3$-$X_4$-D-

H-X$_5$-L-N-K-F-X$_6$-I-X$_7$-H-X$_8$-X$_9$-X$_{10}$-X$_{11}$-X$_{12}$-X$_{13}$ (SEQ ID NO: 171), wherein: X$_1$ is E, K, W, or Y; X$_2$ is F, H, S, or T; X$_3$ is D, Q, L, S, R, H, T, or I; X$_4$ is A, S, N, V, or T; X$_5$ is I, N, S, T, or V; X$_6$ is F, L, I, W, or Y; X$_7$ is L or M; X$_8$ is E, F, Q, or Y; X$_9$ is A, S, or T; X$_{10}$ is A, F, L, N, R, T, or V; X$_{11}$ is N, Q, or K; X$_{12}$ is H, P, Q, or S; and X$_{13}$ is F, G, N, Q, M, S, or T.

In one embodiment, the peptide comprises an amino acid sequence that is at least 80%, at least 85%, at least 90% identical, or at least 95% identical to any one of MYTDA-DHILNKFLIMHYARNQQ (SEQ ID NO: 141), MYTQTDHTLNKFLIMHEAFNST (SEQ ID NO: 142), MYSLNDHNLNKFWILHFAVNQM (SEQ ID NO: 143), MYTSTDHILNKFLILHESLQST (SEQ ID NO: 144), MWSRSDHNLNKFWILHYSANPS (SEQ ID NO: 145), MYSRVDHNLNKFWILHQALKSN (SEQ ID NO: 146), MKHSTDHVLNKFYIMHYTANPN (SEQ ID NO: 147), MYTLTDHILNKFWIMHYARNPT (SEQ ID NO: 148), MYSHNDHNLNKFWILHFAVNQM (SEQ ID NO: 149), MEFTSDHSLNKFIILHYANNPF (SEQ ID NO: 150), and MWSITDHNLNKFWILHYATKHG (SEQ ID NO: 151). In another embodiment, the peptide comprises an amino acid sequence identical to any one of SEQ ID NO: 141-151.

In other embodiments, a PD-L1 binding peptide comprises the amino acid sequence MXIFnXXIXXXQWXLXXA (SEQ ID NO: 1), where 71 represents an aliphatic amino acid, X represents any amino acid, and Q represents an aromatic amino acid. In other embodiments, a PD-L1 binding peptide has an amino acid sequence consisting of MXIFπXXIXXXQWXLXXA (SEQ ID NO: 1), where 71 represents an aliphatic amino acid, X represents any amino acid, and Q represents an aromatic amino acid.

In some embodiments of the invention, the PD-L1 binding peptide is at least 80%, at least 85%, at least 90%, or at least 95% identical to MPIFLDHILNKFWILHYA (SEQ ID NO: 3). In other embodiments, the peptide is identical to (SEQ ID NO: 3).

In some embodiments, the PD-L1 binding peptide is formulated as a composition comprising the PD-L1 binding peptide as described herein and a pharmaceutically acceptable carrier.

The disclosure also provides for a method of treating a cancer in a subject wherein the PD-L1 protein is overexpressed on a cell surface of a cancer cell, the method comprising administering an effective amount of the PD-L1 peptide or composition comprising the PD-L1 binding peptide to the subject, thereby treating the cancer.

Other embodiments may be used to detect or image PD-L1 on a surface of a cell. One method of detecting PD-L1 on the surface of a cell comprises contacting a cell with a PD-L1 binding peptide or a composition comprising a PD-L1 binding peptide, thereby detecting the PD-L1.

Other embodiments may be used to detect the presence of PD-L1 in a composition (for example, in a binding assay). One method of detecting PD-L1 comprises contacting the composition comprising or suspected of comprising PD-L1 or a portion thereof with a PD-L1 binding peptide or a composition comprising a PD-L1 peptide, thereby detecting the PD-L1.

These and other features and advantages of this invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1 illustrates the in vitro selection of hPD-L1 binding peptides by mRNA display. A Biotinylated hPD-L1 target was expressed in *E. coli* consisting of the extracellular domain of hPD-L1 (from Ala18 to Thr239), an N-terminal methionine, and a C-terminal hexahistidine tag (SEQ ID NO: 154) and an Avi Tag, which was site-specifically biotinylated on the ε-amino group of lysine (bold) using the BirA biotin ligase (MAFTVTVPKDLYVVEYGSNM-TIECKFPVEKQLDLAALIVYWEMEDKNIIQFVH-GEEDLKVQHSS                YRQRARLLKDQLSLG-NAALQITDVKLQDAGVYRCMISYGGADYKRITVKV NAPYNKINQRILVV              DPVTSEHELTCQAEGYP-KAEVIWTSSDHQVLSGKTTTTNSKREEKLFNVTSTL-RINTTTNEIFYCT FRRLDPEENHTAELVIPELPLAHPP-NERTGGAGGLNDIFEAQKIEWHEGGLEHHHHHH (SEQ ID NO: 152). A) The initial selection was performed using a double stranded DNA library (Random X$_9$ dsDNA Library) where the DNA was consisted of a 5' untranslated region (UTR), a T7 promoter, a ATMV translation enhancer, and an open reading frame (ORF). PEP$_1$ (MXXXXXXXXXGSGTSGSS) (SEQ ID NO: 158) randomized positions are denoted with an "X" and could be any of the 20 natural amino acids.

The DNA library was transcribed into RNA and ligated to a puromycin-bearing DNA linker. The template was subsequently translated, purified, and reverse transcribed to generate the mRNA-peptide fusion library, which was incubated with immobilized hPD-L1. The enriched library was amplified by PCR to generate the DNA library for the next cycle. B) A secondary selection was performed with a doped library (Doped X$_{17}$ dsDNA Library) PEP$_2$ (MXXXXXXXXXXXXXXXXXGSGSSGHHHHHHSS) (SEQ ID NO: 159) where residues denoted by an X were partially doped with the residues in hPD-L1 signal peptide.

Figure 2:
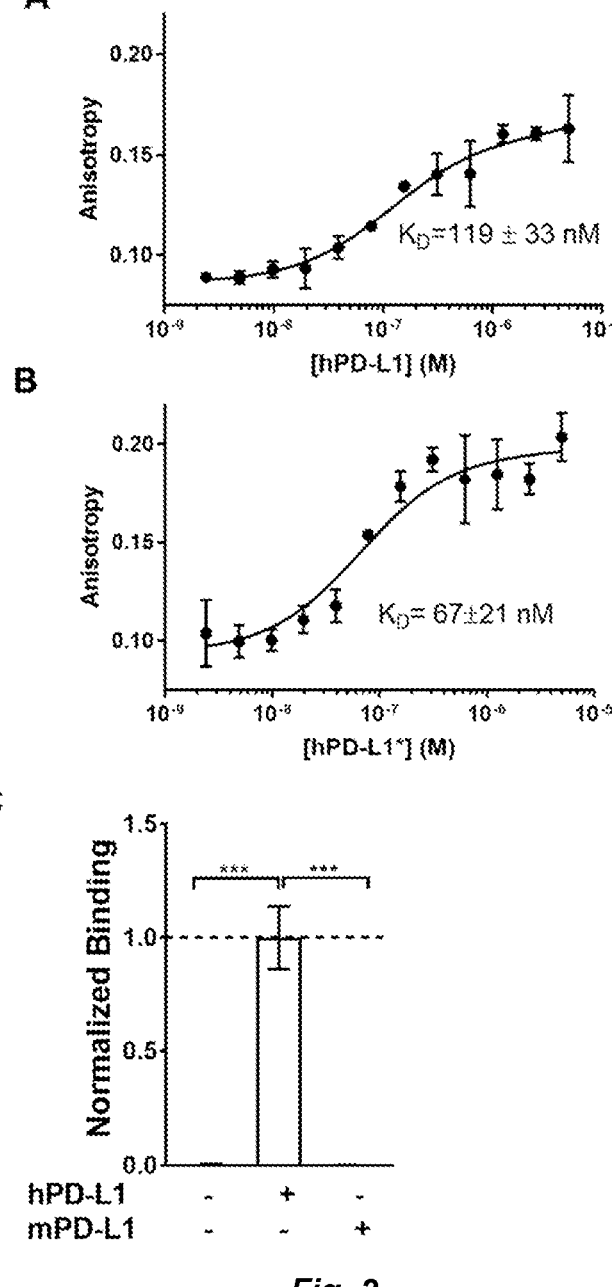

FIG. 2 illustrates the stability and binding of SPAM to hPD-L1 and hPD-L1*. Carboxy-X-rhodamine (ROX)-labeled SPAM peptide (100 nM) was incubated with increasing concentrations (2.4 nM to 5 μM) of A) hPD-L1 and B) hPD-L1* and the anisotropy measured at 21° C. and 22° C., respectively. Each measurement was carried out in triplicate and the mean value was reported along with the standard deviation. The values were fitted to a one-site saturation binding model to obtain the corresponding equilibrium binding constant at 21° C. and 22° C., respectively C) [$^{35}$S]-labeled SPAM binding to hPD-L1 and mPD-L1 D) [$^{35}$S]-labeled SPAM binding to hPD-L1 and hPD-L2* E) [$^{35}$S]-labeled SPAM binding to hPD-L1* and hPD-L2*. F) SPAM peptide is stable in human serum. ROX-SPAM peptide was incubated in 25% human serum for up to five hours and analyzed by HPLC. No change in peptide retention time was observed. G) [$^{35}$S]-labeled SPAM was incubated in 25% human serum for up to eight hours and its binding to hPD-L1 was measured and normalized to the binding of [$^{35}$S]-labeled SPAM not incubated with serum (0-hour sample). The mean of the normalized binding for each incubation time is shown along with the standard deviation of the mean. Each measurement was carried out in triplicate and error bars show the standard deviation of the mean (Students t-test; p value <0.05 (*), <0.01 (), <0.005 (*), <0.001 (****)).

Figure 3:
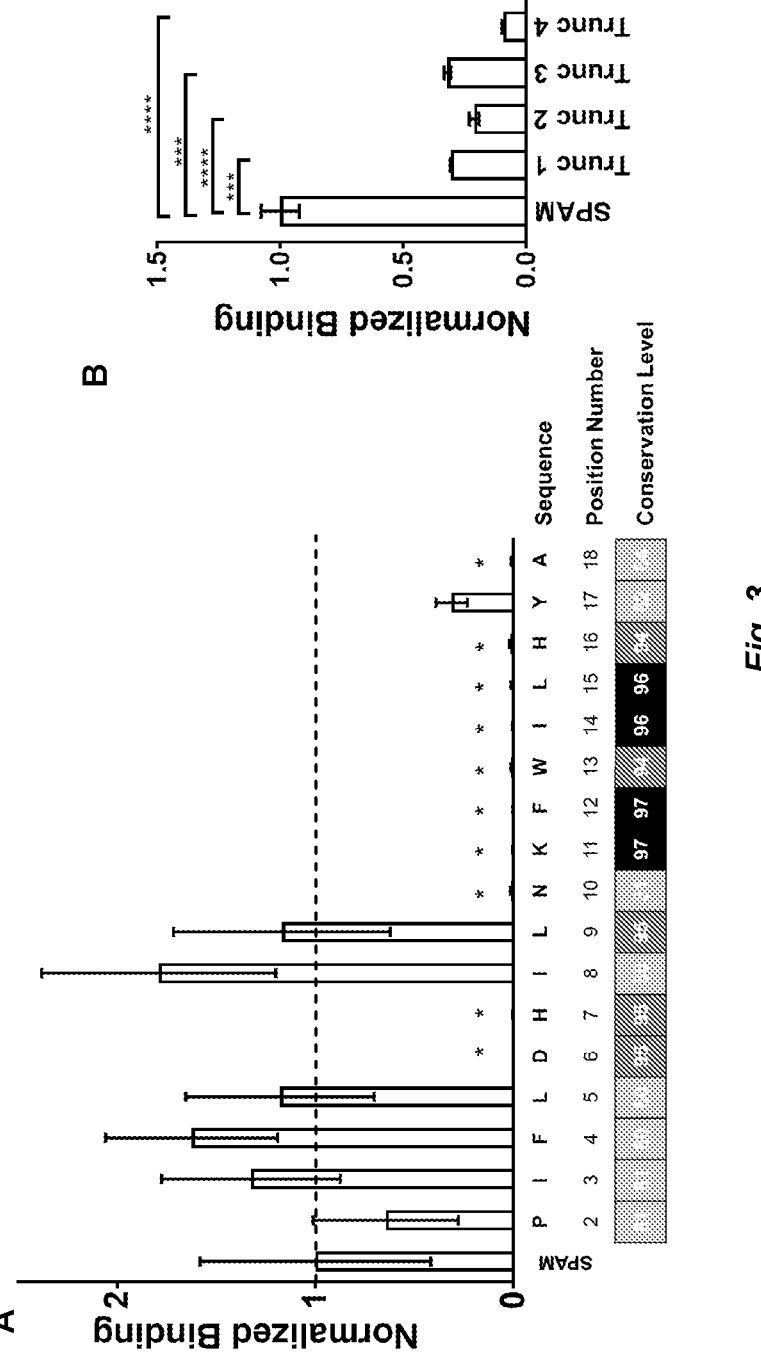

FIG. 3 illustrates a mutational analysis and N-terminal truncation of SPAM shows the residues critical for hPD-L1 binding. A) Mutational analysis of SPAM (MPIFL-DHILNKFWILHYA) (SEQ ID NO: 3); [$^{35}$S]-labeled SPAM variants were translated with alanine substituted at each position (2-18) and glycine substituted for alanine at position 18. hPD-L1 binding of each [$^{35}$S]-SPAM alanine mutant was measured and normalized to the binding of [$^{35}$S]-SPAM. The mean of the normalized binding for each SPAM variant (n=3) is shown along with the standard deviation of the mean. The conservation level for each doped residue in the X$_{17}$ library was obtained from next-generation sequencing data. These results were binned according to sequence family and 108 sequences from SPAM family that appeared more than 1,000 times were identified and the percent conservation relative to the SPAM peptide calculated for each position. FIG. 3 discloses SEQ ID NO: 180. B) [$^{35}$S]-labeled N-terminally truncated versions of SPAM were translated where one (P), two (P, I), three (P, I, F) and four (P, I, F, L) residues were removed from the N-terminus of SPAM creating Trunc 1 (MIFLDHILNKFWILHYA) (SEQ ID NO: 4), Trunc 2 (MFLDHILNKFWILHYA) (SEQ ID NO: 5), Trunc 3 (MLDHILNKFWILHYA) (SEQ ID NO: 6), and Trunc 4 (MDHILNKFWILHYA) (SEQ ID NO: 7), respectively. hPD-L1 binding of each truncated variant was measured and normalized to the binding of [$^{35}$S]-labeled SPAM. The mean of the normalized binding for each SPAM variant (n=3) is shown along with the standard deviation of the mean. Each measurement was carried out in triplicate and error bars show the standard deviation of the mean. (Students t-test; p value <0.05 (*), <0.01 (), <0.005 (*)<0.001 (****)).

FIG. 4 illustrates the SPAM: hPD-L1 interaction is disrupted by hPD-L1-binding ligands. A) [$^{35}$S]-labeled SPAM binding to immobilized hPD-L1 is disrupted by 5 μM WL12 (p value<0.0001), 5 μM Atezolizumab (p value<0.0001) and 5 μM mPD-1 (p value<0.0001). The presence of 5 μM IgG does not affect SPAM binding to hPD-L1 (p value >0.05) B) [$^{35}$S]-SPAM binding to hPD-L1 in the presence of varying concentrations of BMS-202. SPAM binding to hPD-L1 is almost completely inhibited by 750 nM BMS-202 (p value<0.0001). Error bars show the standard deviation of the mean for triplicate measurements. C) Schematic of the hPD-L1/mPD-1 Interaction ELISA/IP assay. D) ELISA/IP assay for hPD-L1 binding to mPD-1 in the presence and absence of different concentrations of SPAM (0.1, 1 and 10 μM). SPAM almost completely inhibits mPD-1 binding at 10 μM (p value <0.01) (Students t-test; p value <0.05 (*), <0.01 (), <0.005 (*), <0.001 (****)).

FIG. 5 illustrates SPAM peptide reduces clinical and cross-reactive anti-PD-L1 antibody binding to CHO-hPD-L1 cells. Cells were pretreated with SPAM peptide, SPAM-scramble peptide, WL-12 or BMS-202 followed by treatment with Fluorescein-labeled antibody and flow cytometry. (A) CHO-hPD-L1 cells labeled with Fluorescein-Atezolizumab. (B) CHO-hPD-L1 cells labeled with Fluorescein-Avelumab. (C) CHO-hPD-L1 cells labeled with Fluorescein-16373 antibody. (D) CHO-mPD-L1 cells labeled with Fluorescein-16373 antibody. (E) CHO-hPD-L1 cells labeled with Fluorescein-16377 antibody. (F) CHO-mPD-L1 cells labeled with Fluorescein-16373 antibody. Bars represent means±SD, n=3. One-way ANOVA with Dunnett's multiple comparison's test p value <0.05 (*), <0.01 (), <0.001 (*).

FIG. 6 illustrates hPD-L1/mPD-1 binding interaction evaluated by Surface Plasmon Resonance (SPR). A) Biotinylated hPD-L1 was immobilized onto a sensor chip SA and variable concentrations of mPD-1 (0.15 to 29 μM) were passed over the target at 50 μL/min for 60 seconds at 25° C. B) The response values (RU) were fitted to a one-site saturation binding model in GraphPad Prism to obtain a dissociation constant (K$_D$) of 3.2+/−0.3 μM.

Figures 7, 8:
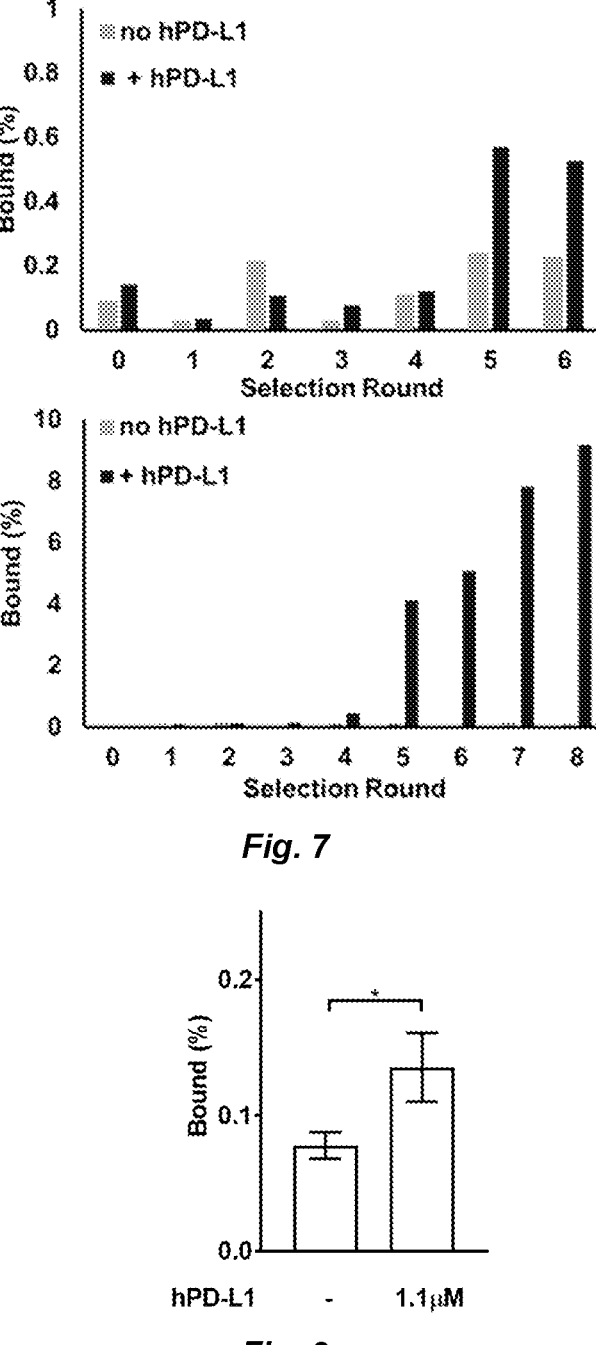

FIG. 7 illustrates mRNA Display selection progress. A) Selection of a random X9 library against hPD-L1. [$^{35}$S]-methionine labeled peptide-mRNA fusions from each round of selection along with the naive pool were evaluated for binding to hPD-L1 or to the matrix only. In round 0, 300 pmol of hPD-L1 was immobilized on neutravidin agarose beads. In all subsequent rounds, 75 pmol of hPD-L1 was immobilized on streptavidin magnetic beads. The selection was performed at 4° C. B) Selection of X17 library against hPD-L1. [$^{35}$S]-methionine labeled peptide-mRNA fusions from each round of selection along with the naive pool were evaluated for binding to hPD-L1 or to the matrix only. In round 0, 300 pmol of hPD-L1 was immobilized on neutravidin agarose beads. In rounds 1 and 2, 75 pmol of the target was immobilized on neutravidin agarose beads. In rounds 3 through 8, 75 pmol of hPD-L1 was immobilized on streptavidin agarose beads. The selection was performed at 4° C. for rounds 0-6 and at room temperature for rounds 7 and 8.

FIG. 8 illustrates [$^{35}$S]-methionine labeled hPD-L1 signal peptide-mRNA fusions binding to heavily loaded hPD-L1 beads vs the matrix only. Each measurement was carried out in triplicate and error bars show the standard deviation of the mean (Students t-test; p value <0.05 (*)).

FIG. 9 illustrates hPD-L1 protein sequence alignment with A) mPD-L1 and B) hPD-L2. Identical residues are marked with (*), similar residues as marked with (:), and non-similar residues unmarked. (The Fasta protein sequence was acquired from uniprot database (hPD-L1 accession code: Q9NZQ7; mPD-L1 accession code: Q9EP73; hPD-L2 accession code: Q9BQ51) and the sequences were compared using Basic Local Alignment Search Tool (BLAST) (blast.ncbi.nlm.nih.gov/Blast.cgi #). FIG. 9 discloses SEQ ID NOS 178-179, 178, and 181, respectively, in order of appearance.

Figure 10:
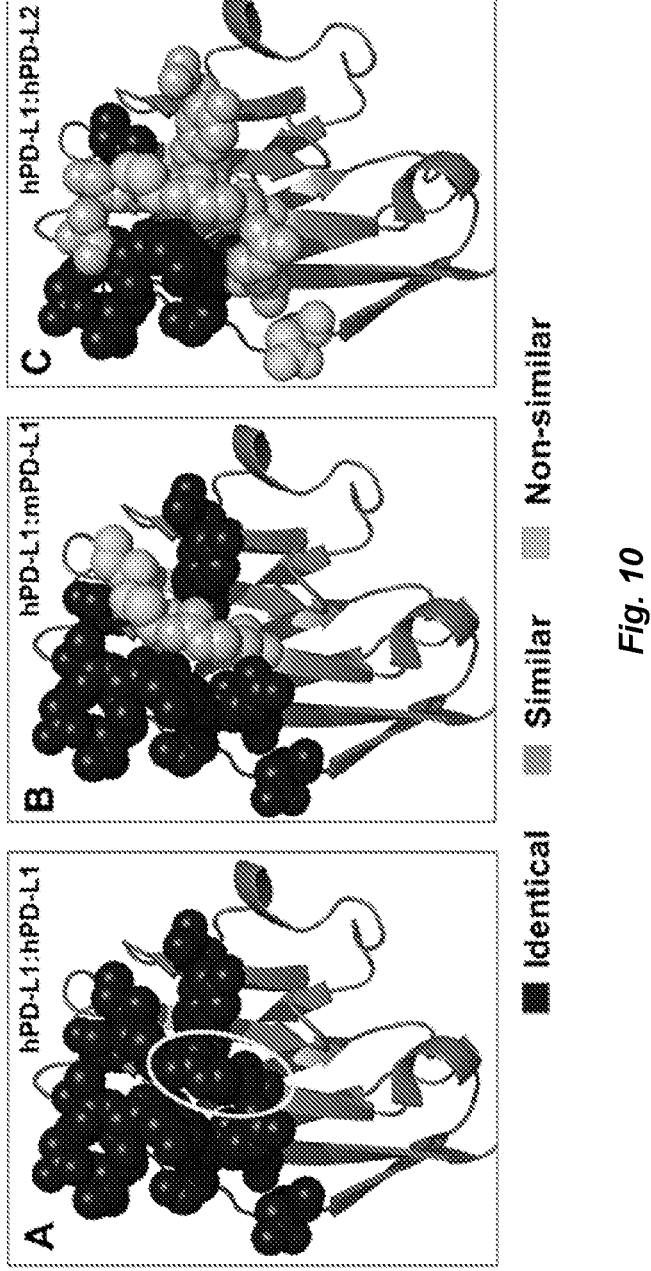

FIG. 10 illustrates conservation of binding site residues between hPD-L1, mPD-L1, and hPD-L2. A) Crystal structure of PD-L1 (3B1IS) showing the residues comprising the PD-1 binding site. Arg113 is circled. B) Structure of hPD-L1 showing conservation of binding site residues between hPD-L1 and mPD-L1. C) Structure of hPD-L1 showing conservation of binding site residues between hPD-L1 and hPD-L2. D) hPD-L1 binding pocket residues compared to the corresponding residues in mPD-L1 and hPD-L2. The conserved residues have no underlining, similar residues are boxed, and non-similar residues are underlined.

Figures 10, 11:
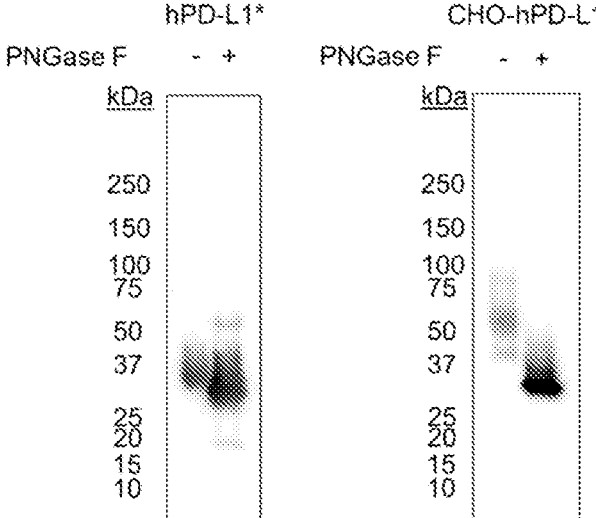

FIG. 11 illustrates PNGase F treatment confirms N-glycosylation of PD-L1 proteins. Recombinant hPD-L1* (left) and CHO-hPD-L1 lysates (right) were treated with Rapid PNGase F and western blotted. Band shifts indicate removal of N-linked glycans.

Figure 12:
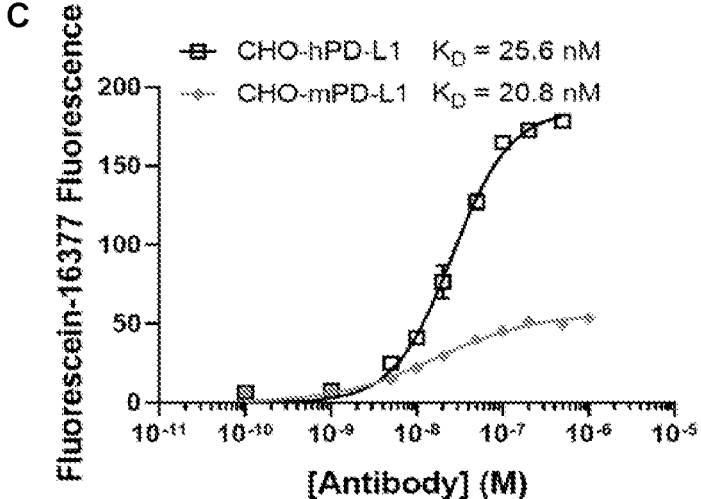

FIG. 12 illustrates binding affinity of Fluorescein-conjugated anti-PD-L1 antibodies. A) Titration of Fluorescein-Atezolizumab (black circles) and Fluorescein-Avelumab (grey squares) against CHO-hPD-L1 cells by flow cytometry. B) Titration of Fluorescein-16373 in CHO-hPD-L1

(squares) and CHO-mPD-L1 (diamonds) cells by flow cytometry. C) Titration of Fluorescein-16373 in CHO-hPD-L1 (squares) and CHO-mPD-L1 (diamonds) cells by flow cytometry. Curves represent one-site total binding calculated by GraphPad Prism.

Figure 13:
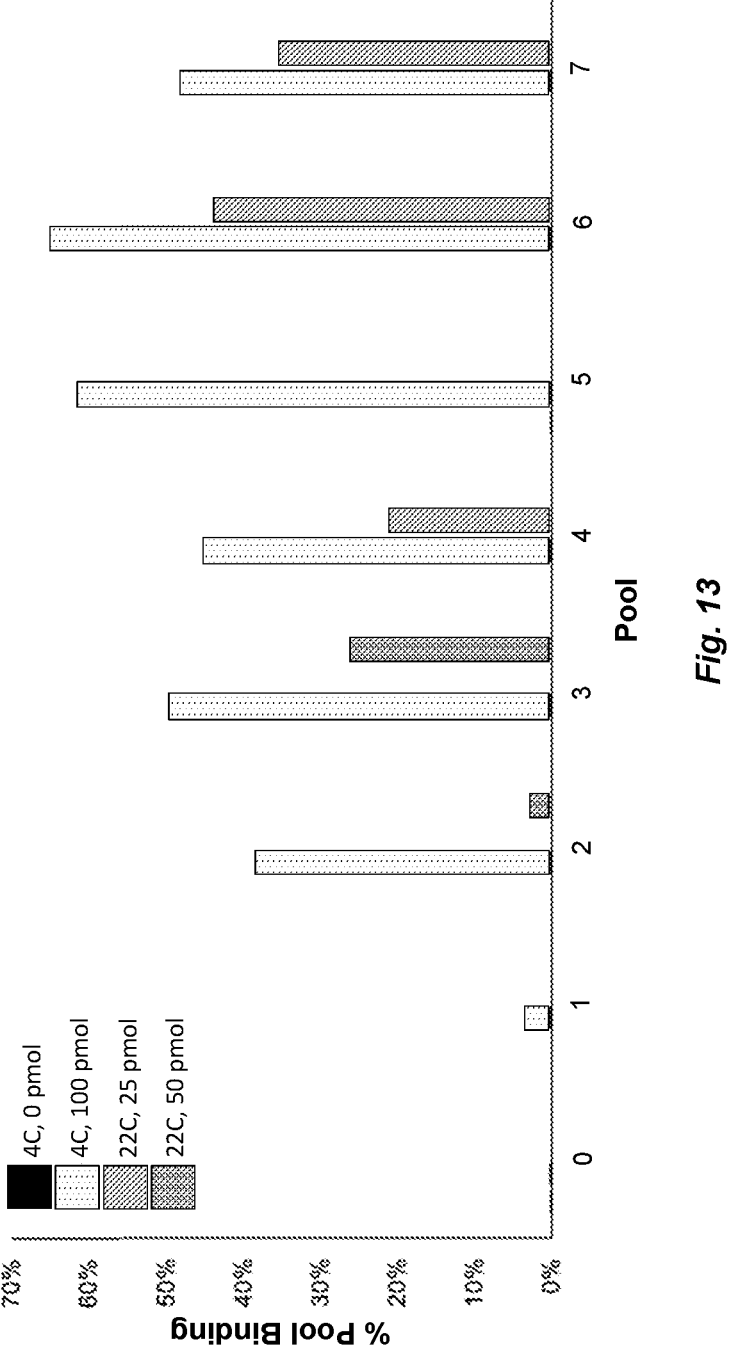

FIG. 13 illustrates binding percent of $^{35}$S-labeled mRNA-peptide fusions against immobilized human PD-L1 for generation of second-generation SPAM peptides. Each pool in the selection was tested for binding against beads containing 100 pmol of hPD-L1 or beads with no target at 4° C. No appreciable bead only binding is observed. Binding was also tested against reduced concentrations of hPD-L1, either at 25 pmol or at 50 pmol.

Figure 14:
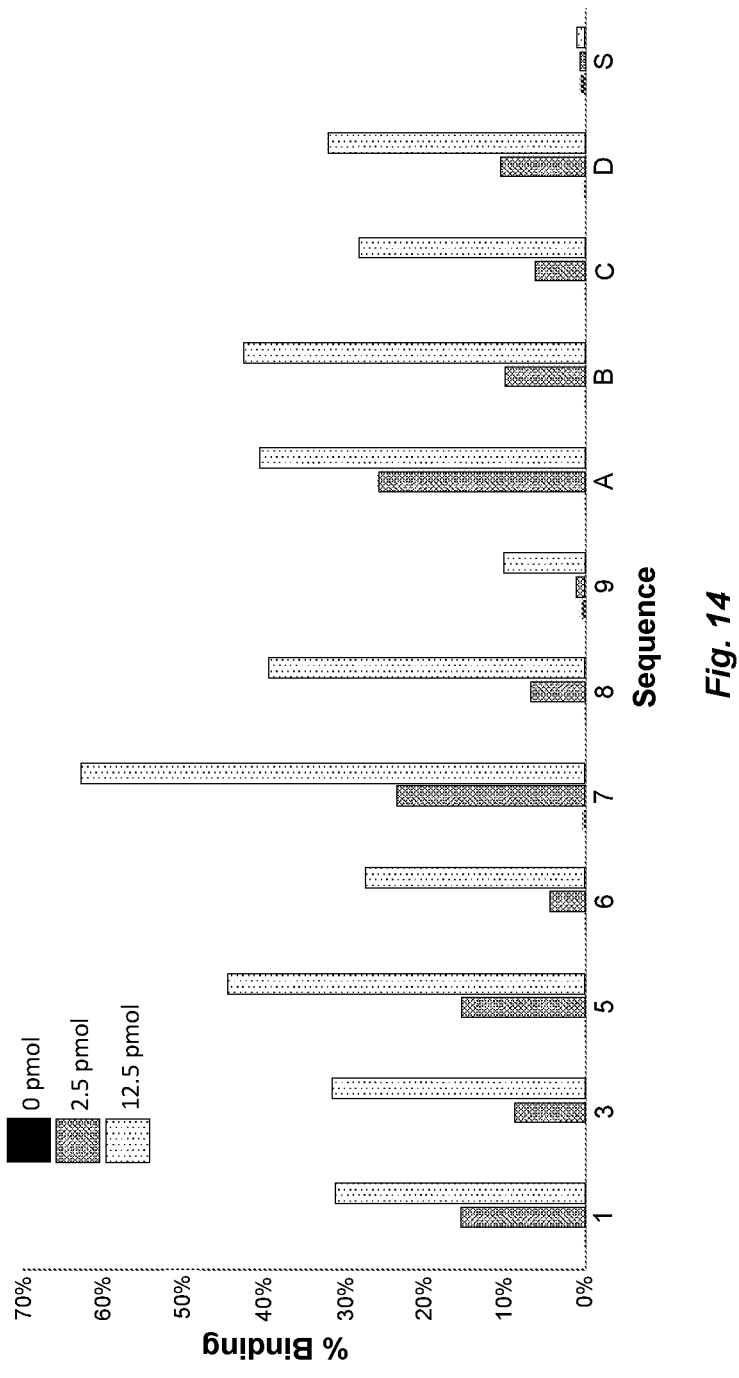

FIG. 14 illustrates Binding of Second-Generation Clones. Sequences from Illumina sequencing (Clones 1, 3, 5, 6, 7, 8, or 9) or from Sanger sequencing (A, B, C, D) of the second-generation library and first-generation SPAM peptide (S) were tested for binding to either 2.5 pmol or 12.5 pmol of immobilized human PD-L1. All peptides tested show better binding than the parental SPAM (S) sequence. No binding as observed against the negative control beads containing no PD-L1.

Figure 15:
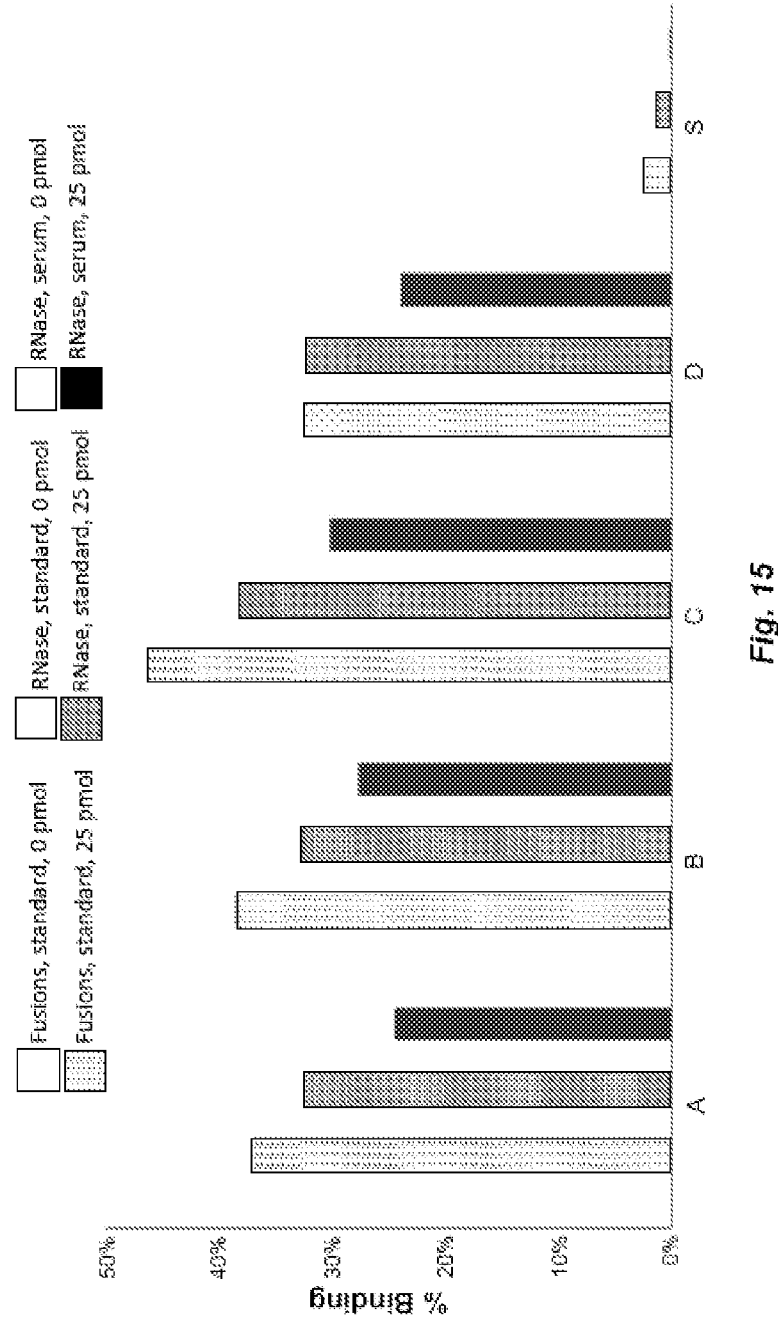

FIG. 15 illustrates resistance to degradation by human serum. Radiolabeled peptides A, B, C, D, and S were tested for binding against 25 pmol of hPD-L1. Fusions were also treated with RNase before binding to remove the mRNA portion. Fusions were also treated with RNase followed by incubation in human serum during binding. Peptides A, B, C, and D all show binding after incubation with RNase, indicating that the binding is due to the peptide portion of the fusions and not the mRNA portion. These peptides also show binding after incubation with human serum, showing that proteases and other enzymes in human serum do not significantly degrade these peptides.

DETAILED DESCRIPTION

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. An appropriate "effective" amount in any individual case may be determined using techniques, such as a dose escalation study.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. As such, the term "treatment" can include medical and therapeutic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93% or 94%, or even 95%, 96%, 97% 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)), or by computerized implementations of these algorithms (GAP, BESTFIT, FASTA, and TFASTA in, for example, the Wisconsin Genetics Software Package, Genetics Computer Group, 575 Science Dr., Madison, Wis.), or by inspection. An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, the invention also provides nucleic acid molecules and peptides that are substantially identical to the nucleic acid molecules and peptides presented herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Embodiments of the Invention

Antibodies are suboptimal for applications requiring tumor penetration or for imaging experiments and other applications requiring fast clearance from the body. The large size of antibodies and long serum half-lives are inherent antibody properties that confer these suboptimal qualities. Several studies showed slow uptake, poor penetration and poor distribution of trastuzumab, a monoclonal antibody, in solid tumors (Dennis, et al. (2007) Cancer Res 67: 254-61, Lee, et al. (2010) BMC Cancer 10: 255). In order to compensate for these deficiencies, larger amounts of compound and/or longer incubation periods must be used to obtain sufficient tumor uptake and penetration. Both of these options are suboptimal for many applications. For example, for therapeutic use, addition of more compound can cause toxicity and unacceptable side effects. In the case of imaging, longer incubation periods would cause more exposure to radiation in PET imaging experiments.

Antibodies also have long serum half-lives on the order of days to weeks. Trastuzumab has a serum half-life of about six days. While a long serum half-life may be desirable for an antibody therapeutic, it is a disadvantage for targeted radiotherapy or for PET imaging experiments since circulating radionuclide-labeled molecules nonselectively irradiate normal organs and tissue, including the bone marrow, which can be fatal. With respect to therapy, long antibody serum half-lives reduce the therapeutic window and limit the amount of radiation that can be delivered to the tumor. For PET imaging, long serum half-lives can also result in unnecessary radiation exposure to normal tissue.

The small size of peptides, on the other hand, has a positive effect on tumor uptake. Tumor uptake is a complex function of molecule size, vascular permeability, affinity, diffusibility, stability, and plasma clearance. For example, a comparison of Her2 ligands of vastly differing molecular weights demonstrated that the size of the tumor-targeting agent affects tumor uptake. Compounds with low effective molecular weight (e.g., affibodies and peptides) had high tumor uptake because of their ability to better diffuse and distribute within a tumor. High molecular weight compounds (e.g., antibodies) also showed high tumor uptake because of high binding affinities and long circulation times. Intermediate molecular weight compounds (e.g., Fab fragments and single chain antibodies) are predicted to have the worst tumor uptake as they combine poor tumor diffusion/distribution relative to smaller molecules with faster clearance from the body relative to larger molecules. This study predicts that as the size of the molecule is further reduced, tumor uptake will continue to increase.

Peptides thus have significant advantages over antibodies in situations where diffusion into a tumor or tissue is necessary, or in situations where fast clearance from the body is required. Peptides are significantly smaller than other molecules (e.g., $\frac{1}{100}^{th}$ the molecular weight of a monoclonal antibody) and are effectively the limit of how small an antibody can be reduced to. As a result, peptides are expected to have pharmacokinetics that are very different from monoclonal antibodies and combine the advantages of small molecules with those of antibodies: Like an antibody, peptides can be designed to target a protein of interest with high binding affinities, while at the same time retaining the small size, tumor distribution, and tumor diffusibility of small molecules.

Programmed Death Ligand 1 (PD-L1) is a critical immune checkpoint ligand whose overexpression on tumor cells provides a mechanism of escape from immune surveillance. The interaction between PD-L1 and PD-1 on T cell lymphocytes suppresses both T cell activation and effector function and is engaged by cancers to dampen anti-tumor immunity. Here, we used mRNA display to engineer an 18-residue linear peptide that binds to human PD-L1. This peptide, which we term SPAM (Signal Peptide based Affinity Maturated ligand), is non-homologous to known PD-L1 binding peptides and mAbs, with dissociation constants ($K_D$) of 119 nM and 67 nM for unglycosylated and glycosylated human PD-L1, respectively. The SPAM peptide is highly selective for human PD-L1 and shows no significant binding to either mouse PD-L1 or human PD-L2. Competition binding assays indicate that the SPAM peptide binding site overlaps with the binding site of PD-1 as well as therapeutic anti-PD-L1 antibodies. The SPAM peptide also was used as a basis for identifying second generation PD-L1 binding peptides. Taken together, these results suggest that the SPAM peptide and second-generation peptides specifically binds to human PD-L1 and could potentially serve as a PD-L1 affinity agent and PD-L1/PD-1 pathway modulator.

Accordingly, the disclosure provides for peptides that specifically bind to PD-L1, and compositions and methods of use thereof. In certain embodiments, a peptide that specifically binds to PD-L1 comprises the sequence M-$X_1$-$X_2$-$X_3$-$X_4$-D-H-$X_5$-L-N-K-F-$X_6$-I-$X_7$-H-X-$X_9$-$X_{10}$-$X_{11}$-$X_{12}$-$X_{13}$ (SEQ ID NO: 170), where: $X_1$ is E, F, K, W, or Y; $X_2$ is F, H, K, S, or T; $X_3$ is D, H, K, L, I, N, Q, R, S, or T; $X_4$ is A, F, S, N, V, or T; $X_5$ is I, N, S, T, or V; $X_6$ is F, L, I, W, or Y; $X_7$ is L or M; $X_8$ is E, F, N, Q, or Y; $X_9$ is A,S, or T; $X_{10}$ is A, F, H, I, K, L, M, N, Q, R, S, T, orV; $X_{11}$ is H, K, L, N, Q, R, S, T, or Y; $X_{12}$ is A, G, H, K, N, P, Q, R, S, or T; and $X_{13}$ is A, D, F, G, I, K, L, N, Q, M, S, or T.

In another embodiment, the PD-L1 binding peptide comprises an amino acid sequence of M-$X_1$-$X_2$-$X_3$-$X_4$-D-H-$X_5$-L-N-K-F-$X_6$-I-$X_7$-H-X-$X_9$-$X_{10}$-$X_{11}$-$X_{12}$-$X_{13}$ (SEQ ID NO: 171), wherein: $X_1$ is E, K, W, or Y; $X_2$ is F, H, S, or T; $X_3$ is D, Q, L, S, R, H, T, or I; $X_4$ is A, S, N, V, or T; $X_5$ is I, N, S, T, or V; $X_6$ is F, L, I, W, or Y; $X_7$ is L or M; $X_8$ is E, F, Q, or Y; $X_9$ is A, S, or T; $X_{10}$ is A, F, L, N, R, T, or V; $X_8$ is N, Q, or K; $X_{12}$ is H, P, Q, or S; and $X_{13}$ is F, G, N, Q, M, S, or T.

In another embodiment, the PD-L1 binding peptide has an amino acid sequence consisting of M-$X_1$-$X_2$-$X_3$-$X_4$-D-H-$X_5$-L-N-K-F-$X_6$-I-$X_7$-H-$X_8$-$X_9$-$X_{10}$-$X_{11}$-$X_{12}$-$X_{13}$ (SEQ ID NO: 171), wherein: $X_1$ is E, K, W, or Y; $X_2$ is F, H, S, or T; $X_3$ is D, Q, L, S, R, H, T, or I; $X_4$ is A, S, N, V, or T; $X_5$ is I, N, S, T, or V; $X_6$ is F, L, I, W, or Y; $X_7$ is L or M; $X_8$ is E, F, Q, or Y; $X_9$ is A, S, or T; $X_{10}$ is A, F, L, N, R, T, or V; $X_8$ is N, Q, or K; $X_{12}$ is H, P, Q, or S; and $X_{13}$ is F, G, N, Q, M, S, or T.

In other embodiments, the PD-L1 binding peptide has an amino acid sequence at least 75%, at least 80%, at least 85%, at least 90%, or at least 95% identical to one or more of SEQ ID NOs: 141-151. In other embodiments, the peptide that specifically binds to PD-L1 has an amino acid of any one of SEQ ID NOs: 141-151. In still further embodiments, the PD-L1 binding peptide has an amino acid sequence consisting of any one of SEQ ID NOs: 141-151.

In other embodiments, the PD-L1 binding peptide has the amino acid sequence MXIFπXXIXXXQWXLXXA (SEQ ID NO: 1), where 71 represents an aliphatic amino acid, X represents any amino acid, and Q represents an aromatic amino acid. In some embodiments, the peptide has at least 80%, at least 85%, at least 90%, or at least 95% similarity to MPIFLDHILNKFWILHYA (SEQ ID NO: 3). In other embodiments, the peptide is SEQ ID NO: 3. In other embodiments, the peptide is MIFLDHILNKFWILHYA (SEQ ID NO: 4), MFLDHILNKFWILHYA (SEQ ID NO: 5), MLDHILNKFWILHYA (SEQ ID NO: 6), or MDHILNKFWILHYA (SEQ ID NO: 7).

In some embodiments, the PD-L1 binding peptide competitively inhibits binding of one or more of WL12 (a macrocyclic hPD-L1 inhibitor peptide), Atezolizumab (an hPD-L1 specific monoclonal antibody), and mPD-1 (the murine variant of PD-1).

It is anticipated that one or more amino acid substitution, insertion, or deletion may be made to a peptide of the present invention without substantially reducing or eliminating the ability of the peptide to impart atherapeutic effect, such as promoting wound healing or reducing inflammation, in a subject. Protein variants and derivatives are contemplated for use with the present invention and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions typically involve smaller insertions than those of amino or carboxyl terminal fusions, for example, an insertion of one to four amino acid residues. Deletions are characterized by the removal of one or more amino acid residues from the protein sequence. Variants may be prepared by site-specific mutagenesis of nucleotides in the DNA encoding the protein, thereby producing DNA encoding the variant, and thereafter expressing the DNA in recombinant cell culture. Alternately, variants may be produced by peptide synthesis. Techniques for making substitution mutations at predetermined sites in DNA having a known sequence are well known and include, for example, M13 primer mutagenesis and PCR mutagenesis. Amino acid substitutions typically involve mutation of single residues but may occur at a number of different locations at once, e.g., on 1, 2, 3, 4, or 5 amino acid residues. Deletions or insertions may be made in adjacent pairs, i.e., a deletion of 2 residues or an insertion of 2 residues. Substitutions, deletions, insertions, or any combination thereof can be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place.

For example, the replacement of one amino acid residue with another that is biologically and/or chemically similar is known to those skilled in the art as a conservative substitution. A conservative substitution may involve, e.g., replacing one hydrophobic residue for another hydrophobic residue, or one polar residue for another polar residue. Conservatively substituted variations of each explicitly disclosed sequence are included within the polypeptides provided herein.

Conservative substitutions may have little to no impact on the biological activity of a resulting polypeptide. In some embodiments, a conservative substitution in a peptide does not substantially affect the biological function of the peptide. A peptide can include one or more amino acid substitutions, for example 2-10 conservative substitutions, 2-5 conservative substitutions, 4-9 conservative substitutions, or 1, 2, 3, 4, 5 or 10 conservative substitutions.

Conservative substitutions can be introduced into a peptide sequence by known methods such as, e.g., site-directed mutagenesis or PCR. Alternatively, a polypeptide can be produced to contain one or more conservative substitutions by using standard peptide synthesis methods. An alanine scan may be used to identify which amino acid residues in a protein can tolerate an amino acid substitution. In one example, the biological activity of the protein is not decreased by more than 25%, for example not more than 20%, for example not more than 10%, when an alanine, or other conservative amino acid, is substituted for one or more native amino acids. Further information about conservative substitutions can be found in standard textbooks of genetics and molecular biology.

Substitutional or deletional mutagenesis may be employed to insert sites for N-glycosylation (Asn-X-Thr/Ser) or O-glycosylation (Ser or Thr). Deletions of cysteine or other labile residues may be performed. Deletions or substitutions of potential proteolysis sites, e.g., Arg, may be accomplished for example by deleting one of the basic residues or substituting one by glutaminyl or histidyl residues.

Certain post-translational derivatizations may result from expression of a peptide of the present invention in recombinant host cells. Glutaminyl and asparaginyl residues are frequently post-translationally deamidated to the corresponding glutamyl and asparyl residues. Alternatively, these residues may be deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains, acetylation of the N-terminal amine and, in some instances, amidation of the carboxyl-terminal.

It also is understood in the art that the substitution of like amino acids can be made effectively on the basis of hydrophilicity, particularly where the biological functional equivalent protein and/or peptide thereby created is intended for use in therapeutic or immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

In some embodiments, a PD-L1 binding peptide of the present disclosure may be conjugated to another molecule, or secondary molecule. This secondary molecule can be, for example, a small diagnostic molecule such as a fluorescent dye (e.g., fluorescein, rhodamine, Cy5, etc.), a chelator (e.g., 1,4,7,10-Tetraazacyclododecane-1,4,7,10-tetraacetic acid (DOTA), S-2-(4-Isothiocyanatobenzyl)-1,4,7,10-tetraaza-1, 4,7,10-tetra(2-carbamoylmethyl)cyclododecane (p-SCN-Bn-TCMC), 1,4,8,11-Tetraazabicyclo[6.6.2]hexadecane-4, 11-diacetic acid (CB-TE2A), 1,8-Diamino-3,6,10,13,16,19-hexaazabicyclo[6,6,6]-eicosane (DiAmSar), 1,4,8,11-Tetraazacyclotetradecane-1,4,8,11-tetraacetic acid (TETA), etc.), a radioactive nuclide (e.g., $^{18}$F, $^{64}$Cu, $^{67}$Cu, $^{86}$Y $^{90}$Y, etc.), biotin, streptavidin, avidin, or a label for magnetic resonance imaging.

In other embodiments, the secondary molecule is a peptide sequence that is recognized by an antibody (e.g., FLAG, HA, myc tags).

In other embodiments, the secondary molecule is a protein such as green fluorescent protein (GFP), a GFP derivative, maltose binding protein, or glutathione S-transferase.

In other embodiments, the secondary molecule is a reporter enzyme such as horseradish peroxidase, alkaline phosphatase, beta-galactosidase, or acetylcholinesterase.

In other embodiments, the secondary molecule is another peptide or protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor There are many known ways of attaching or conjugating these molecules to the PD-L1 binding peptide. One method includes chemical modification of the peptides with the required secondary molecule. This modification can be performed during the synthesis of the peptide, for example, using a secondary molecule that contains a carboxylic acid that can be used to form an amide bond with the peptide through standard peptide synthesis reagents (e.g., the addition of 1-[Bis(dimethylamino)methylene]-1H-1,2,3-triazolo[4,5-b]pyridinium 3-oxide hexafluoro-phosphate (HATU) with N,N-Diisopropylethylamine (DIEA) in the presence of a carboxylic acid). Alternatively, the modification can be added using a secondary molecule that contains a primary or secondary amine with a carboxylic group on the peptide using similar peptide synthesis reagents.

A secondary molecule also can be added post-synthetically to the PD-L1 binding peptide. For example, the peptide can be synthesized with a group that can react specifically with another group on the secondary molecule. One preferred embodiment is the addition of an alkyne- or azide-containing amino acid to the peptide, which can be specifically conjugated to an azide- or alkyne group (respectively) on the secondary molecule using copper catalyzed azide-alkyne cycloaddition (CuAAC) (Himo, et al. (2005) J Am Chem Soc 127: 210$^{-6}$, Worrell, et al. (2013) Science 340: 457-60) or "click" chemistry. An alternative method is using "copper-free" click chemistry using a strained octyne (Chang, et al. (2010) Proc Natl Acad Sci USA 107: 1821-6) or Dibenzocyclooctyne (Ning, et al. (2008) Angew Chem Int Ed Engl 47: 2253-5).

Other methods of post-synthetically modifying peptides are well known in the art. These include the use of N-hydroxysuccinimide (NHS) esters, malemides, iodoacetamides, isothiocyanides, pentafluoro esters, through an oxime ligation (Decostaire, et al. (2014) Org Biomol Chem 12: 5536-43), or through native ligation (Dawson (1994) Science 266: 776-9).

In other embodiments, the secondary molecule may be one or more drugs or cytotoxic agents where the PD-L1 binding peptide is conjugated to the drug or cytotoxin, and the peptide allows PD-L1-specific delivery of the conjugated molecule. The advantage of this method is that a molecule that would be too toxic for general administration could be directed to be more specifically delivered to a tumor or tissue, thereby limiting unwanted non-selective side effects. Another advantage of using a peptide to deliver a toxin is that a peptide-conjugate will generally have shorter serum half-life as compared with an antibody. In cases where a peptide-conjugate causes unwanted side effects, rapid systemic clearance, characteristic of peptides, allows a greater safety window: stopping administration of the conjugate will result in clearance from the body. This is in contrast to antibodies, where week-long half-lives mean that a toxic antibody conjugate will remain in the body much longer, possibly causing greater damage. Exemplary cytoxic agents for use with the peptides described herein include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Other agents which have a potential therapeutic benefit include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromo-mannitol, streptozotocin, mitomycin C, and cisdichlorodi-amine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), maytansinoids and anti-mitotic agents (e.g., vincristine and vinblastine).

In other embodiments, the PD-L1 binding peptides can be used for treatment of solid tumors by delivery of radiation to the tumor. The peptides will allow specific delivery of radionuclides, thereby targeting the delivery of radiation to solid tumors. There are several advantages of targeted radiotherapy using peptides as delivery agents. Delivery of radiation can address tumor heterogeneity as the "crossfire effect" can result in related cells in a tumor being killed, even if they do not express PD-L1 on the cell surface (Read, et al. (2015) Target Oncol 10: 15-26). Radiotherapy can also kill cells vs. inhibition of a signaling pathway, which may result in slowing of tumor growth. As a result, there is little chance for malignant cells to develop resistance. Targeted radiotherapy can also be combined with other chemotherapeutics that can help to radiosensitize tumors, creating a synergistic effect.

The radionuclides that are delivered by the peptide can be α-, β-, or γ-emitters. Examples of such radionuclides include, but are not limited to: $^{90}$Y, $^{131}$I, $^{177}$Lu, $^{153}$Sm, $^{186}$Re, $^{188}$Re, $^{67}$Cu, $^{225}$Ac, $^{213}$Bi, $^{212}$Bi, $^{211}$At, $^{212}$Pb, $^{125}$I. In a preferred embodiment, the radionuclide will be an α-emitter as α-emitters have a short range of effect, that can limit damage to non-malignant tissue, but can also transfer high amounts of energy to kill tumor cells (Poty, et al. (2018) J Nucl Med 59: 878-884).

Addition of the radionuclide will be accomplished through conjugation of a secondary molecule that can bind to radionuclides as described above. In a preferred embodiment, this secondary molecule will be a chelator, e.g., DOTA, that has high affinity for these radionuclides. High affinity is important to avoid loss ofthe radionuclide in the body by either dissociation ofthe radionuclide or events such as transchelation that can occur in the liver.

In another embodiments, the PD-L1 binding peptides may be used for detection of the PD-L1 receptor in in vivo imaging techniques. Commonly used imaging techniques involve magnetic resonance (MR), positron emission tomography (PET), or fluorescence imaging. For these uses, an appropriate secondary molecule will be conjugated to allow imaging via the desired modality; for example, in PET imaging a $^{18}F$ can be conjugated to the peptide using methods well known in the art (Pisaneschi, et al. (2017) Bioconjug Chem 28: 583-589). In the case of fluorescence imaging, an appropriate fluorescent label, e.g., Cy5, can be used.

In a preferred embodiment, a PET label is $^{18}F$ because of its relatively short half-life (~2 h) that allows for fast, one-day imaging experiments to be possible. A peptide conjugated to $^{18}F$ can allow for one-day imaging—if a peptide has a relatively short half-life in an organism (e.g., <2 h), an imaging experiment can be performed within a few hours after injection of a radiotracer. This is because after injection of a peptide radiotracer, unbound radiotracer can clear the body quickly, reducing the background signal, and allowing the bound peptide radiotracer to be imaged. This is in contrast with an antibody, which has a long-serum half-life (~weeks) which means that an imaging experiment can only be performed days after a radiotracer.

In another embodiment, the PD-L1 binding peptides can be used to detect the presence of PD-L1 in tissue samples. In pathology, detection of the presence, absence, and/or level of PD-L1 can be used to predict response to anti-PD-L1 therapy. For example, the Agilent Dako PD-L1 IHC 28-8 pharmDx kit can be used to detect the presence of PD-L1 in formalin-fixed paraffin-embedded samples for non-small cell lung cancer, squamous cell carcinoma of the head and neck, and urothelial carcinoma (Koppel, et al. (2018) Mod Pathol 31: 1630-1644).

Preferably, embodiments may use a PD-L1 binding peptide conjugated to a secondary molecule that enables a signal to be generated. For example, addition of biotin can allow detection by streptavidin-horseradish peroxidase (HRP) or streptavidin-alkaline phosphatase (AP), which are commonly used in the art for immunohistochemical detection (IHC). In another embodiment, a fluorescent label is conjugated to the peptide, allowing detection of a bound molecule by fluorescence detection.

Embodiments of the disclosure may be used to identify and/or treat certain disease states, such as cancer. Many types of cancer express PD-L1 including renal cell carcinoma (RCC), non-small cell lung cancer (NSCLC), small cell lung cancer (SCLC), metastatic Merkel cell carcinoma, bladder, head and neck, cervical, urothelial, glioblastoma multiforme, breast, triple-negative breast, gastric, esophageal, hepatocellular carcinoma, pancreatic, colorectal, thymic, ovarian, sarcoma, acute myeloid leukemia, various leukemia, B-cell lymphomas, and multiple myeloma.

Results and Discussion

As described herein, a small peptide with high affinity and high specificity for hPD-L1 (MRIFAVFIFMTYWHLLNAF-TVTVPKDLYVVEYGSNMTIECKFPVEKQLDLAAL-IVYWEMEDKNI IQFVH-GEEDLKVQHSSYRQRARLLKDQLSLGNAALQITDV-KLQDAGVYRCMISYGGADYKRITV KVNAPYNKINQRILVVDPVTSEHELTCQAEGYP-KAEVIWTSSDHQVLSGKTTTTNSKREEKLFNV TSTL-RINTTTNEIFYCTFRRLDPEENHTAELVIPELPLAHPP-NERTHLVILGAILLCLGVALTFIFRLR KGRMMDVKKCGIQDTNSKKQSDTHLEET (SEQ ID NO:25)) has been identified. In order to generate purified target for immobilization and selection, the extracellular domain of hPD-L1 (from A18 to T239) (AFTVTVPKDLY-VVEYGSNMTIECKFPVEKQLDLAALIVY- WEMEDKNIIQFVHGEEDLKVQHSSY RQRARLLKDQLSLGNAALQITDVKLQDAGVYRCMI-SYGGADYKRITVKVNAPYNKINQRILVVD PVTSEH-ELTCQAEGYP-KAEVIWTSSDHQVLSGKTTTTNSKREEKLFNVTSTL-RINTTTNEIFYCTFR RLDPEENHTAELVIPELPLAHPP-NERT (SEQ ID NO:26)) was expressed in *E. coli*. The protein contained an Avi tag at the C-terminus which was enzymatically biotinylated with the BirA biotin ligase. The biotinylated hPD-L1 was then purified using affinity chromatography and ion exchange chromatography and immobilized on neutravidin or streptavidin beads for selection purposes (FIG. 1A).

In order to confirm that the expressed hPD-L1 was correctly folded, binding to mPD-1 was measured by SPR. The dissociation constant ($K_D$) between recombinant hPD-L1 and PD-1 was determined to be 3.2±0.3 µM using a one-site saturation binding model (FIG. 7). This value is consistent with previously reported $K_D$ values ($K_D \approx 4$ to 8 µM), indicating that the recombinant E. col-expressed hPD-L1 is correctly folded and functional.

Primary Selection with an $X_9$ Library

A primary selection was performed using a random $X_9$ DNA library consisting of an open reading frame coding for nine random amino acids. The amplified DNA library was transcribed into corresponding mRNA library and ligated to a puromycin-bearing oligonucleotide. The resulting library template was translated, purified, reverse transcribed, and incubated with immobilized hPD-L1. After extensive washing, bound sequences were amplified by PCR to generate the full-length DNA library for the next selection cycle (FIG. 1B). After five rounds of selection, the binding of the library to immobilized hPD-L1 increased dramatically over background (FIG. 8A), suggesting enrichment of target-binding peptide sequences. The round 6 pool was analyzed by next generation sequencing and the clones with highest frequency were identified. One of these peptides, MRIFVIFIWA (SEQ ID NO: 27), designated as clone 1 was highly represented in the round 6 pool (Table 1). Using the Basic Local Alignment Search Tool (BLAST), we identified regions of local similarity between clone 1 and the first 10 amino acids of the hPD-L1 signal peptide (60% identity, 90% homology). This unexpected similarity prompted us to perform a maturation selection with a doped library based on the hPD-L1 signal peptide sequence.

Maturation Selection and Identification of the SPAM Peptide

To enhance the affinity and selectivity of the peptide selected from the $X_9$ library, we designed a doped library based on the wild type hPD-L1 signal peptide sequence. This library, termed $X_{17}$, was constructed such that each nucleotide was doped at a 70% probability wild type frequency (and 10% of each of the other three nucleotides), which results in an average frequency of ~44% wild-type amino acid at each position in peptide sequence (FIG. 1C). The hPD-L1 signal peptide itself shows some binding to streptavidin agarose beads loaded with 1.1 µM hPD-L1 (equivalent to 1,100 pmol of hPD-L1) (FIG. 8). We performed eight rounds of selection for hPD-L1 binding using the $X_{17}$ library, with significant target-specific binding emerging after round 5 (FIG. 7B). Target-specific binding continued to increase in subsequent rounds even as additional selective pressure was added by increasing the binding temperature from 4° C. to room temperature. MPIFL-DHILNKFWILHYA (SEQ ID NO: 3) was identified as the most frequently occurring sequence by next-generation sequencing and designated as Signal Peptide-based Affinity Matured ligand (SPAM) peptide. The SPAM peptide was 33% identical to the hPD-L1 signal peptide and showed a consensus motif of MXIFπXXIXXXQWXLXXA (SEQ ID NO: 1), where 71 represents an aliphatic amino acid, X represents any amino acid, and Q represents an aromatic amino acid (Table 1).

TABLE 1

Selected peptides sequences. The initial X9 library selection resulted in a clone with significant homology to the first nine residues of the hPD-L1 signal peptide. The PD-L1 signal peptide sequence was used to design the X17 library (doped at ~70% wild type at the DNA level) from which the SPAM peptide was selected. Residues that are identical between the hPD-L1 signal peptide and the selected peptides are shown in bold. The grand average of hydropathy (GRAVY Index) for the peptide sequences are calculated as the ratio of the sum of the hydropathy index of each amino acid in a sequence to the peptide length.

| Peptide | Sequence | GRAVY Index |
|---|---|---|
| hPD-L1 signal peptide | MRIFAVFIF MTYWHLLNA (SEQ ID NO: 2) | 1.25 |
| Clone 1: Selected clone from X9 library | MRIFVIFIWA (SEQ ID NO: 27) | 2.16 |
| SPAM: Selected clone from X17 library | MPIFLDHIL NKFWILHYA (SEQ ID NO: 3) | 0.73 |

The SPAM Peptide Binds to hPD-L1 with Mid-Nanomolar Affinity. To evaluate the affinity of SPAM for hPD-L1 and hPD-L1*, we measured the $K_D$ by fluorescence polarization. ROX-labeled SPAM (ROX-SPAM) was incubated with increasing concentrations of hPD-L1 or hPD-L1* and the fluorescence polarization of the ROX fluorophore measured at excitation and emission wavelengths of 540 nm and 620 nm, respectively. The resulting values were plotted against the concentration of hPD-L1 or hPD-L1* and fit to a one-site saturation binding model with GraphPad Prism. ROX-SPAM was found to bind hPD-L1 with a dissociation constant ($K_D$) of 119±33 nM (T=21° C.) and hPD-L1* with a $K_D$ of 67 i 21 nM (T=22° C.) (FIGS. 2A and 2B). This affinity is significantly better than the micromolar $K_D$ between PD-1 and hPD-L1 and is higher than a variety of previously reported peptides targeting hPD-L1. Although SPAM shows a weaker affinity relative to WL12, it has the advantage of being a linear peptide with only natural residues, which makes it easier to chemically synthesize or express recombinantly inside cells.

SPAM Peptide Selectively Binds to hPD-L1. SPAM was also tested for binding specificity towards mouse PD-L1 (mPD-L1) and human PD-L2 (hPD-L2) using radioactive binding assays. SPAM peptide mRNA was translated in vitro in the presence of [$^{35}$S]-methionine to generate [$^{35}$S]-labeled SPAM peptide. Radiolabeled SPAM peptide was efficiently pulled-down by hPD-L1 immobilized on streptavidin agarose but was not pulled-down by mPD-L1 (FIG. 2C). [$^{35}$S]-SPAM peptide was also captured by hPD-L1* (FIG. 2D), although no significant binding to hPD-L2* was observed (FIGS. 2D and 2E). These data demonstrate that SPAM binds tightly to both glycosylated and non-glycosylated forms of hPD-L1 yet shows essentially no binding to mPD-L1 or hPD-L2 despite 77% and 34% homology to hPD-L1, respectively. SPAM therefore displays hPD-L1 specific binding, which is an important feature as compared with previously reported peptides that are not as hPD-L1 specific (Table 2).

TABLE 2

Comparing SPAM and known peptides regarding their binding properties for hPD-L1.

| Peptide Name | Sequence | $K_D$, IC50, EC50 (nM) |
|---|---|---|
| SPAM | MPIFLDHILNKFWILHYA (SEQ ID NO: 3) | $K_D$ = 67-119 |
| Peptide-57 | Cyclo[(AcPhe)NMeAla)NPHLSWSW(NMeNle)(NMeNle)RC]Gly-NH$_2$ (SEQ ID NO: 172) | EC50 = 566 IC50 = 9 |
| Peptide-71 | Cyclo[(AcPhe)(NMePhe)(NMeNle)(Sar)DV(NMePhe)Y(Sar)WYLC-Gly-NH$_2$ (SEQ ID NO: 173) | EC50 = 293 IC50 = 7 |
| Peptide-99 | Cyclo [(AcPhe)LIVIRDRVFRC]-Gly-NH$_2$ (SEQ ID NO: 174) | EC50 = 6300 IC50 = 153 |
| WL-12 | Cyclo[(AcTyr)(NMeAla)NPHL(Hyp)WS(Trp(Me))(NMeNle)(NMeNle)(Orn)C]-Gly-NH$_2$ (SEQ ID NO: 175) | IC50 ≈ 22-23 IC50 ≈ 2-6 |
| TPP-1 | SGQYASYHCWCWRDPGRSGGSK (SEQ ID NO: 160) | $K_D$ = 95 |

TABLE 2-continued

Comparing SPAM and known peptides regarding
their binding properties for hPD-L1.

| Peptide Name | Sequence | $K_D$, IC50, EC50 (nM) |
|---|---|---|
| CLP001 | HYPFRPHANQAS (SEQ ID NO: 161) | $K_D$ = 534<br>$IC_{50}$ = n/a |
| CLP002 | WHRSYYTWNLNT (SEQ ID NO: 162) | $K_D$ = 366 $IC_{50}$ = 2170 |
| CLP003 | WHFSYNWRWLPP (SEQ ID NO: 163) | $K_D$ = 117 $IC_{50}$ = 2220 |
| CLP004 | DYHDPSLPTLRK (SEQ ID NO: 164) | $K_D$ = 544<br>$IC_{50}$ = 1170 |
| P1 | SNQTDK (SEQ ID NO: 165) | — |
| D-PPA-1 | NYSKPTDRQYHF (SEQ ID NO: 166) (all D-amino acids) | $K_D$ = 510 |
| D-PPA-2 | KHAHHTHNLRLP (SEQ ID NO: 167) (all D-amino acids) | $K_D$ = 1130 |
| RK-10 | GSGSGSTYLCGAISLAPKAQIKESL (SEQ ID NO: 168) | — |
| Compound 8 | SNTSESFK(SNTSESF)FRVTQLAPKAQIKE-NH$_2$ (SEQ ID NO: 169, "SNTSESF" disclosed as SEQ ID NO: 182) | $EC_{50}$ < 50 |

The Stability of SPAM Peptide in the Presence of Human Serum

Several previously reported PD-L1 binding peptides have used cyclization and unnatural amino acids or D-amino acids in order to increase peptide stability in serum. As SPAM is a linear peptide composed of natural amino acids, it might therefore be susceptible to degradation by proteases in human serum. We performed two complementary assays to determine what effect serum has on the SPAM/hPD-L1 interaction. We first tested SPAM peptide stability by performing an HPLC-based assay to test if SPAM is degraded by human serum. We incubated ROX-labeled SPAM with 25% human serum at 37° C., took aliquots at different time points, then analyzed the products using HPLC. We observed no degradation even after five hours of incubation nor detected any change in peptide retention time (FIG. 2F), suggesting that the peptide was not modified by serum. We also tested to see if human serum had an effect on SPAM binding by incubating [$^{35}$S]-labeled SPAM with 25% human serum at 37° C., then measuring the binding to immobilized hPD-L1. No decrease in the binding was observed after two hours of incubation, but a slight decrease in the binding was observed after four hours of incubation (FIG. 2G). After eight hours of incubation, no further decrease was observed. Taken together, both assays support the conclusion that even though SPAM is a linear peptide with no unnatural amino acids, it is resistant to degradation against proteases in human serum. Previous work has shown that natural peptides can exhibit significant resistant to proteolysis and although SPAM was not subjected to an explicit proteolytic resistance selection, it nonetheless is resistant to proteolytic degradation by human serum. SPAM does show a small (~25%) but statistically significant loss of binding, however taken with the stability data above, this loss is unlikely to be due to proteolysis, but possibly some other modification that occurs in presence of human serum.

The C-terminal Residues of the SPAM Peptide are Critical for hPD-L1 Binding

Alanine scanning provides a framework for structure activity relationships and reveals core residues within peptides and proteins important for binding interactions. To determine the critical residues for the SPAM/hPD-L1 binding interaction, we translated a set of [$^{35}$S]-labeled SPAM peptides where each residue was individually substituted with alanine (FIG. 3A). We found that the 13A, F4A, L5A, 18A and L9A mutations had little or no significant influence on hPD-L1 binding, implying that these residues are not crucial for the SPAM affinity. P2A and Y18A variants showed decreased levels of hPD-L1 binding, although this did not reach the level of statistical significance. In contrast, the D6A, H7A, N10A, K11A, F12A, W13A, I14A, L15A, H16A, and A18 mutations completely abolished hPD-L1 binding, suggesting that these residues are critical for SPAM peptide affinity. Since the majority of these important residues are located in the C-terminal half of the peptide, these data indicate that the C-terminal portion of SPAM contributes more to hPD-L1 binding than the N-terminal portion.

We analyzed the next-generation sequencing results from the round 6 pool of the $X_{17}$ selection and measured the conservation of each amino acid residue relative to the SPAM peptide. Next generation sequencing results were first sorted into families and 108 sequences homologous to SPAM were binned and the percent identity to SPAM was determined (Table 3). This analysis allowed residues to be sorted into three groups, highly conserved (>950%), conserved (85-95%), and modestly conserved (<850%) (FIG. 3). Most positions that are associated with abolished binding in the alanine scanning experiment showed >950% conservation in high throughput screening.

TABLE 3

SPAM point mutants found in next generation sequencing data. Next generation
sequencing results were binned based on the family groups and 108 sequences
from SPAM family that were appearing more than 1,000 times in the sequencing
results were identified and were evaluated to see what percent were presenting
the same residue as SPAM at each position. Rank within the pool, peptide
sequence, the related copy number and the frequency of appearance calculated
as part per million (PPM) are illustrated for each sequence.
Variable residues are underlined.

| # | Sequence | Copy Number | PPM | SEQ ID NO: |
|---|----------|-------------|-----|------------|
| 1-SPAM | MPIFLDHILNKFWILHYAGSG | 3993923 | 517360.4 | 30 |
| 2 | MPIFLDHVLNKFWILHYAGSG | 196767 | 25488.6 | 31 |
| 3 | MPIFLDHTLNKFWILHYAGSG | 144786 | 18755.1 | 32 |
| 4 | MPISLDHILNKFWILHYAGSG | 126983 | 16449.0 | 33 |
| 5 | MRISVDHILLKFWILHNSGSG | 118033 | 15289.6 | 34 |
| 6 | MPILLDHILNKFWILHYAGSG | 93196 | 12072.3 | 35 |
| 7 | MPIFQDHILNKFWILHYAGSG | 41993 | 5439.6 | 36 |
| 8 | MPIFPDHILNKFWILHYAGSG | 38610 | 5001.4 | 37 |
| 9 | MPVFLDHILNKFWILHYAGSG | 26384 | 3417.7 | 38 |
| 10 | MGTFYDHIFIKFMILHTTGSG | 24332 | 3151.9 | 39 |
| 11 | MPIYLDHILNKFWILHYAGSG | 23595 | 3056.4 | 40 |
| 12 | MPIFIDHILNKFWILHYAGSG | 21873 | 2833.4 | 41 |
| 13 | MPMFLDHILNKFWILHYAGSG | 21626 | 2801.4 | 42 |
| 14 | MRKSVDHILLKFWILHNSGSG | 19680 | 2549.3 | 43 |
| 15 | MPTFLDHILNKFWILHYAGSG | 19624 | 2542.0 | 44 |
| 16 | MPIFLDHMLNKFWILHYAGSG | 19220 | 2489.7 | 45 |
| 17 | MGTFYDHIFIKFMILHTAGSG | 18109 | 2345.8 | 46 |
| 18 | MPIFLDHILNKFWILHHAGSG | 18060 | 2339.4 | 47 |
| 19 | MPIFLDHILNKFWILHCAGSG | 17837 | 2310.5 | 48 |
| 20 | MKKFSDHTLMKFWILVNAGSG | 17366 | 2249.5 | 49 |
| 21 | MPIFLDHILNKFRILHYAGSG | 16647 | 2156.4 | 50 |
| 22 | MPIFLDHILSKFWILHYAGSG | 16162 | 2093.6 | 51 |
| 23 | MPIFLDHILNKFWIPHYAGSG | 15915 | 2061.6 | 52 |
| 24 | MPIFLGHILNKFWILHYAGSG | 14873 | 1926.6 | 53 |
| 25 | MPIFLDHILNKFWILRYAGSG | 13449 | 1742.1 | 54 |
| 26 | MPIFLDHILDKFWILHYAGSG | 13444 | 1741.5 | 55 |
| 27 | MPIFLDRILNKFWILHYAGSG | 13246 | 1715.8 | 56 |
| 28 | MPIFLDHILNKLWILHYAGSG | 12869 | 1667.0 | 57 |
| 29 | MLIFLDHILNKFWILHYAGSG | 12383 | 1604.1 | 58 |
| 30 | MSIFLDHILNKFWILHYAGSG | 12324 | 1596.4 | 59 |
| 31 | MPIFLDHILNEFWILHYAGSG | 12091 | 1566.2 | 60 |
| 32 | MPIFLDHILNKFWTLHYAGSG | 11723 | 1518.6 | 61 |
| 33 | MPIFLDHILNKSWILHYAGSG | 11555 | 1496.8 | 62 |
| 34 | MPIFLDHILNKFWVLHYAGSG | 11334 | 1468.2 | 63 |

TABLE 3-continued

SPAM point mutants found in next generation sequencing data. Next generation
sequencing results were binned based on the family groups and 108 sequences
from SPAM family that were appearing more than 1,000 times in the sequencing
results were identified and were evaluated to see what percent were presenting
the same residue as SPAM at each position. Rank within the pool, peptide
sequence, the related copy number and the frequency of appearance calculated
as part per million (PPM) are illustrated for each sequence.
Variable residues are underlined.

| # | Sequence | Copy Number | PPM | SEQ ID NO: |
|---|----------|-------------|-----|------------|
| 35 | MPIFLDHILNKFWILHYTGSG | 10884 | 1409.9 | 64 |
| 36 | MPLFLDHILNKFWILHYAGSG | 10664 | 1381.4 | 65 |
| 37 | MPIFLDHIPNKFWILHYAGSG | 10151 | 1314.9 | 66 |
| 38 | MPIFLDHILNKFWILHYDGSG | 9601 | 1243.7 | 67 |
| 39 | MPIFLDHILNRFWILHYAGSG | 9114 | 1180.6 | 68 |
| 40 | MPKFLDHILNKFWILHYAGSG | 9036 | 1170.5 | 69 |
| 41 | MPIFLDHILNKFWILHFAGSG | 8740 | 1132.2 | 70 |
| 42 | MPIFLDHILNKFWILYYAGSG | 8649 | 1120.4 | 71 |
| 43 | MPIFLDYILNKFWILHYAGSG | 7697 | 997.0 | 72 |
| 44 | MPIILDHILNKFWILHYAGSG | 6976 | 903.6 | 73 |
| 45 | MPIFVDHILNKFWILHYAGSG | 6774 | 877.5 | 74 |
| 46 | MPIFLDHILNKFWILHNAGSG | 6553 | 848.9 | 75 |
| 47 | MPIFLDHLLNKFWILHYAGSG | 6541 | 847.3 | 76 |
| 48 | MPIFLDHILNKFWILHYVGSG | 6054 | 784.2 | 77 |
| 49 | MPISLDHVLNKFWILHYAGSG | 5941 | 769.6 | 78 |
| 50 | MPIFLDLILNKFWILHYAGSG | 5842 | 756.8 | 79 |
| 51 | MPIFLNHILNKFWILHYAGSG | 5331 | 690.6 | 80 |
| 52 | MPIFLDHILNKFWIFHYAGSG | 5321 | 689.3 | 81 |
| 53 | MPILLDHVLNKFWILHYAGSG | 4880 | 632.1 | 82 |
| 54 | MRRSVDHILLKFWILHNSGSG | 4244 | 549.8 | 83 |
| 55 | MPIFLDHILNKFLILHYAGSG | 3867 | 500.9 | 84 |
| 56 | MPISLDHTLNKFWILHYAGSG | 3801 | 492.4 | 85 |
| 57 | MPIFLDHILYKFWILHYAGSG | 3742 | 484.7 | 86 |
| 58 | MQIFLDHILNKFWILHYAGSG | 3638 | 471.3 | 87 |
| 59 | MPIFLDHILNKFWIHHYAGSG | 3444 | 446.1 | 88 |
| 60 | MPILLDHTLNKFWILHYAGSG | 3056 | 395.9 | 89 |
| 61 | MPIFLDHILTKFWILHYAGSG | 3048 | 394.8 | 90 |
| 62 | MRIFLDHILNKFWILHYAGSG | 3016 | 390.7 | 91 |
| 63 | MPIFLDHILNKFWILLYAGSG | 2916 | 377.7 | 92 |
| 64 | MRTSVDHILLKFWILHNSGSG | 2821 | 365.4 | 93 |
| 65 | MPIFLDHILNKFWILHYSGSG | 2808 | 363.7 | 94 |
| 66 | MPIFLDHALNKFWILHYAGSG | 2773 | 359.2 | 95 |
| 67 | MPIFLDHILNKFCILHYAGSG | 2668 | 345.6 | 96 |
| 68 | MPIFLDHILNKFWILHYGGSG | 2391 | 309.7 | 97 |

TABLE 3-continued

SPAM point mutants found in next generation sequencing data. Next generation
sequencing results were binned based on the family groups and 108 sequences
from SPAM family that were appearing more than 1,000 times in the sequencing
results were identified and were evaluated to see what percent were presenting
the same residue as SPAM at each position. Rank within the pool, peptide
sequence, the related copy number and the frequency of appearance calculated
as part per million (PPM) are illustrated for each sequence.
Variable residues are underlined.

| # | Sequence | Copy Number | PPM | SEQ ID NO: |
|---|----------|-------------|-----|------------|
| 69 | MPIFLDHILIKFWILHYAGSG | 2329 | 301.7 | 98 |
| 70 | MPIFLDHKLNKFWILHYAGSG | 2249 | 291.3 | 99 |
| 71 | MTIFLDHILNKFWILHYAGSG | 2115 | 274.0 | 100 |
| 72 | MRISVDHILLKFWILHDSGSG | 2094 | 271.3 | 101 |
| 73 | MPIFLDHILNKYWILHYAGSG | 2039 | 264.1 | 102 |
| 74 | MPRFLDHILNKFWILHYAGSG | 2024 | 262.2 | 103 |
| 75 | MRIPVDHILLKFWILHNSGSG | 1963 | 254.3 | 104 |
| 76 | MKKFTDHTLMKFWILVNAGSG | 1894 | 245.3 | 105 |
| 77 | MPIFLVHILNKFWILHYAGSG | 1812 | 234.7 | 106 |
| 78 | MPIFLDHIQNKFWILHYAGSG | 1762 | 228.2 | 107 |
| 79 | MAIFLDHILNKFWILHYAGSG | 1687 | 218.5 | 108 |
| 80 | MKKFLDHTLMKFWILVNAGSG | 1553 | 201.2 | 109 |
| 81 | MPIFLEHILNKFWILHYAGSG | 1544 | 200.0 | 110 |
| 82 | MPIFPDHVLNKFWILHYAGSG | 1487 | 192.6 | 111 |
| 83 | MPIFLDHILNKFWILNYAGSG | 1474 | 190.9 | 112 |
| 84 | MPIFLDHILHKFWILHYAGSG | 1446 | 187.3 | 113 |
| 85 | MPIFRDHILNKFWILHYAGSG | 1404 | 181.9 | 114 |
| 86 | MPIFLDHILNKFSILHYAGSG | 1340 | 173.6 | 115 |
| 87 | MGTSYDHIFIKFMILHTTGSG | 1337 | 173.2 | 116 |
| 88 | MPIPLDHILNKFWILHYAGSG | 1331 | 172.4 | 117 |
| 89 | MPIVLDHILNKFWILHYAGSG | 1310 | 169.7 | 118 |
| 90 | MRISVDHVLLKFWILHNSGSG | 1275 | 165.2 | 119 |
| 91 | MPIFLYHILNKFWILHYAGSG | 1250 | 161.9 | 120 |
| 92 | MPIFLDHILNKFWNLHYAGSG | 1226 | 158.8 | 121 |
| 93 | MRISVDHTLLKFWILHNSGSG | 1198 | 155.2 | 122 |
| 94 | MPIFPDHTLNKFWILHYAGSG | 1166 | 151.0 | 123 |
| 95 | MPISPDHILNKFWILHYAGSG | 1139 | 147.5 | 124 |
| 96 | MPVFLDHVLNKFWILHYAGSG | 1129 | 146.2 | 125 |
| 97 | MPTSLDHILNKFWILHYAGSG | 1129 | 146.2 | 126 |
| 98 | MPIFLDHILNKFWILHYPGSG | 1114 | 144.3 | 127 |
| 99 | MPIFLDHILNKFWIIHYAGSG | 1111 | 143.9 | 128 |
| 100 | MPIFLDHILNNFWILHYAGSG | 1106 | 143.3 | 129 |
| 101 | MPIFLDNILNKFWILHYAGSG | 1080 | 139.9 | 130 |
| 102 | MPTFLDHTLNKFWILHYAGSG | 1061 | 137.4 | 131 |

TABLE 3-continued

SPAM point mutants found in next generation sequencing data. Next generation
sequencing results were binned based on the family groups and 108 sequences
from SPAM family that were appearing more than 1,000 times in the sequencing
results were identified and were evaluated to see what percent were presenting
the same residue as SPAM at each position. Rank within the pool, peptide
sequence, the related copy number and the frequency of appearance calculated
as part per million (PPM) are illustrated for each sequence.
Variable residues are underlined.

| # | Sequence | Copy Number | PPM | SEQ ID NO: |
|---|----------|-------------|-----|------------|
| 103 | MPTFLDHVLNKFWILHYAGSG | 1058 | 137.1 | 132 |
| 104 | MPIFLDQILNKFWILHYAGSG | 1045 | 135.4 | 133 |
| 105 | MPMFLDHTLNKFWILHYAGSG | 1029 | 133.3 | 134 |
| 106 | MQISVDHILLKFWILHNSGSG | 1020 | 132.1 | 135 |
| 107 | MPIFLDHILNKFWFLHYAGSG | 1008 | 130.6 | 136 |
| 108 | MPMFLDHVLNKFWILHYAGSG | 1001 | 129.7 | 137 |

Correlation between the next-generation sequencing results and alanine scanning data is discordant for only two residues: L9 and N10. L9 is highly conserved in the final pool yet can be replaced with alanine with no significant effect on PD-L1 binding. On the other hand, N10 shows relatively low conservation in the final sequence pool, yet mutation to alanine almost completely abrogates PD-L1 binding. While these discrepancies may arise from positional differences in background mutation rate, they may also represent additional functional information. For example, mutations at position 10 are often observed in the context of multiple mutations in the N-terminal region, potentially indicating cooperativity between different parts of the SPAM peptide. Taken together, the positional scanning data and the next generation sequencing analysis data indicate that the majority of the residues in the C-terminal portion of the SPAM peptide are critical for PD-L1 binding and provide basic structure-activity information for the interaction.

These data suggest that the N-terminal residues of SPAM may therefore be dispensable, and SPAM could possibly be truncated to a shorter, yet still as active peptide. To test this hypothesis and to gain a belier understanding of the contribution of the N-terminal residues in the observed binding, we constructed several N-terminal truncations of SPAM and compared their binding with wild type SPAM. [$^{35}$S]-labeled N-terminally truncated variants of SPAM were translated where one (Trunc 1; P2 deleted MIFLDHILNKFWILHYA (SEQ ID NO: 4)), two (Trunc 2; P2, and 13 deleted MFLDHILNKFWILHYA (SEQ ID NO: 5)), three (Trunc 3; P2, 13, and F4 deleted MLDHILNKFWILHYA (SEQ ID NO: 6)) and 5 four (Trunc 4; P2, 13, F4, and L5 deleted MDHILNKFWILHYA (SEQ ID NO: 7)) residues were removed from the N-terminus of SPAM. These truncated variants were tested for hPD-L1 binding and show reduced binding (~25% or less) to hPD-L1 as compared with full-length SPAM (FIG. 3B). Taken together with the alanine scanning mutations in this region described above that showed little-to-no loss of binding, the loss of >75% of binding in these truncation variants could be due to the loss of main chain/backbone contacts between hPD-L1 and these N-terminal SPAM residues.

SPAM Peptide Binding is Blocked by Inhibitors of the PD-L1/PD-1 Interaction

Competition binding assays were performed to determine the functional significance of the PD-L1/SPAM peptide interaction. hPD-L1-binding ligands known to inhibit PD-1 binding (WL12, a macrocyclic hPD-L1 inhibitor peptide, Atezolizumab, an hPD-L1 specific monoclonal antibody, and mPD-1 the murine variant of PD-1) were used as competitors. All three competitor ligands significantly inhibited the SPAM/hPD-L1 interaction (FIG. 4A) suggesting that SPAM peptide overlaps with at least a portion of the PD-L1 recognition site used by these ligands. As expected, control goat anti-rabbit polyclonal IgG antibody had no effect on hPD-L1 binding.

SPAM peptide binding was further evaluated in the presence of varying concentrations of BMS-202. BMS-202 is a small molecule that stabilizes a non-functional dimeric complex of PD-L1, blocking the PD-1 binding site and inhibiting PD-1 binding. SPAM peptide binding is almost completely inhibited at 750 nM BMS-202 (FIG. 4B), indicating that the SPAM binding site wholly or partly overlaps the binding site utilized by known PD-L1 modulating ligands.

An ELISA-based activity assay was employed to measure the potency of SPAM peptide inhibition of the hPD-L1/PD-1 interaction (FIG. 4C-D). In this assay, biotinylated hPD-L1 was immobilized on streptavidin magnetic beads and incubated with various concentrations of SPAM peptide, followed by incubation with HA-tagged mPD-1 and detection with anti-HA secondary antibody. SPAM peptide almost completely disrupted PD-1 binding at 10 μM providing further evidence that SPAM can functionally inhibit the hPD-L1/mPD-1 interaction with an approximate IC$_{50}$ of 1.1 μM when hPD-L1 and mPD-1 are present at a concentration of 100 nM. This observation is consistent with the fluorescence polarization data which indicates that SPAM binds to hPD-L1 with a higher affinity (K$_D$=60-120 nM) than the hPD-L1/mPD-1 interaction (K$_D$≈3 μM).

The competition data thus suggests that SPAM binds at the PD-1 interaction site and provides a framework for interpreting our specificity data of SPAM binding to hPD-L1, mPD-L1, and hPD-L2 (FIG. 2). We thus compared sequence alignments and crystal structures of hPD-L1, mPD-L1 and hPD-L2 (FIGS. 9 and 10) in order to determine if any structural features of the PD-1 binding site of these complexes might provide a basis for SPAM binding specificity. Despite the high level of homology between these proteins, the PD-1 interaction surface of hPD-L1 and mPD-L1 differs by a single residue (Arg113) while the PD-1 interaction surface of hPD-L1 and hPD-L2 differs by six residues. Several other residues that are not located in the PD-1 interaction surface are also different and may contribute to the specificity observed for SPAM binding (FIG. 10). We hypothesize that the SPAM binding with hPD-L1 likely involves interaction with at least some of these residues, leading to the specificity of SPAM for hPD-L1.

Binding of SPAM Peptide Inhibits Binding of Anti-PD-L1 Antibodies to hPD-L1 Expressing Cells In vitro characterization of the selected SPAM peptide revealed strong binding to the recombinant hPD-L1 ectodomain and inhibition of the PD-L1/PD-1 interaction. Although we had demonstrated that the SPAM peptide bound to hPD-L1*, we also wanted to determine if this interaction is maintained in a cellular context. To do this, we measured SPAM peptide inhibition of anti-PD-L1 antibody binding to hPD-L1 expressed on the surface of Chinese hamster ovary (CHO) cells (CHO-hPD-L1). Both Atezolizumab and Avelumab antibodies were fluorescently labeled with FAM-NHS and titrated against CHO-hPD-L1, yielding $K_D$ values of 0.2 nM and 5.1 nM, respectively (FIG. 12A). These values are in agreement with reported binding affinities. Next, we pre-incubated CHO-hPD-L1 cells for 30 min at 4° C. with SPAM peptide, a control scrambled peptide (SPAM-scramble), or the PD-L1 inhibitors WL-12 and BMS-202 in serum-free media. Cells were washed and then incubated with 1 nM Fluorescein-Atezolizumab or 10 nM Fluorescein-Avelumab for 30 min at 4° C. Cells were washed again and analyzed by flow cytometry (FIG. 5B-C). At high (20 µM) concentrations of SPAM peptide, where the peptide was preincubated with cells before adding antibody, we observed a significant decrease in both Fluorescein-Atezolizumab and Fluorescein-Avelumab binding to CHO-hPD-L1. This effect was not observed from SPAM-scramble. As expected, treatment with WL-12 and BMS-202 markedly reduced antibody binding.

We performed similar experiments with CHO-mPD-L1 cells which express mPD-L1 to determine if this effect was specific to hPD-L1 expression. We have developed two cross-reactive anti-hPD-L1/mPD-L1 antibodies, 16373 and 16377. These antibodies were labeled with Fluorescein, titrated against CHO-hPD-L1 and CHO-mPD-L1 cells (FIG. 12B-C) and subjected to competition experiments as described above. Similar to the clinical antibodies, we observed blocking of Fluorescein-16373 and Fluorescein-16377 from pre-treatment with SPAM peptide, WL-12 and BMS-202 in CHO-hPD-L1 cells, however, this blocking was absent in CHO-mPD-L1 cells for all compounds tested (with the exception of 20 µM BMS-202; FIG. 5C-F) confirming that hPD-L1 selectivity is maintained in cell culture.

In light of our in vitro affinity data that showed SPAM has a 67 nM affinity for hPD-L1* (FIG. 2B) and the stability data that showed SPAM was not degraded by serum, the high concentrations of SPAM peptide that were necessary to effectively block antibody binding was somewhat surprising. These data suggested that the affinity of SPAM binding to hPD-L1 in a cellular context was decreased relative to our previous in vitro experiments. One possible explanation for this difference could be due to the glycosylation state of recombinant hPD-L1* protein used in vitro and hPD-L1 protein expressed on the surface of CHO-hPD-L1 cells. To compare the glycosylation state of hPD-L1* and hPD-L1 from CHO-hPD-L1 cells, we performed a western blot on hPD-L1 protein samples treated with or without PNGase F, which can remove N-linked glycans. We observed that both hPD-L1* and hPD-L1 from CHO-hPD-L1 cells both show a band shift towards faster mobility, corresponding to the removal of N-linked glycans for both protein sources (FIG. 11). We note that hPD-L1 from CHO-hPD-L1 cells shows a more drastic shift, suggesting that CHO-derived hPD-L1 is much more heavily glycosylated, and could provide an explanation for the loss of affinity in SPAM binding to CHO-hPD-L1 cells; the more extensive glycosylation might interfere with the SPAM/hPD-L1 interface.

CONCLUSION

Dual-stage mRNA display selection for hPD-L1 ligands resulted in the identification of SPAM peptide, an 18-amino acid linear peptide with mid-nanomolar affinity and high selectivity for hPD-L1 relative to other B7 family members. The SPAM/PD-L1 interaction is significantly stronger than the PD-1/PD-L1 interaction and is comparable or superior to previously reported linear PD-L1 binding peptides despite the relatively small size of the SPAM peptide. We speculate that the high affinity and selectivity of the SPAM peptide may have resulted from sequential selections with two high-diversity mRNA Display libraries (X9 and X17).

SPAM is non-homologous to known PD-L1 binding peptides and was found to competitively inhibit binding of PD-1 and ligands that interact with the PD-1 binding site. Point mutational analysis and next generation sequencing has identified numerous positions within the N-terminal region which do not significantly contribute to binding and are therefore candidates for further affinity maturation. SPAM peptide was found to inhibit the binding of anti-PD-L1 antibodies in clinical use with potencies comparable to that of the small molecule BMS-202. Although the affinity of the SPAM peptide is lower than that of the cyclic, unnatural peptide WL-12, its natural, linear architecture facilitates rapid and inexpensive synthesis or expression as a fusion protein for cell-based studies. Taken together, the results suggest that the selected linear peptide ligand selectively recognizes hPD-L1 and can potentially serve as a lead compound for further development of PD-L1 antagonists.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Cell Lines. CHO-hPD-L1 and CHO-mPD-L1 cells were maintained in DMEM supplemented with 10% (v/v) fetal bovine serum (Sigma) and 1% (v/v) penicillin-streptomycin (Corning, Inc.). Cells were maintained at 37° C. in a humidified incubator supplemented with 5% (v/v) $CO_2$. Expi293F cells were maintained in suspension culture with Expi293 Expression Medium (Thermo Fisher), 125 mL flasks rotated at 120 rpm in 37° C. in a humidified incubator supplemented with 7% (v/v) $CO_2$.

Expression and Purification of Recombinant hPD-L1, mPD-L1 and mPD-1 in *E. coli* gBlocks for hPD-L1, mPD-L1 and mPD-1 extracellular domains were ordered from Integrated DNA Technologies. Expression constructs for the extracellular domain of hPD- L1 were designed from A18 to T239 with a methionine added to the N-terminus and an Avi tag (GLNDIFEAQK-IEWHE) (SEQ ID NO: 153) and a hexahistidine tag (HHHHHH) (SEQ ID NO: 154) added to the C-terminus:

```
                                    (SEQ ID NO: 152)
MAFTVTVPKDLYVVEYGSNMTIECKFPVEKQLDLA

ALIVYWEMEDKNIIQFVHGEEDLKVQHSSYRQRAR

LLKDQLSLGNAALQITDVKLQDAGVYRCMISYGGA

DYKRITVKVNAPYNKINQRILVVDPVTSEHELTCQ

AEGYPKAEVIWTSSDHQVLSGKTTTTNSKREEKLF

NVTSTLRINTTTNEIFYCTFRRLDPEENHTAELVI

PELPLAHPPNERTGGAGGLNDIFEAQKIEWHEGGL

EHHHHHH.
```

The expression construct for mPD-L1 consisted of its extracellular domain (from A18 to H239) with a methionine added to the N-terminus and an Avi Tag (SEQ ID NO: 153) and a hexahistidine Tag) (SEQ ID NO: 154) added to the C-terminus. The Avi Tag was site-specifically biotinylated in vitro on the ε-amino group of lysine (bold) using biotin ligase

```
(MAFTITAPKDLYVVEYGSNVTME-CRFPVERELD

LLALVVYWEKEDEQVIQFVAGEEDLKPQHSNFRGR

ASLPKDQLLKGNAALQITDVKLQDAGVYCCIISY

GGADYKRITLKVNAPYRKINQRISVDPATSEHELI

CQAEGYPEAEVIWTNS DHQPVSGKRSVTTSRTEG

MLLNVTSSLRVNATANDVFYCTFWRSQPGQNHTAE

LIIPELPATHPPQNRTHGGAGGLNDIFEAQKIEW

HEGGLEHHHHHH (SEQ ID NO: 156)).
```

The expression construct for mPD-1 consisted of its extracellular domain (from L15 to S157) with a methionine and an alanine added to the N-terminus, an unpaired cysteine mutated to serine (C83S; bold) and an HA tag (YPYDVPDYA) (SEQ ID NO: 155) and a His tag (SEQ ID NO: 154) on the C-terminus:

```
                                    (SEQ ID NO: 157)
MALEVPNGPWRSLTFYPAWLTVSEGANATFTCSLS

NWSEDLMLNWNRLSPSNQTEKQAAFSNGLSQPVQD

ARFQIIQLPNRHDFHMNILDTRRNDSGIYLCGAIS

LHPKAKIEESPGAELVVTERILETSTRYPSGGYPY

DVPDYALEHHHHHH.
``` gBlocks were PCR amplified using Taq DNA polymerase and were cloned into pET24a using NdeI and XhoI restriction enzymes, followed by Sanger sequencing. Plasmids were then transformed into BL21 (DE3) competent *E. coli* strains with or without pBirAcm (a pACYC184-based plasmid expressing BirA for in vivo biotinylation; Avidity LLC). Protein expression was performed in the presence of 30 mg/L kanamycin without pBirAcm, while 20 mg/L chloramphenicol was added in the presence of pBirAcm. The proteins were expressed overnight at 37° C. via auto-induction using ZYM-5052 and the cells were harvested using centrifugation.

Proteins were purified via denaturing affinity chromatography using an FPLC (Bio-Rad). Inclusion bodies were extracted from cell pellets using 100 mL Buffer A (100 mM NaH$_2$PO$_4$, 10 mM Tris-HCl, and 6 µM guanidinium hydrochloride, pH 8.0) and loaded onto a Ni-NTA column. The column was washed with 100 mL Buffer B (100 mM NaH$_2$PO$_4$, 10 mM Tris-HCl, and 8 µM Urea, pH of 8.0) and 100 mL Buffer C (100 mM NaH$_2$PO$_4$, 10 mM Tris-HCl, and 8 µM Urea, pH of 6.3) and eluted using a linear gradient from Buffer C to Buffer D (100 mM NaH$_2$PO$_4$, 10 mM Tris-HCl, 8 µM Urea, and 100 mM imidazole, pH of 4.5).

Fractions were analyzed using SDS-PAGE and those containing protein were combined, concentrated, and refolded in 1 µM arginine, 100 mM Tris (pH=8.0), 2 mM EDTA, 0.5 mM reduced glutathione, and 0.05 mM oxidized glutathione using infinite dilution at 4° C. overnight. The refolded proteins were concentrated, and buffer exchanged using Amicon Ultracel 10 k centrifugal filters (Millipore Sigma) and then further purified using a Q Sepharose HP anion exchange column (GE Healthcare). Protein purity was analyzed using native-PAGE and SDS-PAGE and those fractions containing pure protein were combined, concentrated, and flash frozen in liquid nitrogen and stored at −80° C.

Expression, Purification and Biotinylation of Recombinant Glycosylated Human PD-L1 (hPD-L1*) and PD-L2 (hPD-L2*) Ectodomain in Expi293F cells pCDNA3.4 vectors encoding the hPD-L1* or hPD-L2* ectodomains were ordered from GeneArt (Thermo Fisher Scientific). The hPD-L1* vector included amino acids A18-T239, an Avi Tag and a hexahistidine tag (SEQ ID NO: 154). The hPD-L2* vector included amino acids L20-T220, an Avi Tag and a hexahistidine tag (SEQ ID NO: 154). Proteins were expressed using the Expi293F expression system per manufacturer's instructions (Thermo Fisher Scientific) and purified at 4° C. with Ni-NTA agarose (G-Biosciences). Briefly, 293F conditioned media was 0.2 µm filtered and dialyzed 3×24 hours against dialysis buffer (25 mM Hepes-KOH pH 8.0, 200 mM NaCl, 5% (v/v) glycerol, 0.01% (w/v) sodium azide). Dialyzed media was mixed 1:1 with equilibration buffer (50 mM phosphate buffer pH 8.0, 300 mM NaCl, 10 mM imidazole, 0.05% (v/v) Tween-20) and 1 mL Ni-NTA resin and 20 µL 0.5 µM NiSO$_4$ were added and incubated overnight with rotation. The mixture was loaded onto a fritted column and the resin was washed once with 25 mL equilibration buffer and twice with 25 mL wash buffer (50 mM phosphate buffer pH 8.0, 300 mM NaCl and 20 mM imidazole). Protein was then eluted with 15 mL of elution buffer (50 mM phosphate buffer pH 8.0, 300 mM NaCl, 250 mM imidazole). The eluate was buffer exchanged against dialysis buffer using Amicon Ultracel 10 k centrifugal filters (Millipore Sigma). Protein concentration was calculated using the Pierce BCA protein assay (Thermo Fisher Scientific) per manufacturer's instructions. hPD-L1* yield was 2.5 mg. hPD-L2* yield was 6.3 mg protein. In vitro biotinylation of 2 mg of purified protein was performed with recombinant BirA enzyme (Avidity LLC) per manufacturer's instructions. Biotinylation was confirmed by incubation of protein with an excess of neutravidin agarose (Thermo Fisher Scientific). The flow-through was compared with neutravidin captured protein by SDS-PAGE. Post-biotinylation, the hPD-L1* yield was 2.4 mg. Post-biotinylation the hPD-L2* yield was 0.9 mg.

Surface Plasmon Resonance (SPR) Assay

SPR analysis was performed on a Biacore T-100 at the USC Nanobiophysics core. *E. coli* expressed biotinylated hPD-L1 was immobilized onto a sensor chip SA (GE Healthcare Life Sciences) and different concentrations (from $1.5 \times 10^{-7}$ to $2.9 \times 10^{-5}$ M) of mPD-1 was flowed over the chip at a rate of 50 µL/min for 60 seconds in a buffer consisting of 50 mM HEPES-KOH pH 7.5, 150 mM NaCl, 0.05% (v/v) Tween-20 and 1 mg/mL BSA at 25° C. The response values were fit to a one-site saturation binding model in GraphPad Prism to obtain an equilibrium binding constant.

mRNA Display Library Preparation $X_9$ Library: A random DNA library encoding nine randomized positions was constructed from oligos (5' G GGA CAA TTA CTA TTT ACA ATA ACC ATG NNK NNS NNS NNS NNS NNS NNS NNS NNK GGT AGT GGT ACG TCT GGC TCC AGC 3') (SEQ ID NO: 13) where N=A, C, G or T, S=C or G and K=G or T) and was PCR amplified together with primers 47T7Ext3 (5' GGA TTC TAA TAC GAC TCA CTA TAG GGA CAA TTA CTA TTT ACA ATA ACC 3') (SEQ ID NO: 14) and 3Extlib3 (5' GCT GGA GCC AGA CGT ACC ACT ACC 3') (SEQ ID NO: 15).

$X_{17}$ Library: To perform the maturation selection, a doped DNA library ($X_{17}$ library) based on the wild type hPD-L1 signal peptide sequence was constructed such that the probability at each nucleotide was 70% of the wild-type nucleotide and 10% each of the other three nucleotides (corrected for the different coupling rates of the phosphoramidite monomers). $X_{17}$ library template oligo (5' G GGA CAA TTA CTA TTT ACA ATT ACA ATG 233 141 442 321 344 442 141 444 143 123 412 433 212 243 242 112 324 GGA TCC GGT TCA AGC GGT CAC 3' where 1: 75.0% A; 7.1% G; 10.7% C; 7.1% T; 2: 10.7% A; 7.1% G; 75.0% C; 7.1% T; 3: 13.6% A; 63.6% G; 13.6% C; 9.1% T; and 4: 13.6% A; 9.1% G; 13.6% C; 63.6% T) (SEQ ID NO: 16) was PCR amplified with primers SP5 (5' GGA TTC TAA TAC GAC TCA CTA TAG GGA CAA TTA CTA TTT ACA ATT ACA 3') (SEQ ID NO: 17) and SP3 (5' TGA ACT ATG GTG ATG ATG GTG ACC GCT TGA ACC G 3') (SEQ ID NO: 18).

Both DNA libraries contained a T7 promoter sequence (5' TAA TAC GAC TCA CTA TA 3') (SEQ ID NO: 19), a transcription start codon (5' GGG 3'), a ATMV translation enhancer region derived from Tobacco Mosaic Virus (5' ACA ATT ACT ATT TAC AAT TAC A 3') (SEQ ID NO: 20), an open reading frame and a 3' constant sequence (for $X_9$ library: 5' GGT AGT GGT ACG TCT GGC TCC AGC 3' (SEQ ID NO: 21) and for $X_{17}$ library: 5' GGA TCC GGT TCA AGC GGT CAC CAT CAT CAT CAC CAT AGT TCA 3') (SEQ ID NO: 22).

To generate the mRNA library, 10 µg/mL of the PCR-amplified DNA library was incubated in transcription buffer (80 mM HEPES-KOH pH 7.5, 2 mM spermidine, 40 mM DTT, 25 mM MgCl$_2$ and an NTP mixture consisting of 4 mM of each ATP, CTP, GTP and UTP) and briefly heated before initiating the transcription reaction using T7 RNA polymerase. The transcription reaction was incubated at 37° C. overnight and the reaction quenched by adding 0.1 volume of 0.5 µM EDTA, pH 8.0. The transcribed mRNA library was gel purified using denaturing urea-PAGE, the mRNA bands excised, and the mRNA extracted using electroelution (Elutrap, Schleicher & Schuell) followed by desalting and concentrating using 0.5 mL 30 k Amicon centrifugal filter (Millipore Sigma). The purified mRNA was then ligated to a puromycin-DNA linker (pF30P-5' 8AA AAA AAA AAA AAA AAA AAA A77 7AC C6 3') (SEQ ID NO: 23) where 6=puromycin CPG, 7=spacer phosphoramidite 9 and 8=phosphate using chemical phosphorylation reagent I (Keck Biotechnology Resource Laboratory, New Haven, CT) at the 3' end. Splint oligos (5' TTT TTT TTT TTT GCT GGA GCC AGA 3' (SEQ ID NO: 176) for $X_9$ library and 5' TTT TTT TTT TTT TGA ACT ATG GTG 3' (SEQ ID NO: 24) for $X_{17}$ library) were included to facilitate the ligation. mRNA, pF30P, and splint oligo were incubated in ligation buffer and T4 DNA ligase for 90 min at room temperature. The ligated library was gel purified using denaturing urea-PAGE and electroeluted as previously described to provide the ligated mRNA library template.

mRNA Display Translation and Selection

Ligated mRNA library was translated using rabbit reticulocyte lysate (Green Hectares) in the presence of 100 mM KOAc, 0.5 mM MgOAc and 1X translation buffer consisting of 20 mM HEPES-KOH pH 7.6, 8 mM creatine phosphate, 2 mM DTT and 25 µM of each amino acid. The translation mixture was incubated at 30° C. for 1 hour followed by adding 0.5 µM KCl and 50 mM MgCl$_2$ to facilitate mRNA-peptide fusion formation. The mRNA-peptide fusion library was purified using oligo dT-agarose beads in isolation buffer (100 mM Tris-HCl, pH 8.0, 1 µM NaCl and 0.2% (v/v) Triton X-100) for 1 hour at 4° C. The beads were washed using isolation buffer and mRNA-peptide fusions were eluted in water at 65° C. For $X_{17}$ library a secondary purification was performed using Dynabeads™ His-Tag Isolation and Pulldown beads (Thermo Fisher Scientific) to selectively isolate the mRNA-peptide fusion from unfused ligated mRNA. Purified mRNA-peptide fusion library was desalted using centrisep columns (Princeton Separations) and reverse transcribed using Superscript II reverse transcriptase. The reverse transcribed library was then exposed to hPD-L1 immobilized on streptavidin or neutravidin agarose beads (Thermo Fisher scientific) or streptavidin coated magnetic beads (Dynabeads™ MyOne™ Streptavidin T1; Thermo Fisher Scientific) in blocking buffer (20 mM HEPES-KOH pH 7.5, 150 mM NaCl, 0.2% (v/v) Tween-20, 1 mg/mL BSA, 50 µg/mL tRNA and 0.02 mM biotin). For the first round, 300 pmol hPD-L1 target was used while 75 pmol was used for the subsequent rounds. Selections were performed at 4° C. except for the last two rounds of $X_{17}$ library selection where the selection was performed at room temperature. After washing the beads to remove non-functional sequences, the remaining DNA was PCR amplified with library primers to generate a dsDNA library for the next round of selection. The final enriched DNA libraries were sequenced as described below.

Radiolabeled Binding Assays

[$^{35}$S]-labeled peptides were translated as described above by including 2 µCi labeled methionine (Perkin Elmer) per 10 pmol of template in the translation reaction. Each peptide was tested with a GSGTSGSS (for $X_9$-library derived peptides) (SEQ ID NO: 11) or a GSGSSGHHHIHHHSS (for X17-library derived peptides) (SEQ ID NO: 12) C-terminal sequence. Binding assays using [$^{35}$S]-labeled peptide-RNA fusions were similarly performed on hPD-L1 immobilized beads using 75 pmol hPD-L1 immobilized on streptavidin or neutravidin agarose beads (Thermo Fisher scientific) in blocking buffer (20 mM HEPES-KOH pH 7.5, 150 mM NaCl, 0.2% (v/v) Tween-20, 1 mg/mL BSA, 50 µg/mL tRNA and 0.02 mM biotin) at 4° C. for 1 h. The supernatant was removed and was counted. The beads were subsequently washed three times with 1 mL of blocking buffer and the washes were also counted. Finally, the beads were resuspended in 1 mL of blocking buffer and were counted separately. The ratio of the counts remaining on the beads to the total counts added to the binding reaction (the sum of the counts for supernatant, washes, and beads) was calculated to determine the percent bound.

For radioactive competition assays, hPD-L1-immobilized streptavidin agarose beads were preincubated with the desired competitor for one hour at 4° C. followed by addition of the radiolabeled peptide for 1 h. The ratio of the counts remaining on the beads to the total counts added to the binding reaction was calculated to determine the percent bound.

Serum Stability of SPAM Peptide

ROX-SPAM peptide (100 μM) was incubated in DMEM media (Thermo Fisher Scientific) supplemented with 25% (v/v) single donor human plasma (Innovative Research) at 37° C. in triplicate. At times 0, 15, 30, 120 and 300 min, 40 μL was removed and protein precipitated by the addition of 80 μL ethanol. Samples were centrifuged for 10 min at 16,000×g and the supernatant removed for HPLC analysis. A total of 100 μL volume was injected in a HPLC gradient of $10^{-95}$% Buffer B over 15 minutes (Buffer A: dH$_2$O with 0.1% (v/v) TFA, Buffer B: CH$_3$CN+0.1% (v/v) TFA). Detection was performed at 570 nm.

In a complementary test, SPAM was in vitro translated and [$^{35}$S]-labeled as described above. After purification as above, the [$^{35}$S]-labeled peptide-RNA fusions were incubated with DMEM media supplemented with 25% (v/v) single donor human plasma at 37° C. in triplicate for 0, 60, 120, 240 and 480 min. The binding of serum incubated peptides was then evaluated on hPD-L1 immobilized beads using 75 pmol hPD-L1 immobilized on streptavidin agarose beads (Thermo Fisher scientific) in DMEM supplemented with 25% Serum buffer and 0.02 mM biotin at 4° C. for 1 h. The supernatant was removed and was counted. The beads were subsequently washed three times with 1 mL of blocking buffer and the washes were also counted. Finally, the beads were resuspended in 1 mL of blocking buffer and were counted separately. The ratio of the counts remaining on the beads to the total counts added to the binding reaction (the sum of the counts for supernatant, washes, and beads) was calculated to determine the percent bound.

Next Generation DNA Sequencing

The PCR-amplified enriched DNA libraries were uniquely barcoded and combined into a single sample and were sent for next generation Illumina DNA sequencing using a HiSeq 2500 Illumina sequencing platform at the USC Genome Core. The resulting FASTQ format file was analyzed using homemade python and bio-python scripts to translate the DNA sequences and count the frequency of the peptide sequences in each library. The number of times each sequence appeared was divided by the total number of sequences in the pool to obtain the appearance frequency.

Peptide Synthesis

First generation peptides were synthesized on a Prelude automated synthesis platform (Protein Technology, Inc.). Resin and amino acids were purchased from Advanced ChemTech. Rink amide AM resin (1 g, 0.47 mmol/g) was swollen in DMF for 60 min and washed twice with 6 mL DMF. The resin was deprotected with 20% (v/v) piperidine in DMF for 6 see, 10 min and 10 min. The initial C-terminal amino acid coupling was performed with 2 equivalents (0.94 mmol) of Fmoc-propargylglycine (Pra; 313 mg), 3 equivalents of N,N-diisopropylethylamine (DIEA, 1.41 mmol, 242 L) and 3 equivalents of N,N,N'N'-Tetramethyl-O-(1H-benzotriazol-1-yl) uronium hexafluorophosphate (HBTU, 1.41 mmol, 530 mg) in 6 mL DMF for 1 hour. The resin was washed 5x with DMF and capped 2×30 min with 200 μL of acetic anhydride and 480 μL DIEA in DMF.

For the synthesis of peptides with a C-terminal propargylglycine residue, 100 mg Fmoc-Pra-rink amide resin was loaded onto an automated synthesizer. Synthesis was performed with 3 equivalents each of Fmoc amino acid, DIEA and HBTU in N-methyl-2-pyrrolidone (NMP) using 2×10 min incubations. Fmoc was deprotected with 20% (v/v) piperidine in NMP for 2.5 min. After synthesis, resin was washed 5× with NMP, 5× with DCM, and dried under vacuum for 30 min. Peptides were cleaved from the resin by addition of 3 mL of 95% (v/v) trifluoroacetic acid, 2.5% (v/v) triisopropylsilane, and 2.5% (v/v) water for 2 hours. Peptides were precipitated in cold diethyl ether, centrifuged, washed once and dried under vacuum. The crude product was purified by reverse phase HPLC (Luna® 5 μm C18(2), LC Column 250×21.2 mm; Phenomenex) using gradient elution (5-95% Buffer B over 30 minutes; Buffer A: dH$_2$ with 0.1% (v/v) TFA, Buffer B: CH$_3$CN+0.1% (v/v) TFA). After lyophilization, peptides were obtained as a white solid. hPD-L1-SP (MRIFAVFIFMTYWHLLNAK-Pra) (SEQ ID NO: 8) yield was 19 mg (16.1%), ESI+[M+3H]$^{3+}$ expected 832.44, observed 832.89. SPAM (MPIFL-DHILNKFWILHYASG-Pra) (SEQ ID NO: 9) yield was 24.2 mg (20.5%), ESI+[M+3H]$^{3+}$ expected 837.10, observed 837.55. SPAM-scramble (YKLNLIHPHIFLMD-WIFASG-Pra) (SEQ ID NO: 10) yield was 6.6 mg (5.6%), ESI+[M+3H]$^{3+}$ expected 837.10, observed 837.55.

SPAM peptide was labeled with carboxy-X-rhodamine by copper catalyzed click chemistry. Peptide was dissolved in DMF and added to 500 μL of click solution (16 mg/mL CuSO$_4$·2H$_2$O and 30 mg/mL L-ascorbic acid), 2 μL of tris-(benzyltriazolylmethyl)amine (TBTA, 100 mg/mL) and 1.5 equivalents of ROX-azide. The reaction proceeded for 1 hour at 25° C. with end-over-end rotation. The crude product was purified by reverse phase HPLC as described above. ROX-SPAM yield was 2.8 mg (64%), ESI+[M+4H]$^{4+}$ expected 782.4, observed 782.52.

ELISA/Immunoprecipitation (IP) Assays

For ELISA/IP assays, 20 L of MyOne™ Streptavidin T1 magnetic beads Dynabeads™ (Thermo Fisher Scientific) were loaded with 100 nM biotinylated hPD-L1 in assay buffer (20 mM HEPES-KOH pH 7.5, 150 mM NaCl, 0.2% (v/v) Tween-20, 1 mg/mL BSA and 50 μg/mL tRNA) at 4° C. The beads were subsequently washed and incubated with either DMSO or different concentrations of SPAM peptide (0.1, 1 or 10 μM) in the assay buffer for 1 h at 4° C. followed by adding HA-tagged mPD-1 (100 nM) for 1 h at 4° C. The samples were then washed and incubated with a 1:5,000 dilution of HRP conjugated anti-HA antibody (Pierce HA Antibody, Rockford. Il, USA) for 1 h at 4° C. The beads were washed again and developed with TMB Substrate Kit (Thermo Scientific) for 30 minutes and the reactions stopped by adding 100 L of 2 μM sulfuric acid. The absorbance at 450 nm was measured on a Biotek Synergy H1 Hybrid Multi-Mode Microplate Reader.

Fluorescence Polarization Assays

A stock solution of hPD-L1 or hPD-L1* with a 5 μM starting concentration was prepared and serially diluted to concentrations ranging from 5 μM to 2.4 nM. ROX-SPAM peptide (100 nM) was incubated with dilutions of hPD-L1 and hPD-L1* in a black 96 well polystyrene plate in the dark at room temperature with shaking. The fluorescence polarization of each sample was measured on a Synergy H4 Hybrid Multi-Mode Microplate Reader. Each measurement was carried out in triplicate and the mean value was calculated. The values were fit to a one-site saturation binding model in GraphPad Prism to obtain the corresponding equilibrium dissociation constants.

Anti-PD-L1 Antibodies

Atezolizumab and Avelumab were expressed and purified based on their reported sequences by Atum Inc. The human anti-PD-L1 antibodies 16373 and 16377 were generated by the Oncology Research for Biologics and Immunotherapy Translation (ORBIT) moonshot platform at MD Anderson Cancer Center and were also produced by Atum Inc.

Fluorescein Labeling of Antibodies

Antibodies were incubated with 8 molar equivalents of 5/6-carboxyfluorescein succinimidyl ester (Life Technologies) in the presence of 5% (v/v) DMSO overnight at 4° C. Dye-labeled antibodies were then purified with 7 k MWCO Zeba Spin Desalting Columns (Thermo Fisher Scientific) per manufacturer's instructions. The degree of labeling was calculated as described previously.

Antibody Titration by Flow Cytometry

Cells were trypsinized and 200,000 cells/reaction resuspended in serum-free DMEM with a range of concentrations of Fluorescein-labeled antibodies. These samples were incubated at 4° C. for 60 min and washed three times with cold serum free DMEM. The pelleted cells were analyzed by flow cytometry with a BD FACSCalibur system using the FL1 channel. FlowJo v10.1 was used to gate to the major population and the median FL1 fluorescence reported. GraphPad Prism was used to calculate $K_D$.

Antibody Competition by Flow Cytometry

Cells were trypsinized and 200,000 cells/reaction resuspended in serum-free DMEM with 0-20 μM SPAM, SPAM-scramble, WL-12, or BMS-202 and incubated at 4° C. for 30 min. The cells were washed once with cold serum free DMEM and incubated with 1 nM FAM-Atezolizumab, 10 nM FAM-Avelumab, 50 nM FAM-16373, or 50 nM FAM-16377 in serum free DMEM at 4° C. for 30 min. Cells were then washed three times with cold serum free DMEM. Cells were subsequently processed by flow cytometry with a BD FACSCalibur system using the FL1 channel. FlowJo v10.1 was used to gate to the major population and median FL1 fluorescence reported.

Deglycosylation and Western Blotting of hPD-L1* and CHO-hPD-L1 Proteins

CHO-hPD-L1 cells were lysed with RIPA buffer (25 mM Tris, pH 7.5, 150 mM NaCl, 0.1% (w/v) SDS, 1% (v/v) NP-40, 1% (w/v) sodium deoxycholate) and centrifuged for at 16,000×g for 10 min to pellet insoluble material. A BCA assay was used to confirm protein concentration. To remove N-linked oligosaccharides, 20 μg of the lysate was treated with 4 μL of Rapid PNGase F buffer and 1 μL of Rapid PNGase F enzyme (New England Biolabs) in a total volume of 20 μL for 2 hours at 37° C. Recombinant hPD-L1* protein was treated in a similar manner. Control reactions without the addition of Rapid PNGase F enzyme were also performed. After incubation, 10 μL of 4x Coomassie sample buffer was added, and the samples boiled at 95° C. for 5 min. Protein samples then run on a 4-15% Mini-PROTEAN TGX gel (Bio-Rad) at 120V for 1 hour and transferred to a nitrocellulose membrane at 100V for 1 hour. The membrane was then incubated in blocking buffer (TBS supplemented with 0.1% (v/v) Tween-20 [TBST] and 3% (w/v) BSA) for 1 hour at room temperature. The membrane was subsequently incubated with a 1:20,000 dilution of rabbit anti-PD-L1 antibody (E1L3N, Cell Signaling Technology) for 1 hour at room temperature, washed 3×5 min with TBST, then incubated in a 1:200,000 dilution of anti-rabbit-HRP antibody (AC2114, Azure Biosystems) for 1 hour at room temperature. The membrane was washed 3×5 min with TBST, developed with SuperSignal WestPico substrate (Thermo Fisher Scientific), and imaged with an Azure C600 gel imager (Azure Biosystems).

Example 2. Second-Generation PD-L1 Ligands

Second-generation peptide ligands that bind human PD-L1 were identified using a synthesized DNA library based on the peptide sequence MPIFLDHILNKFWILHYA (SEQ ID NO: 3) (Kamalinia, et. al. (2020) ACS Chem. Biol. 15(6), 1630-1641). The library was designed to encode a peptide library of the form:

```
                                    (SEQ ID NO: 140)
        MXXXXDHILNKFWILHYAXXXX
``` where X is any of the 20 natural amino acids and the underlined amino acids were doped at the nucleotide-level such that each nucleotide is 70% of the wildtype nucleotide and 10% of each of the other nucleotides. At the amino acid level, this produces a wildtype frequency of roughly 30-50%, depending on the amino acid.

An mRNA display fusion library was generated in vitro (Takahashi, et al. (2009) Methods Mol Biol 535: 293-314) and incubated with human PD-L1 immobilized via biotin on neutravidin agarose beads (Thermo Fisher) for 1 hour. Selection was done for seven rounds with the following conditions:

1. 300 pmol biotinylated PD-L1, 4° C.
2. 100 pmol biotinylated PD-L1, 4° C.
3. 50 pmol biotinylated PD-L1, 22° C.
4. 50 pmol biotinylated PD-L1, 22° C.
5. 25 pmol biotinylated PD-L1, 22° C.
6. off-rate competition with 100X non-biotinylated PD-L1 for 15 min, 4° C.
7. off-rate competition with 100X non-biotinylated PD-L1 for 15 hr, 4° C.

Higher temperature and lower target concentration increase the stringency of selection for higher affinity sequences. The off-rate competition (similar to that performed in Boder et al., Wittrup, Proc Natl Acad Sci USA (2000), 97:10701-5.) also aimed to increase the stringency of selection for higher affinity sequences, as any bound clone that dissociated from target would then bind to free non-biotinylated target in solution and be removed during the bead washing step.

For each round of selection, the percent binding of the pool (counts bound to beads divided by total counts added to the reaction) was measured using a radioactive binding assay in binding buffer (20 mM HEPES-KOH, pH 7.5; 150 mM NaCl; 0.2% (v/v) Tween-20; 1 mg/mL BSA; 50 μg/mL bovine tRNA; 0.02 mM biotin). Fusions were radiolabeled by translating the peptides with 35S-methionine followed by purification. Fusions were then incubated with 100 pmol of biotinylated human PD-L1 immobilized on neutravidin agarose beads at 4° C. After an hour, the sample was centrifuged and washed three times to remove unbound fusions from the beads. The radioactive counts were measured in the supernatant, washes, and beads using a scintillation counter. The percent binding of the pool was calculated as beads/(total counts; i.e., beads+supernatant+wash). As a control to measure non-target binding, the experiment was repeated with neutravidin agarose beads containing no target and blocked with biotin. Binding was also measured at 22° C. and 50 pmol for pools 2 and 3 and at 22° C. and 25 pmol for Pools 4, 6, and 7 (FIG. 13).

Example 3. Characterization of Second-Generation
PD-L1 Ligands

DNA from the last pool was cloned via a TOPO kit
(Thermo Fisher), after which plasmid DNA was transformed
into XL10G bacteria, and grown on LB ampicillin agar
plates overnight. Colonies were picked for overnight culture
in LB ampicillin then plasmid was purified using MiniPrep
DNA kits (Macherey-Nagel) for Sanger sequencing.

DNA from several pools were also sequenced using
High-Throughput Sequencing techniques (i.e., Illumina).
Adapters were added to DNA from the last six pools via
PCR for next generation sequencing (Illumina).

Lead sequences identified from Sanger sequencing and
Illumina sequencing are shown below compared to the
wildtype sequence. Sequences from the last pool identified
from Illumina sequencing are also summarized below by
position.

The sequences resulting from the Illumina pool were
processed using homemade Python scripts, which pro-
cessed, translated, and counted the frequency of each
sequence. These peptide sequences were then arranged in
order of decreasing frequency. In general, higher frequency
sequences show higher activity in activity assays (see Olson
et al., Angew. Chem. Int'l Ed., (2012), 51, 12449-453).

Position 12: F
Position 13: F, L, W, Y
Position 14: I
Position 15: L, M
Position 16: H
Position 17: E, F, N, Y
Position 18: A, S, T
Position 19: A, F, H, I, K, M, N, Q, R, S, T, V
Position 20: H, K, L, N, Q, R, S, T, Y
Position 21: A, G, H, K, N, P, Q, R, S, T
Position 22: A, D, I, K, L, N, Q, S, T Several lead sequences (Table 4) were identified from Illu-
mina sequencing:

```
1)
                                   (SEQ ID NO: 141)
MYTDADHILNKFLIMHYARNQQ, 3)
                                   (SEQ ID NO: 142)
 MYTQTDHTLNKFLIMHEAFNST,
```

TABLE 4

Identified lead sequences.

| | # | Sequence | 1 | 2 | 3 | 4 | 5 | 6 | 7 | 8 | 9 | 10 | 11 | 12 | 13 | 14 | 15 | 16 | 17 | 18 | 19 | 20 | 21 | 22 | SEQ ID NO |
|---|---|---|---|---|---|---|---|---|---|---|---|----|----|----|----|----|----|----|----|----|----|----|----|----|----|
| Illumina | 1 | MYTDADH1LNKFLIMHYARNQQ | M | Y | T | D | A | D | H | I | L | N | K | F | L | I | M | H | Y | A | R | N | Q | Q | 141 |
| | 3 | MYTQTDHTLNKFLIMHEAFNST | M | Y | T | Q | T | D | H | T | L | N | K | F | L | I | M | H | E | A | F | N | S | T | 142 |
| | 5 | MYSLNDHNLNKFWILHFAVNQM | M | Y | S | L | N | D | H | N | L | N | K | F | W | I | L | H | F | A | V | N | Q | M | 143 |
| | 6 | MYTSTDHILNKFLILHESLQST | M | Y | T | S | T | D | H | I | L | N | K | F | L | I | L | H | E | S | L | Q | S | T | 144 |
| | 7 | MWSRSDHNLNKFWILHYSANPS | M | W | S | R | S | D | H | N | L | N | K | F | W | I | L | H | Y | S | A | N | P | S | 145 |
| | 8 | MYSRVDHNLNKFWILHQALKSN | M | Y | S | R | V | D | H | N | L | N | K | F | W | I | L | H | Q | A | L | K | S | N | 146 |
| | 9 | MKHSTDHVLNKFYIMHYTANPN | M | K | H | S | T | D | H | V | L | N | K | F | Y | I | M | H | Y | T | A | N | P | N | 147 |
| Sanger | A | MYTLTDHILNKFWIMHYARNPT | M | Y | T | L | T | D | H | I | L | N | K | F | W | I | M | H | Y | A | R | N | P | T | 148 |
| | B | MYSHNDHNLNKFWILHFAVNQM | M | Y | s | H | N | D | H | N | L | N | K | F | W | I | L | H | F | A | V | N | Q | M | 149 |
| | C | MEFTSDHSLNKFIILHYANNPF | M | E | F | T | S | D | H | S | L | N | K | F | I | I | L | H | Y | A | N | N | P | F | 150 |
| | D | MWSITDHNLNKFWILHYATKHG | M | W | s | I | T | D | H | N | L | N | K | F | W | I | L | H | Y | A | T | K | H | G | 151 |
| | S | MPIFLDHILNKFWILHYA | M | P | I | F | L | D | H | I | L | N | K | F | W | I | L | H | Y | A | | | | | 28 |

In the top 500 sequences, we observed the following resi-
dues:

Position 1: M
Position 2: E, F, W, Y
Position 3: F, K, S, T
Position 4: D, H, K, L, N, Q, R, S, T
Position 5: A, F, S, T
Position 6: D
Position 7: H
Position 8: I, N, S, T, V
Position 9: L
Position 10: N
Position 11: K

```
 -continued
5)
                                   (SEQ ID NO: 143)
MYSLNDHNLNKFWILHFAVNQM, 6)
                                   (SEQ ID NO: 144)
MYTSTDHILNKFLILHESLQST, 7)
                                   (SEQ ID NO: 145)
MWSRSDHNLNKFWILHYSANPS, 8)
                                   (SEQ ID NO: 146)
MYSRVDHNLNKFWILHQALKSN,
```

-continued

```
9)
                                    (SEQ ID NO: 147)
MKHSTDHVLNKFYIMHYTANPN,
``` and from Sanger sequencing:

```
A)
                                    (SEQ ID NO: 148)
MYTLTDHILNKFWIMHYARNPT,

B)
                                    (SEQ ID NO: 149)
MYSHNDHNLNKFWILHFAVNQM,

C)
                                    (SEQ ID NO: 150)
MEFTSDHSLNKFIILHYANNPF,
and D)
                                    (SEQ ID NO: 151)
MWSITDHNLNKFWILHYATKHG.
```

As a control, the wildtype sequence (S) MPIFL-DHILNKFWILHYA (SEQ ID NO: 28) was also included for further study.

To test these sequences, the above radioactive binding assay used to characterize the pool binding was also used to characterize individual clone binding. The percent binding for these sequences was tested at 22° C. with 0, 2.5, and 12.5 pmol biotinylated PD-L1 in order to create even more stringent conditions to separate high and even higher affinity sequences.

The binding data are show in FIG. 14. All of the sequences that were tested were observed to bind better than the wildtype SPAM sequence at 2.5 and 12.5 μmol, indicating that selection for higher affinity second-generation PD-L1 binding sequences was successful.

The frequency of peptides A, B, C, and D (which were originally identified by Sanger sequencing of the final pool) in the list of peptide sequences generated by Illumina sequencing was determined. Peptides B, C and D have frequency values of 38, 3988 and 285 parts per million (PPM) sequences, respectively while peptides A was not found in the Illumina dataset. The fact that even sequences that occur at low frequency (e.g., Peptide C) or are not found in the Illumina dataset at all (peptide A has a frequency value of <1 PPM) show comparable binding to the most frequent sequences (FIG. 14), suggests that it is likely that intermediate frequency sequences are also functional for binding to hPD-L1 and likely show comparable binding activity.

The sequences identified from Sanger sequencing (A,B, C,D) were tested under binding conditions modified to be similar to physiological conditions and compared to the wildtype sequence (S) (FIG. 14). Sequences were prepared as fusions in standard blocking buffer, as RNase-treated fusions (RNase A treatment for 30 min. at 37° C.) in standard blocking buffer, or as RNase-treated fusions in 25% human serum in DMEM. Binding was measured at 22° C. with 0 and 25 pmol biotinylated PD-L1.

RNase treatment caused a slight decrease (~$10^{-15}$%) in binding for all sequences, but peptides A, B, C, and D all still show significant net binding, especially when compared to S. The lack of a large change indicates that the mRNA part of the fusions does not influence binding (e.g., the mRNA is involved in binding to PD-L1).

Likewise, binding in serum also caused a slightly larger decrease in binding for all sequences (–20-25%), but again peptides A, B, C, and D all still show significant net binding, especially when compared to S. These data also indicate that the addition of human serum does not significantly change the binding of these peptides, indicating that these peptides are relatively stable against modification by human serum (e.g., degradation by proteases) (FIG. 15). All sequences identified from Illumina sequencing appear more frequently in the final pool than any of the sequences from Sanger sequencing.

Example 4. Pharmaceutical Dosage Forms

The following formulations illustrate representative pharmaceutical dosage forms that may be used for the therapeutic or prophylactic administration of a peptide or peptide composition described herein or a composition specifically disclosed herein (hereinafter referred to as 'Composition X'):

|  | mg/tablet |
| --- | --- |
| (i) Tablet 1 | |
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

|  | mg/mL |
| --- | --- |
| (iv) Injection 1 (1 mg/mL) | |
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/mL) | |
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
| --- | --- |
| 'Composition X' | 20 |
| Oleic acid | 10 |
| Trichloromonofluoromethane | 5,000 |

-continued

| Dichlorodifluoromethane | 10,000 |
| Dichlorotetrafluoroethane | 5,000 |

| | wt. % |
| --- | --- |
| (vii) Topical Gel 1 | |
| 'Composition X' | 5% |
| Carbomer 934 | 1.25% |
| Triethanolamine | q.s. |
| (pH adjustment to 5-7) | |
| Methyl paraben | 0.2% |
| Purified water | q.s. to 100 g |
| (viii) Topical Gel 2 | |
| 'Composition X' | 5% |
| Methylcellulose | 2% |
| Methyl paraben | 0.2% |
| Propyl paraben | 0.02% |
| Purified water | q.s. to 100 g |
| (ix) Topical Ointment | |
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |
| (x) Topical Cream 1 | |
| 'Composition X' | 5% |
| White bees wax | 10% |
| Liquid paraffin | 30% |
| Benzyl alcohol | 5% |
| Purified water | q.s. to 100 g |
| (xi) Topical Cream 2 | |
| 'Composition X' | 5% |
| Stearic acid | 10% |
| Glyceryl monostearate | 3% |

-continued

| Polyoxyethylene stearyl ether | 3% |
| --- | --- |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A peptide that binds to human Programmed Death Ligand 1 (PD-L1), wherein the peptide comprises the sequence M-$X_1$-$X_2$-$X_3$-$X_4$-D-H-$X_5$-L-N-K-F-$X_6$-I-$X_7$-H-$X_8$-$X_9$-$X_{10}$-$X_{11}$-$X_{12}$-$X_{13}$ (SEQ ID NO: 170), wherein:

$X_1$ is E, F, K, W, or Y;
$X_2$ is F, H, K, S, or T;
$X_3$ is D, H, K, L, I, N, Q, R, S, or T;
$X_4$ is A, F, S, N, V, or T;
$X_5$ is I, N, S, T, or V;
$X_6$ is F, L, I, W, or Y;
$X_7$ is L or M;
$X_8$ is E, F, N, Q, or Y;
$X_9$ is A, S, or T;
$X_{10}$ is A, F, H, I, K, L, M, N, Q, R, S, T, or V;
$X_{11}$ is H, K, L, N, Q, R, S, T, or Y;
$X_{12}$ is A, G, H, K, N, P, Q, R, S, or T; and
$X_{13}$ is A, D, F, G, I, K, L, M, N, Q, S, or T.

2. The peptide of claim 1, wherein $X_1$ is E, K, W, or Y; $X_2$ is F, H, S, or T; $X_3$ is D, Q, L, S, R, H, T, or I; $X_4$ is A, S, N, V, or T; $X_5$ is I, N, S, T, or V; $X_6$ is F, L, I, W, or Y; $X_7$ is L or M; $X_8$ is E, F, Q, or Y; $X_9$ is A, S, or T; $X_{10}$ is A, F, L, N, R, T, or V; $X_{11}$ is N, Q, or K; $X_{12}$ is H, P, Q, or S; and $X_{13}$ is F, G, N, Q, M, S, or T (SEQ ID NO: 171).

3. The peptide of claim 1, wherein the peptide comprises an amino acid sequence 90% identical to any one of SEQ ID NO: 141-151.

4. The peptide according to claim 3, wherein the peptide comprises an amino acid sequence identical to any one of SEQ ID NO: 141-151.

5. The peptide according to claim 4, wherein the peptide comprises an amino acid sequence identical to SEQ ID NO: 143, SEQ ID NO: 144, SEQ ID NO: 145, SEQ ID NO: 148, or SEQ ID NO: 149.

6. The peptide of claim 1 further comprising a secondary molecule conjugated to the peptide.

7. The peptide of claim 6, wherein the secondary molecule is a diagnostic agent.

8. The peptide of claim 7, wherein the diagnostic agent comprises one or more of a radiolabel, a fluorescein or fluorescein analog, Carboxy-X-rhodamine, biotin, hemagglutinin, or [18]F.

9. The peptide of claim 6, wherein the secondary molecule comprises a cytotoxic agent or radionuclide.

10. The peptide of claim 9, wherein the cytotoxic agent is one or more of paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

11. The peptide of claim 9, wherein the radionuclide comprises one or more of $^{90}$Y, $^{131}$I, $^{177}$Lu, [153]Sm, [186]Re, [188]Re, [67]Cu, [225]Ac, [213]Bi, [212]Bi, [211]At, [212]Pb, and [125]I.

12. The peptide of claim 1, wherein the peptide comprises a molecular weight of about 2500 Da to about 3400 Da.

13. A composition comprising the peptide of claim 1 and a pharmaceutically acceptable carrier.

14. A peptide that binds to Programmed Death Ligand 1 (PD-L1), wherein the peptide comprises an amino acid sequence that is 90% identical to MPIFL-DHILNKFWILHYA (SEQ ID NO: 3).

15. The peptide of claim 14 wherein the protein binds to human hPD-L1 with a dissociation constant ($K_D$) of about 119 nM and to an extracellular domain of hPD-L1 with a $K_D$ of about 67 nM.

16. The peptide of claim 14 wherein the amino acid sequence of the peptide is MPIFLDHILNKFWILHYA (SEQ ID NO: 3).

17. The peptide of claim 14, wherein the peptide is conjugated to a cytotoxic agent comprising one or more of paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, or a radionuclide comprises one or more of $^{90}$Y, $^{131}$I, $^{177}$Lu, $^{153}$Sm, $^{186}$Re, $^{188}$Re, $^{67}$Cu, $^{225}$Ac, $^{213}$Bi $^{212}$Bi, $^{211}$At $^{212}$Pb, and $^{125}$I.

18. The peptide of claim 14, further comprising a radiolabel, a fluorescein or fluorescein analog, Carboxy-X-rhodamine, biotin, hemagglutinin, or $^{18}$F.

19. A method of treating a cancer in a subject wherein the PD-L1 protein is overexpressed on a cell surface of a cancer cell comprising:

administering an effective amount of the composition of claim 18 to the subject, thereby treating the cancer.

20. The method of claim 19 wherein the cancer is one or more of melanoma, renal cell carcinoma (RCC), non-small cell lung cancer (NSCLC), small cell lung cancer (SCLC), metastatic Merkel cell carcinoma, bladder, head and neck, cervical, urothelial, glioblastoma multiforme, breast, triple-negative breast, gastric, esophageal, hepatocellular carcinoma, pancreatic, colorectal, thymic, ovarian, sarcoma, acute myeloid leukemia, B-cell lymphomas, and multiple myeloma.

\* \* \* \* \*

SEQUENCE LISTING

```
<160> NUMBER OF SEQ ID NOS: 182

<210> SEQ ID NO 1
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: An aliphatic amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (12)..(12)
<223> OTHER INFORMATION: An aromatic amino acid
<220> FEATURE:
<221> NAME/KEY: MOD_RES
<222> LOCATION: (14)..(14)
```

```
<223> OTHER INFORMATION: Any amino acid
<220> FEATURE:
<221> NAME/KEY: MOD_RES
<222> LOCATION: (16)..(17)
<223> OTHER INFORMATION: Any amino acid

<400> SEQUENCE: 1

Met Xaa Ile Phe Xaa Xaa Xaa Ile Xaa Xaa Xaa Xaa Trp Xaa Leu Xaa
1               5                   10                  15

Xaa Ala

<210> SEQ ID NO 2
<211> LENGTH: 18
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala

<210> SEQ ID NO 3
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Met Pro Ile Phe Leu Asp His Ile Leu Asn Lys Phe Trp Ile Leu His
1               5                   10                  15

Tyr Ala

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Met Ile Phe Leu Asp His Ile Leu Asn Lys Phe Trp Ile Leu His Tyr
1               5                   10                  15

Ala

<210> SEQ ID NO 5
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Met Phe Leu Asp His Ile Leu Asn Lys Phe Trp Ile Leu His Tyr Ala
1               5                   10                  15

<210> SEQ ID NO 6
<211> LENGTH: 15
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Met Leu Asp His Ile Leu Asn Lys Phe Trp Ile Leu His Tyr Ala
1               5                   10                  15

<210> SEQ ID NO 7
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Met Asp His Ile Leu Asn Lys Phe Trp Ile Leu His Tyr Ala
1               5                   10

<210> SEQ ID NO 8
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (20)..(20)
<223> OTHER INFORMATION: Propargylglycine

<400> SEQUENCE: 8

Met Arg Ile Phe Ala Val Phe Ile Phe Met Thr Tyr Trp His Leu Leu
1               5                   10                  15

Asn Ala Lys Xaa
            20

<210> SEQ ID NO 9
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (21)..(21)
<223> OTHER INFORMATION: Propargylglycine

<400> SEQUENCE: 9

Met Pro Ile Phe Leu Asp His Ile Leu Asn Lys Phe Trp Ile Leu His
1               5                   10                  15

Tyr Ala Ser Gly Xaa
            20

<210> SEQ ID NO 10
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (21)..(21)
<223> OTHER INFORMATION: Propargylglycine

<400> SEQUENCE: 10

Tyr Lys Leu Asn Leu Ile His Pro His Ile Phe Leu Met Asp Trp Ile
1               5                   10                  15

Phe Ala Ser Gly Xaa
            20

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Ser Gly Thr Ser Gly Ser Ser
1               5

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ser Gly Ser Ser Gly His His His His His Ser Ser
1               5                   10

<210> SEQ ID NO 13
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (29)..(30)
<223> OTHER INFORMATION: a, c, t, or g
<220> FEATURE:
<221> NAME/KEY: modified_base
<222> LOCATION: (32)..(33)
<223> OTHER INFORMATION: a, c, t, or g
<220> FEATURE:
<221> NAME/KEY: modified_base
<222> LOCATION: (35)..(36)
<223> OTHER INFORMATION: a, c, t, or g
<220> FEATURE:
<221> NAME/KEY: modified_base
<222> LOCATION: (38)..(39)
<223> OTHER INFORMATION: a, c, t, or g
<220> FEATURE:
<221> NAME/KEY: modified_base
<222> LOCATION: (41)..(42)
<223> OTHER INFORMATION: a, c, t, or g
<220> FEATURE:
<221> NAME/KEY: modified_base
<222> LOCATION: (44)..(45)
<223> OTHER INFORMATION: a, c, t, or g
<220> FEATURE:
<221> NAME/KEY: modified_base
<222> LOCATION: (47)..(48)
```

```
<223> OTHER INFORMATION: a, c, t, or g
<220> FEATURE:
<221> NAME/KEY: modified_base
<222> LOCATION: (50)..(51)
<223> OTHER INFORMATION: a, c, t, or g
<220> FEATURE:
<221> NAME/KEY: modified_base
<222> LOCATION: (53)..(54)
<223> OTHER INFORMATION: a, c, t, or g

<400> SEQUENCE: 13
gggacaatta ctatttacaa taaccatgnn knnsnnsnns nnsnnsnnsn nsnnkggtag       60
tggtacgtct ggctccagc                                                   79

<210> SEQ ID NO 14
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
ggattctaat acgactcact atagggacaa ttactattta caataacc                   48

<210> SEQ ID NO 15
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gctggagcca gacgtaccac tacc                                             24

<210> SEQ ID NO 16
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (29)..(79)
<223> OTHER INFORMATION: a, c, t, or g
<220> FEATURE:
<221> NAME/KEY: source
<223> OTHER INFORMATION: /note="See specification as filed for detailed
      description of substitutions and preferred embodiments"

<400> SEQUENCE: 16
gggacaatta ctatttacaa ttacaatgnn nnnnnnnnnn nnnnnnnnnn nnnnnnnnnn       60
nnnnnnnnnn nnnnnnnnng gatccggttc aagcggtcac                            100

<210> SEQ ID NO 17
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
```

-continued

```
ggattctaat acgactcact atagggacaa ttactattta caattaca                    48

<210> SEQ ID NO 18
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
tgaactatgg tgatgatgat ggtgaccgct tgaaccg                                37

<210> SEQ ID NO 19
<211> LENGTH: 17
<212> TYPE: DNA
<213> ORGANISM: Unknown
<220> FEATURE:
<221> NAME/KEY: source
<223> OTHER INFORMATION: /note="Description of Unknown:
      T7 promoter sequence"

<400> SEQUENCE: 19
taatacgact cactata                                                      17

<210> SEQ ID NO 20
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
acaattacta tttacaatta ca                                                22

<210> SEQ ID NO 21
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ggtagtggta cgtctggctc cagc                                              24

<210> SEQ ID NO 22
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ggatccggtt caagcggtca ccatcatcat caccatagtt ca                          42

<210> SEQ ID NO 23
<211> LENGTH: 21
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 23
aaaaaaaaaa aaaaaaaaaa a                                                  21

<210> SEQ ID NO 24
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24 ttttttttttt tttgaactat ggtg                                            24

<210> SEQ ID NO 25
<211> LENGTH: 290
<212> TYPE: PRT
<213> ORGANISM: Homo sapiens

<400> SEQUENCE: 25

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys

-continued

```
                260              265             270
Gly Ile Gln Asp Thr Asn Ser Lys Lys Gln Ser Asp Thr His Leu Glu
        275              280              285

Glu Thr
    290

<210> SEQ ID NO 26
<211> LENGTH: 222
<212> TYPE: PRT
<213> ORGANISM: Homo sapiens

<400> SEQUENCE: 26

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
            115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
            195                 200                 205

Ile Pro Glu Leu Pro Leu Ala His Pro Pro Asn Glu Arg Thr
    210                 215                 220

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Met Arg Ile Phe Val Ile Phe Ile Trp Ala
1               5                   10

<210> SEQ ID NO 28
<211> LENGTH: 18
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 28

Met Pro Ile Phe Leu Asp His Ile Leu Asn Lys Phe Trp Ile Leu His
1               5                   10                  15

Tyr Ala

<210> SEQ ID NO 29

<400> SEQUENCE: 29

000

<210> SEQ ID NO 30
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Met Pro Ile Phe Leu Asp His Ile Leu Asn Lys Phe Trp Ile Leu His
1               5                   10                  15

Tyr Ala Gly Ser Gly
            20

<210> SEQ ID NO 31
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Met Pro Ile Phe Leu Asp His Val Leu Asn Lys Phe Trp Ile Leu His
1               5                   10                  15

Tyr Ala Gly Ser Gly
            20

<210> SEQ ID NO 32
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Met Pro Ile Phe Leu Asp His Thr Leu Asn Lys Phe Trp Ile Leu His
1               5                   10                  15

Tyr Ala Gly Ser Gly
            20

<210> SEQ ID NO 33
<211> LENGTH: 21
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 33

Met Pro Ile Ser Leu Asp His Ile Leu Asn Lys Phe Trp Ile Leu His
1               5                   10                  15

Tyr Ala Gly Ser Gly
            20

<210> SEQ ID NO 34
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Met Arg Ile Ser Val Asp His Ile Leu Leu Lys Phe Trp Ile Leu His
1               5                   10                  15

Asn Ser Gly Ser Gly
            20

<210> SEQ ID NO 35
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Met Pro Ile Leu Leu Asp His Ile Leu Asn Lys Phe Trp Ile Leu His
1               5                   10                  15

Tyr Ala Gly Ser Gly
            20

<210> SEQ ID NO 36
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Met Pro Ile Phe Gln Asp His Ile Leu Asn Lys Phe Trp Ile Leu His
1               5                   10                  15

Tyr Ala Gly Ser Gly
            20

<210> SEQ ID NO 37
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Met Pro Ile Phe Pro Asp His Ile Leu Asn Lys Phe Trp Ile Leu His
1               5                   10                  15
```

```
Tyr Ala Gly Ser Gly
          20

<210> SEQ ID NO 38
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Met Pro Val Phe Leu Asp His Ile Leu Asn Lys Phe Trp Ile Leu His
1               5                   10                  15

Tyr Ala Gly Ser Gly
          20

<210> SEQ ID NO 39
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Met Gly Thr Phe Tyr Asp His Ile Phe Ile Lys Phe Met Ile Leu His
1               5                   10                  15

Thr Thr Gly Ser Gly
          20

<210> SEQ ID NO 40
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Met Pro Ile Tyr Leu Asp His Ile Leu Asn Lys Phe Trp Ile Leu His
1               5                   10                  15

Tyr Ala Gly Ser Gly
          20

<210> SEQ ID NO 41
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Met Pro Ile Phe Ile Asp His Ile Leu Asn Lys Phe Trp Ile Leu His
1               5                   10                  15

Tyr Ala Gly Ser Gly
          20

<210> SEQ ID NO 42
<211> LENGTH: 21
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Met Pro Met Phe Leu Asp His Ile Leu Asn Lys Phe Trp Ile Leu His
1               5                   10                  15

Tyr Ala Gly Ser Gly
            20

<210> SEQ ID NO 43
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Met Arg Lys Ser Val Asp His Ile Leu Leu Lys Phe Trp Ile Leu His
1               5                   10                  15

Asn Ser Gly Ser Gly
            20

<210> SEQ ID NO 44
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Met Pro Thr Phe Leu Asp His Ile Leu Asn Lys Phe Trp Ile Leu His
1               5                   10                  15

Tyr Ala Gly Ser Gly
            20

<210> SEQ ID NO 45
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Met Pro Ile Phe Leu Asp His Met Leu Asn Lys Phe Trp Ile Leu His
1               5                   10                  15

Tyr Ala Gly Ser Gly
            20

<210> SEQ ID NO 46
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 46

Met Gly Thr Phe Tyr Asp His Ile Phe Ile Lys Phe Met Ile Leu His
1               5                   10                  15

Thr Ala Gly Ser Gly
            20

<210> SEQ ID NO 47
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Met Pro Ile Phe Leu Asp His Ile Leu Asn Lys Phe Trp Ile Leu His
1               5                   10                  15

His Ala Gly Ser Gly
            20

<210> SEQ ID NO 48
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Met Pro Ile Phe Leu Asp His Ile Leu Asn Lys Phe Trp Ile Leu His
1               5                   10                  15

Cys Ala Gly Ser Gly
            20

<210> SEQ ID NO 49
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Met Lys Lys Phe Ser Asp His Thr Leu Met Lys Phe Trp Ile Leu Val
1               5                   10                  15

Asn Ala Gly Ser Gly
            20

<210> SEQ ID NO 50
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Met Pro Ile Phe Leu Asp His Ile Leu Asn Lys Phe Arg Ile Leu His
1               5                   10                  15

Tyr Ala Gly Ser Gly
            20
```

```
<210> SEQ ID NO 51
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Met Pro Ile Phe Leu Asp His Ile Leu Ser Lys Phe Trp Ile Leu His
1               5                   10                  15

Tyr Ala Gly Ser Gly
            20

<210> SEQ ID NO 52
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Met Pro Ile Phe Leu Asp His Ile Leu Asn Lys Phe Trp Ile Pro His
1               5                   10                  15

Tyr Ala Gly Ser Gly
            20

<210> SEQ ID NO 53
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Met Pro Ile Phe Leu Gly His Ile Leu Asn Lys Phe Trp Ile Leu His
1               5                   10                  15

Tyr Ala Gly Ser Gly
            20

<210> SEQ ID NO 54
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Met Pro Ile Phe Leu Asp His Ile Leu Asn Lys Phe Trp Ile Leu Arg
1               5                   10                  15

Tyr Ala Gly Ser Gly
            20

<210> SEQ ID NO 55
<211> LENGTH: 21
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 55

Met Pro Ile Phe Leu Asp His Ile Leu Asp Lys Phe Trp Ile Leu His
1               5                   10                  15

Tyr Ala Gly Ser Gly
            20

<210> SEQ ID NO 56
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Met Pro Ile Phe Leu Asp Arg Ile Leu Asn Lys Phe Trp Ile Leu His
1               5                   10                  15

Tyr Ala Gly Ser Gly
            20

<210> SEQ ID NO 57
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Met Pro Ile Phe Leu Asp His Ile Leu Asn Lys Leu Trp Ile Leu His
1               5                   10                  15

Tyr Ala Gly Ser Gly
            20

<210> SEQ ID NO 58
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Met Leu Ile Phe Leu Asp His Ile Leu Asn Lys Phe Trp Ile Leu His
1               5                   10                  15

Tyr Ala Gly Ser Gly
            20

<210> SEQ ID NO 59
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Met Ser Ile Phe Leu Asp His Ile Leu Asn Lys Phe Trp Ile Leu His

```
1               5               10              15

Tyr Ala Gly Ser Gly
            20

<210> SEQ ID NO 60
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Met Pro Ile Phe Leu Asp His Ile Leu Asn Glu Phe Trp Ile Leu His
1               5               10              15

Tyr Ala Gly Ser Gly
            20

<210> SEQ ID NO 61
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Met Pro Ile Phe Leu Asp His Ile Leu Asn Lys Phe Trp Thr Leu His
1               5               10              15

Tyr Ala Gly Ser Gly
            20

<210> SEQ ID NO 62
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Met Pro Ile Phe Leu Asp His Ile Leu Asn Lys Ser Trp Ile Leu His
1               5               10              15

Tyr Ala Gly Ser Gly
            20

<210> SEQ ID NO 63
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Met Pro Ile Phe Leu Asp His Ile Leu Asn Lys Phe Trp Val Leu His
1               5               10              15

Tyr Ala Gly Ser Gly
            20

<210> SEQ ID NO 64
```

```
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Met Pro Ile Phe Leu Asp His Ile Leu Asn Lys Phe Trp Ile Leu His
1               5                   10                  15

Tyr Thr Gly Ser Gly
            20

<210> SEQ ID NO 65
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Met Pro Leu Phe Leu Asp His Ile Leu Asn Lys Phe Trp Ile Leu His
1               5                   10                  15

Tyr Ala Gly Ser Gly
            20

<210> SEQ ID NO 66
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Met Pro Ile Phe Leu Asp His Ile Pro Asn Lys Phe Trp Ile Leu His
1               5                   10                  15

Tyr Ala Gly Ser Gly
            20

<210> SEQ ID NO 67
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Met Pro Ile Phe Leu Asp His Ile Leu Asn Lys Phe Trp Ile Leu His
1               5                   10                  15

Tyr Asp Gly Ser Gly
            20

<210> SEQ ID NO 68
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 68

Met Pro Ile Phe Leu Asp His Ile Leu Asn Arg Phe Trp Ile Leu His
1               5                   10                  15

Tyr Ala Gly Ser Gly
          20

<210> SEQ ID NO 69
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Met Pro Lys Phe Leu Asp His Ile Leu Asn Lys Phe Trp Ile Leu His
1               5                   10                  15

Tyr Ala Gly Ser Gly
          20

<210> SEQ ID NO 70
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Met Pro Ile Phe Leu Asp His Ile Leu Asn Lys Phe Trp Ile Leu His
1               5                   10                  15

Phe Ala Gly Ser Gly
          20

<210> SEQ ID NO 71
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Met Pro Ile Phe Leu Asp His Ile Leu Asn Lys Phe Trp Ile Leu Tyr
1               5                   10                  15

Tyr Ala Gly Ser Gly
          20

<210> SEQ ID NO 72
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Met Pro Ile Phe Leu Asp Tyr Ile Leu Asn Lys Phe Trp Ile Leu His
1               5                   10                  15

Tyr Ala Gly Ser Gly

20

<210> SEQ ID NO 73
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Met Pro Ile Ile Leu Asp His Ile Leu Asn Lys Phe Trp Ile Leu His
1               5                   10                  15

Tyr Ala Gly Ser Gly
            20

<210> SEQ ID NO 74
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Met Pro Ile Phe Val Asp His Ile Leu Asn Lys Phe Trp Ile Leu His
1               5                   10                  15

Tyr Ala Gly Ser Gly
            20

<210> SEQ ID NO 75
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Met Pro Ile Phe Leu Asp His Ile Leu Asn Lys Phe Trp Ile Leu His
1               5                   10                  15

Asn Ala Gly Ser Gly
            20

<210> SEQ ID NO 76
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Met Pro Ile Phe Leu Asp His Leu Leu Asn Lys Phe Trp Ile Leu His
1               5                   10                  15

Tyr Ala Gly Ser Gly
            20

<210> SEQ ID NO 77
<211> LENGTH: 21
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 77

Met Pro Ile Phe Leu Asp His Ile Leu Asn Lys Phe Trp Ile Leu His
1               5                   10                  15

Tyr Val Gly Ser Gly
            20

<210> SEQ ID NO 78
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Met Pro Ile Ser Leu Asp His Val Leu Asn Lys Phe Trp Ile Leu His
1               5                   10                  15

Tyr Ala Gly Ser Gly
            20

<210> SEQ ID NO 79
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Met Pro Ile Phe Leu Asp Leu Ile Leu Asn Lys Phe Trp Ile Leu His
1               5                   10                  15

Tyr Ala Gly Ser Gly
            20

<210> SEQ ID NO 80
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Met Pro Ile Phe Leu Asn His Ile Leu Asn Lys Phe Trp Ile Leu His
1               5                   10                  15

Tyr Ala Gly Ser Gly
            20

<210> SEQ ID NO 81
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81
```

-continued

```
Met Pro Ile Phe Leu Asp His Ile Leu Asn Lys Phe Trp Ile Phe His
1               5                   10                  15

Tyr Ala Gly Ser Gly
            20

<210> SEQ ID NO 82
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Met Pro Ile Leu Leu Asp His Val Leu Asn Lys Phe Trp Ile Leu His
1               5                   10                  15

Tyr Ala Gly Ser Gly
            20

<210> SEQ ID NO 83
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Met Arg Arg Ser Val Asp His Ile Leu Leu Lys Phe Trp Ile Leu His
1               5                   10                  15

Asn Ser Gly Ser Gly
            20

<210> SEQ ID NO 84
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Met Pro Ile Phe Leu Asp His Ile Leu Asn Lys Phe Leu Ile Leu His
1               5                   10                  15

Tyr Ala Gly Ser Gly
            20

<210> SEQ ID NO 85
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Met Pro Ile Ser Leu Asp His Thr Leu Asn Lys Phe Trp Ile Leu His
1               5                   10                  15

Tyr Ala Gly Ser Gly
            20
```

-continued

<210> SEQ ID NO 86
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Met Pro Ile Phe Leu Asp His Ile Leu Tyr Lys Phe Trp Ile Leu His
1               5                   10                  15

Tyr Ala Gly Ser Gly
            20

<210> SEQ ID NO 87
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Met Gln Ile Phe Leu Asp His Ile Leu Asn Lys Phe Trp Ile Leu His
1               5                   10                  15

Tyr Ala Gly Ser Gly
            20

<210> SEQ ID NO 88
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Met Pro Ile Phe Leu Asp His Ile Leu Asn Lys Phe Trp Ile His His
1               5                   10                  15

Tyr Ala Gly Ser Gly
            20

<210> SEQ ID NO 89
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Met Pro Ile Leu Leu Asp His Thr Leu Asn Lys Phe Trp Ile Leu His
1               5                   10                  15

Tyr Ala Gly Ser Gly
            20

<210> SEQ ID NO 90
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 90

Met Pro Ile Phe Leu Asp His Ile Leu Thr Lys Phe Trp Ile Leu His
1               5                   10                  15

Tyr Ala Gly Ser Gly
            20

<210> SEQ ID NO 91
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Met Arg Ile Phe Leu Asp His Ile Leu Asn Lys Phe Trp Ile Leu His
1               5                   10                  15

Tyr Ala Gly Ser Gly
            20

<210> SEQ ID NO 92
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Met Pro Ile Phe Leu Asp His Ile Leu Asn Lys Phe Trp Ile Leu Leu
1               5                   10                  15

Tyr Ala Gly Ser Gly
            20

<210> SEQ ID NO 93
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Met Arg Thr Ser Val Asp His Ile Leu Leu Lys Phe Trp Ile Leu His
1               5                   10                  15

Asn Ser Gly Ser Gly
            20

<210> SEQ ID NO 94
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Met Pro Ile Phe Leu Asp His Ile Leu Asn Lys Phe Trp Ile Leu His
1               5                   10                  15

```
Tyr Ser Gly Ser Gly
            20

<210> SEQ ID NO 95
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Met Pro Ile Phe Leu Asp His Ala Leu Asn Lys Phe Trp Ile Leu His
1               5                   10                  15

Tyr Ala Gly Ser Gly
            20

<210> SEQ ID NO 96
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Met Pro Ile Phe Leu Asp His Ile Leu Asn Lys Phe Cys Ile Leu His
1               5                   10                  15

Tyr Ala Gly Ser Gly
            20

<210> SEQ ID NO 97
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Met Pro Ile Phe Leu Asp His Ile Leu Asn Lys Phe Trp Ile Leu His
1               5                   10                  15

Tyr Gly Gly Ser Gly
            20

<210> SEQ ID NO 98
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Met Pro Ile Phe Leu Asp His Ile Leu Ile Lys Phe Trp Ile Leu His
1               5                   10                  15

Tyr Ala Gly Ser Gly
            20

<210> SEQ ID NO 99
<211> LENGTH: 21
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Met Pro Ile Phe Leu Asp His Lys Leu Asn Lys Phe Trp Ile Leu His
1               5                   10                  15

Tyr Ala Gly Ser Gly
            20

<210> SEQ ID NO 100
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Met Thr Ile Phe Leu Asp His Ile Leu Asn Lys Phe Trp Ile Leu His
1               5                   10                  15

Tyr Ala Gly Ser Gly
            20

<210> SEQ ID NO 101
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Met Arg Ile Ser Val Asp His Ile Leu Leu Lys Phe Trp Ile Leu His
1               5                   10                  15

Asp Ser Gly Ser Gly
            20

<210> SEQ ID NO 102
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Met Pro Ile Phe Leu Asp His Ile Leu Asn Lys Tyr Trp Ile Leu His
1               5                   10                  15

Tyr Ala Gly Ser Gly
            20

<210> SEQ ID NO 103
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

```
Met Pro Arg Phe Leu Asp His Ile Leu Asn Lys Phe Trp Ile Leu His
1               5                   10                  15

Tyr Ala Gly Ser Gly
            20

<210> SEQ ID NO 104
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Met Arg Ile Pro Val Asp His Ile Leu Leu Lys Phe Trp Ile Leu His
1               5                   10                  15

Asn Ser Gly Ser Gly
            20

<210> SEQ ID NO 105
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Met Lys Lys Phe Thr Asp His Thr Leu Met Lys Phe Trp Ile Leu Val
1               5                   10                  15

Asn Ala Gly Ser Gly
            20

<210> SEQ ID NO 106
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Met Pro Ile Phe Leu Val His Ile Leu Asn Lys Phe Trp Ile Leu His
1               5                   10                  15

Tyr Ala Gly Ser Gly
            20

<210> SEQ ID NO 107
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Met Pro Ile Phe Leu Asp His Ile Gln Asn Lys Phe Trp Ile Leu His
1               5                   10                  15

Tyr Ala Gly Ser Gly
            20
```

```
<210> SEQ ID NO 108
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Met Ala Ile Phe Leu Asp His Ile Leu Asn Lys Phe Trp Ile Leu His
1               5                   10                  15

Tyr Ala Gly Ser Gly
            20

<210> SEQ ID NO 109
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Met Lys Lys Phe Leu Asp His Thr Leu Met Lys Phe Trp Ile Leu Val
1               5                   10                  15

Asn Ala Gly Ser Gly
            20

<210> SEQ ID NO 110
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Met Pro Ile Phe Leu Glu His Ile Leu Asn Lys Phe Trp Ile Leu His
1               5                   10                  15

Tyr Ala Gly Ser Gly
            20

<210> SEQ ID NO 111
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Met Pro Ile Phe Pro Asp His Val Leu Asn Lys Phe Trp Ile Leu His
1               5                   10                  15

Tyr Ala Gly Ser Gly
            20

<210> SEQ ID NO 112
<211> LENGTH: 21
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 112

Met Pro Ile Phe Leu Asp His Ile Leu Asn Lys Phe Trp Ile Leu Asn
1               5                   10                  15

Tyr Ala Gly Ser Gly
            20

<210> SEQ ID NO 113
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Met Pro Ile Phe Leu Asp His Ile Leu His Lys Phe Trp Ile Leu His
1               5                   10                  15

Tyr Ala Gly Ser Gly
            20

<210> SEQ ID NO 114
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Met Pro Ile Phe Arg Asp His Ile Leu Asn Lys Phe Trp Ile Leu His
1               5                   10                  15

Tyr Ala Gly Ser Gly
            20

<210> SEQ ID NO 115
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Met Pro Ile Phe Leu Asp His Ile Leu Asn Lys Phe Ser Ile Leu His
1               5                   10                  15

Tyr Ala Gly Ser Gly
            20

<210> SEQ ID NO 116
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Met Gly Thr Ser Tyr Asp His Ile Phe Ile Lys Phe Met Ile Leu His
1               5                   10                  15

Thr Thr Gly Ser Gly
          20

<210> SEQ ID NO 117
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Met Pro Ile Pro Leu Asp His Ile Leu Asn Lys Phe Trp Ile Leu His
1               5                   10                  15

Tyr Ala Gly Ser Gly
          20

<210> SEQ ID NO 118
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Met Pro Ile Val Leu Asp His Ile Leu Asn Lys Phe Trp Ile Leu His
1               5                   10                  15

Tyr Ala Gly Ser Gly
          20

<210> SEQ ID NO 119
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Met Arg Ile Ser Val Asp His Val Leu Leu Lys Phe Trp Ile Leu His
1               5                   10                  15

Asn Ser Gly Ser Gly
          20

<210> SEQ ID NO 120
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Met Pro Ile Phe Leu Tyr His Ile Leu Asn Lys Phe Trp Ile Leu His
1               5                   10                  15

Tyr Ala Gly Ser Gly
          20

<210> SEQ ID NO 121
<211> LENGTH: 21

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Met Pro Ile Phe Leu Asp His Ile Leu Asn Lys Phe Trp Asn Leu His
1               5                   10                  15

Tyr Ala Gly Ser Gly
            20

<210> SEQ ID NO 122
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Met Arg Ile Ser Val Asp His Thr Leu Leu Lys Phe Trp Ile Leu His
1               5                   10                  15

Asn Ser Gly Ser Gly
            20

<210> SEQ ID NO 123
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Met Pro Ile Phe Pro Asp His Thr Leu Asn Lys Phe Trp Ile Leu His
1               5                   10                  15

Tyr Ala Gly Ser Gly
            20

<210> SEQ ID NO 124
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Met Pro Ile Ser Pro Asp His Ile Leu Asn Lys Phe Trp Ile Leu His
1               5                   10                  15

Tyr Ala Gly Ser Gly
            20

<210> SEQ ID NO 125
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 125

Met Pro Val Phe Leu Asp His Val Leu Asn Lys Phe Trp Ile Leu His
1               5                   10                  15

Tyr Ala Gly Ser Gly
            20

<210> SEQ ID NO 126
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Met Pro Thr Ser Leu Asp His Ile Leu Asn Lys Phe Trp Ile Leu His
1               5                   10                  15

Tyr Ala Gly Ser Gly
            20

<210> SEQ ID NO 127
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Met Pro Ile Phe Leu Asp His Ile Leu Asn Lys Phe Trp Ile Leu His
1               5                   10                  15

Tyr Pro Gly Ser Gly
            20

<210> SEQ ID NO 128
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Met Pro Ile Phe Leu Asp His Ile Leu Asn Lys Phe Trp Ile Ile His
1               5                   10                  15

Tyr Ala Gly Ser Gly
            20

<210> SEQ ID NO 129
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Met Pro Ile Phe Leu Asp His Ile Leu Asn Asn Phe Trp Ile Leu His
1               5                   10                  15

Tyr Ala Gly Ser Gly
            20
```

-continued

```
<210> SEQ ID NO 130
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Met Pro Ile Phe Leu Asp Asn Ile Leu Asn Lys Phe Trp Ile Leu His
1               5                   10                  15

Tyr Ala Gly Ser Gly
            20

<210> SEQ ID NO 131
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Met Pro Thr Phe Leu Asp His Thr Leu Asn Lys Phe Trp Ile Leu His
1               5                   10                  15

Tyr Ala Gly Ser Gly
            20

<210> SEQ ID NO 132
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Met Pro Thr Phe Leu Asp His Val Leu Asn Lys Phe Trp Ile Leu His
1               5                   10                  15

Tyr Ala Gly Ser Gly
            20

<210> SEQ ID NO 133
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Met Pro Ile Phe Leu Asp Gln Ile Leu Asn Lys Phe Trp Ile Leu His
1               5                   10                  15

Tyr Ala Gly Ser Gly
            20

<210> SEQ ID NO 134
<211> LENGTH: 21
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 134

Met Pro Met Phe Leu Asp His Thr Leu Asn Lys Phe Trp Ile Leu His
1               5                   10                  15

Tyr Ala Gly Ser Gly
            20

<210> SEQ ID NO 135
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Met Gln Ile Ser Val Asp His Ile Leu Leu Lys Phe Trp Ile Leu His
1               5                   10                  15

Asn Ser Gly Ser Gly
            20

<210> SEQ ID NO 136
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Met Pro Ile Phe Leu Asp His Ile Leu Asn Lys Phe Trp Phe Leu His
1               5                   10                  15

Tyr Ala Gly Ser Gly
            20

<210> SEQ ID NO 137
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Met Pro Met Phe Leu Asp His Val Leu Asn Lys Phe Trp Ile Leu His
1               5                   10                  15

Tyr Ala Gly Ser Gly
            20

<210> SEQ ID NO 138

<400> SEQUENCE: 138

000

<210> SEQ ID NO 139

<400> SEQUENCE: 139

000

```
<210> SEQ ID NO 140
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(5)
<223> OTHER INFORMATION: Any natural amino acid
<220> FEATURE:
<221> NAME/KEY: MOD_RES
<222> LOCATION: (19)..(22)
<223> OTHER INFORMATION: Any natural amino acid

<400> SEQUENCE: 140

Met Xaa Xaa Xaa Xaa Asp His Ile Leu Asn Lys Phe Trp Ile Leu His
1               5                   10                  15

Tyr Ala Xaa Xaa Xaa Xaa
            20

<210> SEQ ID NO 141
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Met Tyr Thr Asp Ala Asp His Ile Leu Asn Lys Phe Leu Ile Met His
1               5                   10                  15

Tyr Ala Arg Asn Gln Gln
            20

<210> SEQ ID NO 142
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Met Tyr Thr Gln Thr Asp His Thr Leu Asn Lys Phe Leu Ile Met His
1               5                   10                  15

Glu Ala Phe Asn Ser Thr
            20

<210> SEQ ID NO 143
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Met Tyr Ser Leu Asn Asp His Asn Leu Asn Lys Phe Trp Ile Leu His
1               5                   10                  15

Phe Ala Val Asn Gln Met
```

-continued

```
                20

<210> SEQ ID NO 144
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Met Tyr Thr Ser Thr Asp His Ile Leu Asn Lys Phe Leu Ile Leu His
1               5                   10                  15

Glu Ser Leu Gln Ser Thr
            20

<210> SEQ ID NO 145
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Met Trp Ser Arg Ser Asp His Asn Leu Asn Lys Phe Trp Ile Leu His
1               5                   10                  15

Tyr Ser Ala Asn Pro Ser
            20

<210> SEQ ID NO 146
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Met Tyr Ser Arg Val Asp His Asn Leu Asn Lys Phe Trp Ile Leu His
1               5                   10                  15

Gln Ala Leu Lys Ser Asn
            20

<210> SEQ ID NO 147
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Met Lys His Ser Thr Asp His Val Leu Asn Lys Phe Tyr Ile Met His
1               5                   10                  15

Tyr Thr Ala Asn Pro Asn
            20

<210> SEQ ID NO 148
<211> LENGTH: 22
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 148

Met Tyr Thr Leu Thr Asp His Ile Leu Asn Lys Phe Trp Ile Met His
1               5                   10                  15

Tyr Ala Arg Asn Pro Thr
            20

<210> SEQ ID NO 149
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Met Tyr Ser His Asn Asp His Asn Leu Asn Lys Phe Trp Ile Leu His
1               5                   10                  15

Phe Ala Val Asn Gln Met
            20

<210> SEQ ID NO 150
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Met Glu Phe Thr Ser Asp His Ser Leu Asn Lys Phe Ile Ile Leu His
1               5                   10                  15

Tyr Ala Asn Asn Pro Phe
            20

<210> SEQ ID NO 151
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Met Trp Ser Ile Thr Asp His Asn Leu Asn Lys Phe Trp Ile Leu His
1               5                   10                  15

Tyr Ala Thr Lys His Gly
            20

<210> SEQ ID NO 152
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

-continued

```
Met Ala Phe Thr Val Thr Val Pro Lys Asp Leu Tyr Val Val Glu Tyr
1               5                   10                  15

Gly Ser Asn Met Thr Ile Glu Cys Lys Phe Pro Val Glu Lys Gln Leu
            20                  25                  30

Asp Leu Ala Ala Leu Ile Val Tyr Trp Glu Met Glu Asp Lys Asn Ile
        35                  40                  45

Ile Gln Phe Val His Gly Glu Glu Asp Leu Lys Val Gln His Ser Ser
    50                  55                  60

Tyr Arg Gln Arg Ala Arg Leu Leu Lys Asp Gln Leu Ser Leu Gly Asn
65                  70                  75                  80

Ala Ala Leu Gln Ile Thr Asp Val Lys Leu Gln Asp Ala Gly Val Tyr
                85                  90                  95

Arg Cys Met Ile Ser Tyr Gly Gly Ala Asp Tyr Lys Arg Ile Thr Val
            100                 105                 110

Lys Val Asn Ala Pro Tyr Asn Lys Ile Asn Gln Arg Ile Leu Val Val
            115                 120                 125

Asp Pro Val Thr Ser Glu His Glu Leu Thr Cys Gln Ala Glu Gly Tyr
    130                 135                 140

Pro Lys Ala Glu Val Ile Trp Thr Ser Ser Asp His Gln Val Leu Ser
145                 150                 155                 160

Gly Lys Thr Thr Thr Thr Asn Ser Lys Arg Glu Glu Lys Leu Phe Asn
                165                 170                 175

Val Thr Ser Thr Leu Arg Ile Asn Thr Thr Thr Asn Glu Ile Phe Tyr
                180                 185                 190

Cys Thr Phe Arg Arg Leu Asp Pro Glu Glu Asn His Thr Ala Glu Leu
            195                 200                 205

Val Ile Pro Glu Leu Pro Leu Ala His Pro Pro Asn Glu Arg Thr Gly
    210                 215                 220

Gly Ala Gly Gly Leu Asn Asp Ile Phe Glu Ala Gln Lys Ile Glu Trp
225                 230                 235                 240

His Glu Gly Gly Leu Glu His His His His His
                245                 250
```

```
<210> SEQ ID NO 153
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Gly Leu Asn Asp Ile Phe Glu Ala Gln Lys Ile Glu Trp His Glu
1               5                   10                  15
```

```
<210> SEQ ID NO 154
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 154

His His His His His His
1               5
```

-continued

```
<210> SEQ ID NO 155
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Tyr Pro Tyr Asp Val Pro Asp Tyr Ala
1               5

<210> SEQ ID NO 156
<211> LENGTH: 252
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Met Ala Phe Thr Ile Thr Ala Pro Lys Asp Leu Tyr Val Val Glu Tyr
1               5                   10                  15

Gly Ser Asn Val Thr Met Glu Cys Arg Phe Pro Val Glu Arg Glu Leu
                20                  25                  30

Asp Leu Leu Ala Leu Val Val Tyr Trp Glu Lys Glu Asp Glu Gln Val
            35                  40                  45

Ile Gln Phe Val Ala Gly Glu Glu Asp Leu Lys Pro Gln His Ser Asn
        50                  55                  60

Phe Arg Gly Arg Ala Ser Leu Pro Lys Asp Gln Leu Leu Lys Gly Asn
65                  70                  75                  80

Ala Ala Leu Gln Ile Thr Asp Val Lys Leu Gln Asp Ala Gly Val Tyr
                85                  90                  95

Cys Cys Ile Ile Ser Tyr Gly Gly Ala Asp Tyr Lys Arg Ile Thr Leu
                100                 105                 110

Lys Val Asn Ala Pro Tyr Arg Lys Ile Asn Gln Arg Ile Ser Val Asp
            115                 120                 125

Pro Ala Thr Ser Glu His Glu Leu Ile Cys Gln Ala Glu Gly Tyr Pro
    130                 135                 140

Glu Ala Glu Val Ile Trp Thr Asn Ser Asp His Gln Pro Val Ser Gly
145                 150                 155                 160

Lys Arg Ser Val Thr Thr Ser Arg Thr Glu Gly Met Leu Leu Asn Val
            165                 170                 175

Thr Ser Ser Leu Arg Val Asn Ala Thr Ala Asn Asp Val Phe Tyr Cys
            180                 185                 190

Thr Phe Trp Arg Ser Gln Pro Gly Gln Asn His Thr Ala Glu Leu Ile
            195                 200                 205

Ile Pro Glu Leu Pro Ala Thr His Pro Pro Gln Asn Arg Thr His Gly
    210                 215                 220

Gly Ala Gly Gly Leu Asn Asp Ile Phe Glu Ala Gln Lys Ile Glu Trp
225                 230                 235                 240

His Glu Gly Gly Leu Glu His His His His His His
                245                 250

<210> SEQ ID NO 157
<211> LENGTH: 154
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 157

Met Ala Leu Glu Val Pro Asn Gly Pro Trp Arg Ser Leu Thr Phe Tyr
1               5                   10                  15

Pro Ala Trp Leu Thr Val Ser Glu Gly Ala Asn Ala Thr Phe Thr Cys
            20                  25                  30

Ser Leu Ser Asn Trp Ser Glu Asp Leu Met Leu Asn Trp Asn Arg Leu
        35                  40                  45

Ser Pro Ser Asn Gln Thr Glu Lys Gln Ala Ala Phe Ser Asn Gly Leu
    50                  55                  60

Ser Gln Pro Val Gln Asp Ala Arg Phe Gln Ile Ile Gln Leu Pro Asn
65                  70                  75                  80

Arg His Asp Phe His Met Asn Ile Leu Asp Thr Arg Arg Asn Asp Ser
                85                  90                  95

Gly Ile Tyr Leu Cys Gly Ala Ile Ser Leu His Pro Lys Ala Lys Ile
            100                 105                 110

Glu Glu Ser Pro Gly Ala Glu Leu Val Val Thr Glu Arg Ile Leu Glu
        115                 120                 125

Thr Ser Thr Arg Tyr Pro Ser Gly Gly Tyr Pro Tyr Asp Val Pro Asp
    130                 135                 140

Tyr Ala Leu Glu His His His His His His
145                 150

<210> SEQ ID NO 158
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(10)
<223> OTHER INFORMATION: Any natural amino acid

<400> SEQUENCE: 158

Met Xaa Xaa Xaa Xaa Xaa Xaa Xaa Xaa Xaa Gly Ser Gly Thr Ser Gly
1               5                   10                  15

Ser Ser

<210> SEQ ID NO 159
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(18)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 159

Met Xaa Xaa Xaa Xaa Xaa Xaa Xaa Xaa Xaa Xaa Xaa Xaa Xaa Xaa Xaa
```

-continued

```
1               5               10              15

Xaa Xaa Gly Ser Gly Ser Ser Gly His His His His His Ser Ser
            20              25              30

<210> SEQ ID NO 160
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Ser Gly Gln Tyr Ala Ser Tyr His Cys Trp Cys Trp Arg Asp Pro Gly
1               5               10              15

Arg Ser Gly Gly Ser Lys
            20

<210> SEQ ID NO 161
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

His Tyr Pro Phe Arg Pro His Ala Asn Gln Ala Ser
1               5               10

<210> SEQ ID NO 162
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Trp His Arg Ser Tyr Tyr Thr Trp Asn Leu Asn Thr
1               5               10

<210> SEQ ID NO 163
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Trp His Phe Ser Tyr Asn Trp Arg Trp Leu Pro Pro
1               5               10

<210> SEQ ID NO 164
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164
```

```
Asp Tyr His Asp Pro Ser Leu Pro Thr Leu Arg Lys
1               5               10

<210> SEQ ID NO 165
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Ser Asn Gln Thr Asp Lys
1               5

<210> SEQ ID NO 166
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Asn
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Ser
<220> FEATURE:
<221> NAME/KEY: MOD_RES
<222> LOCATION: (4)..(4)
<223> OTHER INFORMATION: D-Lys
<220> FEATURE:
<221> NAME/KEY: MOD_RES
<222> LOCATION: (5)..(5)
<223> OTHER INFORMATION: D-Pro
<220> FEATURE:
<221> NAME/KEY: MOD_RES
<222> LOCATION: (6)..(6)
<223> OTHER INFORMATION: D-Thr
<220> FEATURE:
<221> NAME/KEY: MOD_RES
<222> LOCATION: (7)..(7)
<223> OTHER INFORMATION: D-Asp
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Gln
<220> FEATURE:
<221> NAME/KEY: MOD_RES
<222> LOCATION: (10)..(10)
<223> OTHER INFORMATION: D-Tyr
<220> FEATURE:
<221> NAME/KEY: MOD_RES
<222> LOCATION: (11)..(11)
<223> OTHER INFORMATION: D-His
<220> FEATURE:
<221> NAME/KEY: MOD_RES
<222> LOCATION: (12)..(12)
<223> OTHER INFORMATION: D-Phe

<400> SEQUENCE: 166
```

```
Xaa Xaa Xaa Xaa Xaa Xaa Xaa Xaa Xaa Xaa Xaa Xaa
1               5                   10

<210> SEQ ID NO 167
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-His
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: D-His
<220> FEATURE:
<221> NAME/KEY: MOD_RES
<222> LOCATION: (5)..(5)
<223> OTHER INFORMATION: D-His
<220> FEATURE:
<221> NAME/KEY: MOD_RES
<222> LOCATION: (6)..(6)
<223> OTHER INFORMATION: D-Thr
<220> FEATURE:
<221> NAME/KEY: MOD_RES
<222> LOCATION: (7)..(7)
<223> OTHER INFORMATION: D-His
<220> FEATURE:
<221> NAME/KEY: MOD_RES
<222> LOCATION: (8)..(8)
<223> OTHER INFORMATION: D-Asn
<220> FEATURE:
<221> NAME/KEY: MOD_RES
<222> LOCATION: (9)..(9)
<223> OTHER INFORMATION: D-Leu
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Leu
<220> FEATURE:
<221> NAME/KEY: MOD_RES
<222> LOCATION: (12)..(12)
<223> OTHER INFORMATION: D-Pro

<400> SEQUENCE: 167

Xaa Xaa Xaa Xaa Xaa Xaa Xaa Xaa Xaa Xaa Xaa Xaa
1               5                   10

<210> SEQ ID NO 168
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Gly Ser Gly Ser Gly Ser Thr Tyr Leu Cys Gly Ala Ile Ser Leu Ala
```

-continued

```
1              5              10             15

Pro Lys Ala Gln Ile Lys Glu Ser Leu
           20             25

<210> SEQ ID NO 169
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Lys, wherein the side chain of Lys is connected
      to the sequence SNTSESF

<400> SEQUENCE: 169

Ser Asn Thr Ser Glu Ser Phe Xaa Phe Arg Val Thr Gln Leu Ala Pro
1              5              10             15

Lys Ala Gln Ile Lys Glu
           20

<210> SEQ ID NO 170
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Phe" or "Lys" or "Trp" or "Tyr"
<220> FEATURE:
<221> NAME/KEY: VARIANT
<222> LOCATION: (3)..(3)
<223> OTHER INFORMATION: /replace="His" or "Lys" or "Ser" or "Thr"
<220> FEATURE:
<221> NAME/KEY: VARIANT
<222> LOCATION: (4)..(4)
<223> OTHER INFORMATION: /replace="His" or "Lys" or "Leu" or "Ile" or
      "Asn" or "Gln" or "Arg" or "Ser" or "Thr"
<220> FEATURE:
<221> NAME/KEY: VARIANT
<222> LOCATION: (5)..(5)
<223> OTHER INFORMATION: /replace="Phe" or "Ser" or "Asn" or "Val" or
      "Thr"
<220> FEATURE:
<221> NAME/KEY: VARIANT
<222> LOCATION: (8)..(8)
<223> OTHER INFORMATION: /replace="Asn" or "Ser" or "Thr" or "Val"
<220> FEATURE:
<221> NAME/KEY: VARIANT
<222> LOCATION: (13)..(13)
<223> OTHER INFORMATION: /replace="Leu" or "Ile" or "Trp" or "Tyr"
<220> FEATURE:
<221> NAME/KEY: VARIANT
<222> LOCATION: (15)..(15)
<223> OTHER INFORMATION: /replace="Met"
<220> FEATURE:
<221> NAME/KEY: VARIANT
<222> LOCATION: (17)..(17)
<223> OTHER INFORMATION: /replace="Phe" or "Asn" or "Gln" or "Tyr"
<220> FEATURE:
<221> NAME/KEY: VARIANT
<222> LOCATION: (18)..(18)
<223> OTHER INFORMATION: /replace="Ser" or "Thr"
<220> FEATURE:
<221> NAME/KEY: VARIANT
<222> LOCATION: (19)..(19)
<223> OTHER INFORMATION: /replace="Phe" or "His" or "Ile" or "Lys" or
```

-continued

```
        "Leu" or "Met" or "Asn" or "Gln" or "Arg" or "Ser" or "Thr" or
        "Val"
<220> FEATURE:
<221> NAME/KEY: VARIANT
<222> LOCATION: (20)..(20)
<223> OTHER INFORMATION: /replace="Lys" or "Leu" or "Asn" or "Gln" or
        "Arg" or "Ser" or "Thr" or "Tyr"
<220> FEATURE:
<221> NAME/KEY: VARIANT
<222> LOCATION: (21)..(21)
<223> OTHER INFORMATION: /replace="Gly" or "His" or "Lys" or "Asn" or
        "Pro" or "Gln" or "Arg" or "Ser" or "Thr"
<220> FEATURE:
<221> NAME/KEY: VARIANT
<222> LOCATION: (22)..(22)
<223> OTHER INFORMATION: /replace="Asp" or "Phe" or "Gly" or "Ile" or
        "Lys" or "Leu" or "Asn" or "Gln" or "Met" or "Ser" or "Thr"
<220> FEATURE:
<221> NAME/KEY: SITE
<222> LOCATION: (1)..(22)
<223> OTHER INFORMATION: /note="Variant residues given in the sequence
        have no preference with respect to those in the annotations
        for variant positions"

<400> SEQUENCE: 170

Met Glu Phe Asp Ala Asp His Ile Leu Asn Lys Phe Phe Ile Leu His
1               5                   10                  15

Glu Ala Ala His Ala Ala
            20

<210> SEQ ID NO 171
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"
<220> FEATURE:
<221> NAME/KEY: VARIANT
<222> LOCATION: (2)..(2)
<223> OTHER INFORMATION: /replace="Lys" or "Trp" or "Tyr"
<220> FEATURE:
<221> NAME/KEY: VARIANT
<222> LOCATION: (3)..(3)
<223> OTHER INFORMATION: /replace="His" or "Ser" or "Thr"
<220> FEATURE:
<221> NAME/KEY: VARIANT
<222> LOCATION: (4)..(4)
<223> OTHER INFORMATION: /replace="Gln" or "Leu" or "Ser" or "Arg" or
        "His" or "Thr" or "Ile"
<220> FEATURE:
<221> NAME/KEY: VARIANT
<222> LOCATION: (5)..(5)
<223> OTHER INFORMATION: /replace="Ser" or "Asn" or "Val" or "Thr"
<220> FEATURE:
<221> NAME/KEY: VARIANT
<222> LOCATION: (8)..(8)
<223> OTHER INFORMATION: /replace="Asn" or "Ser" or "Thr" or "Val"
<220> FEATURE:
<221> NAME/KEY: VARIANT
<222> LOCATION: (13)..(13)
<223> OTHER INFORMATION: /replace="Leu" or "Ile" or "Trp" or "Tyr"
<220> FEATURE:
<221> NAME/KEY: VARIANT
<222> LOCATION: (15)..(15)
<223> OTHER INFORMATION: /replace="Met"
<220> FEATURE:
<221> NAME/KEY: VARIANT
<222> LOCATION: (17)..(17)
<223> OTHER INFORMATION: /replace="Phe" or "Gln" or "Tyr"
<220> FEATURE:
<221> NAME/KEY: VARIANT
<222> LOCATION: (18)..(18)
<223> OTHER INFORMATION: /replace="Ser" or "Thr"
<220> FEATURE:
```

```
<221> NAME/KEY: VARIANT
<222> LOCATION: (19)..(19)
<223> OTHER INFORMATION: /replace="Phe" or "Leu" or "Asn" or "Arg" or
      "Thr" or "Val"
<220> FEATURE:
<221> NAME/KEY: VARIANT
<222> LOCATION: (20)..(20)
<223> OTHER INFORMATION: /replace="Gln" or "Lys"
<220> FEATURE:
<221> NAME/KEY: VARIANT
<222> LOCATION: (21)..(21)
<223> OTHER INFORMATION: /replace="Pro" or "Gln" or "Ser"
<220> FEATURE:
<221> NAME/KEY: VARIANT
<222> LOCATION: (22)..(22)
<223> OTHER INFORMATION: /replace="Gly" or "Asn" or "Gln" or "Met" or
      "Ser" or "Thr"
<220> FEATURE:
<221> NAME/KEY: SITE
<222> LOCATION: (1)..(22)
<223> OTHER INFORMATION: /note="Variant residues given in the sequence
      have no preference with respect to those in the annotations
      for variant positions"

<400> SEQUENCE: 171

Met Glu Phe Asp Ala Asp His Ile Leu Asn Lys Phe Phe Ile Leu His
1               5                   10                  15

Glu Ala Ala Asn His Phe
            20

<210> SEQ ID NO 172
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: AcPhe
<220> FEATURE:
<221> NAME/KEY: MOD_RES
<222> LOCATION: (2)..(2)
<223> OTHER INFORMATION: NMeAla
<220> FEATURE:
<221> NAME/KEY: MOD_RES
<222> LOCATION: (11)..(11)
<223> OTHER INFORMATION: NMeNle
<220> FEATURE:
<221> NAME/KEY: MOD_RES
<222> LOCATION: (12)..(12)
<223> OTHER INFORMATION: NMeNle

<400> SEQUENCE: 172

Xaa Xaa Asn Pro His Leu Ser Trp Ser Trp Xaa Xaa Arg Cys Gly
1               5                   10                  15

<210> SEQ ID NO 173
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: AcPhe
<220> FEATURE:
<221> NAME/KEY: MOD_RES
<222> LOCATION: (2)..(2)
```

```
<223> OTHER INFORMATION: NMePhe
<220> FEATURE:
<221> NAME/KEY: MOD_RES
<222> LOCATION: (3)..(3)
<223> OTHER INFORMATION: NMeNle
<220> FEATURE:
<221> NAME/KEY: MOD_RES
<222> LOCATION: (4)..(4)
<223> OTHER INFORMATION: Sarcosine
<220> FEATURE:
<221> NAME/KEY: MOD_RES
<222> LOCATION: (7)..(7)
<223> OTHER INFORMATION: NMePhe
<220> FEATURE:
<221> NAME/KEY: MOD_RES
<222> LOCATION: (9)..(9)
<223> OTHER INFORMATION: Sarcosine

<400> SEQUENCE: 173

Xaa Xaa Xaa Xaa Asp Val Xaa Tyr Xaa Trp Tyr Leu Cys Gly
1               5                   10

<210> SEQ ID NO 174
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: AcPhe

<400> SEQUENCE: 174

Xaa Leu Ile Val Ile Arg Asp Arg Val Phe Arg Cys Gly
1               5                   10

<210> SEQ ID NO 175
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: AcTyr
<220> FEATURE:
<221> NAME/KEY: MOD_RES
<222> LOCATION: (2)..(2)
<223> OTHER INFORMATION: NMeAla
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Trp(Me)
<220> FEATURE:
<221> NAME/KEY: MOD_RES
<222> LOCATION: (11)..(11)
<223> OTHER INFORMATION: NMeNle
<220> FEATURE:
<221> NAME/KEY: MOD_RES
<222> LOCATION: (12)..(12)
<223> OTHER INFORMATION: NMeNle
<220> FEATURE:
<221> NAME/KEY: MOD_RES
<222> LOCATION: (13)..(13)
<223> OTHER INFORMATION: Orn
```

<400> SEQUENCE: 175

Xaa Xaa Asn Pro His Leu Xaa Trp Ser Xaa Xaa Xaa Xaa Cys Gly
1               5                   10                  15

<210> SEQ ID NO 176
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
tttttttttt ttgctggagc caga                                              24

<210> SEQ ID NO 177
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(22)
<223> OTHER INFORMATION: Any amino acid

<400> SEQUENCE: 177

Met Xaa Xaa Xaa Xaa Asp His Xaa Leu Asn Lys Phe Xaa Ile Xaa His
1               5                   10                  15

Xaa Xaa Xaa Xaa Xaa Xaa
            20

<210> SEQ ID NO 178
<211> LENGTH: 290
<212> TYPE: PRT
<213> ORGANISM: Homo sapiens

<400> SEQUENCE: 178

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser

```
        65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
        275                 280                 285

Glu Thr
    290

<210> SEQ ID NO 179
<211> LENGTH: 290
<212> TYPE: PRT
<213> ORGANISM: Mus musculus

<400> SEQUENCE: 179

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
                35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
                100                 105                 110

Cys Cys Ile Ile Ser Tyr Gly Gly Ala Asp Tyr Lys Arg Ile Thr Leu
                115                 120                 125

Lys Val Asn Ala Pro Tyr Arg Lys Ile Asn Gln Arg Ile Ser Val Asp
        130                 135                 140
```

```
Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
                260                 265                 270

Gly Val Glu Asp Thr Ser Ser Lys Asn Arg Asn Asp Thr Gln Phe Glu
            275                 280                 285

Glu Thr
    290

<210> SEQ ID NO 180
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Pro Ile Phe Leu Asp His Ile Leu Asn Lys Phe Trp Ile Leu His Tyr
1               5                   10                  15

Ala

<210> SEQ ID NO 181
<211> LENGTH: 273
<212> TYPE: PRT
<213> ORGANISM: Homo sapiens

<400> SEQUENCE: 181

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125
```

-continued

```
His Ile Leu Lys Val Pro Glu Thr Asp Glu Val Glu Leu Thr Cys Gln
    130             135             140

Ala Thr Gly Tyr Pro Leu Ala Glu Val Ser Trp Pro Asn Val Ser Val
145             150             155             160

Pro Ala Asn Thr Ser His Ser Arg Thr Pro Glu Gly Leu Tyr Gln Val
                165             170             175

Thr Ser Val Leu Arg Leu Lys Pro Pro Pro Gly Arg Asn Phe Ser Cys
            180             185             190

Val Phe Gln Asn Thr His Val Arg Glu Leu Thr Leu Ala Ser Ile Asp
        195             200             205

Leu Gln Ser Gln Met Glu Pro Arg Thr His Pro Thr Trp Leu Leu His
    210             215             220

Ile Phe Ile Pro Phe Cys Ile Ile Ala Phe Ile Phe Ile Ala Thr Val
225             230             235             240

Ile Ala Leu Arg Lys Gln Leu Cys Gln Lys Leu Tyr Ser Ser Lys Asp
            245             250             255

Thr Thr Lys Arg Pro Val Thr Thr Thr Lys Arg Glu Val Asn Ser Ala
            260             265             270

Ile
```

```
<210> SEQ ID NO 182
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Ser Asn Thr Ser Glu Ser Phe
1               5
```